US012685523B2

(12) United States Patent
Azar et al.

(10) Patent No.: US 12,685,523 B2
(45) Date of Patent: Jul. 21, 2026

(54) DEVICES FOR DELIVERING HELICAL ANCHORS

(71) Applicant: MEACOR, INC., Ayer, MA (US)

(72) Inventors: Toufic Azar, Montreal (CA); Renzo Cecere, Mont-Royal (CA); Elia Nammour, Deel el mehdi (LB); Bechara Yared, Aoukar (LB); Daniel Farhat, Ghobeiry (LB); Ahmad Hijazi, Beirut (LB)

(73) Assignee: MEACOK, INC., Irvine, CA (US)

( * ) Notice: Subject to any disclaimer, the term of this patent is extended or adjusted under 35 U.S.C. 154(b) by 992 days.

(21) Appl. No.: 17/848,280

(22) Filed: Jun. 23, 2022

(65) Prior Publication Data

US 2022/0330980 A1 Oct. 20, 2022

Related U.S. Application Data

(63) Continuation of application No. 16/771,835, filed as application No. PCT/IB2018/060073 on Dec. 14, 2018, now Pat. No. 11,399,867.

(Continued)

(51) Int. Cl.
  *A61B 17/04* (2006.01)
  *A61B 17/34* (2006.01)
  (Continued)

(52) U.S. Cl.
  CPC ...... *A61B 17/0401* (2013.01); *A61B 17/3468* (2013.01); *A61F 2/2427* (2013.01);
  (Continued)

(58) Field of Classification Search
  CPC . A61B 17/0401; A61B 17/064; A61B 17/068; A61B 2017/0409;
  (Continued)

(56) References Cited

U.S. PATENT DOCUMENTS 5,477,856 A   12/1995 Lundquist
5,810,882 A * 9/1998 Bolduc ................ A61B 17/064
                                              606/151

(Continued)

FOREIGN PATENT DOCUMENTS

AU   2002354761   9/2009
EP      1774986   4/2007
(Continued)

OTHER PUBLICATIONS

Written Opinion of the International Searching Authority issued by the World Intellectual Property Organization on Mar. 28, 2019 for PCT application PCTIB2018060073 from which the present application claims priority.

(Continued)

*Primary Examiner* — Wesley G Harris
(74) *Attorney, Agent, or Firm* — William A. English; Vista IP Law Group LLP

(57)          ABSTRACT

A hollow catheter segment comprising a longitudinally extending slot region including a slot, at least one longitudinally backbone region and longitudinally extending intermediate regions between either adjacent backbone regions or between one of the backbone regions and the slot region, the slot and backbone regions being all disjoint from each other, the slot region, at least one backbone region and intermediate regions being all distributed circumferentially around the driving section. The catheter segment includes plurality of first and second slits extending radially therethrough and disjoint from each other, each first slit extending around the catheter segment between slot region first and second side edges and the second slits each extending between one of a backbone region first and second side edges and either a backbone region first or second side edges of an adjacent backbone region or the slot.

29 Claims, 38 Drawing Sheets

Related U.S. Application Data

(60) Provisional application No. 62/598,525, filed on Dec. 14, 2017.

(51) Int. Cl.

| | |
|---|---|
| *A61F 2/24* | (2006.01) |
| *A61B 17/00* | (2006.01) |
| *A61B 17/064* | (2006.01) |
| *A61B 17/068* | (2006.01) |

(52) U.S. Cl.

CPC .. *A61F 2/2466* (2013.01); *A61B 2017/00292* (2013.01); *A61B 2017/00309* (2013.01); *A61B 2017/00477* (2013.01); *A61B 2017/0409* (2013.01); *A61B 2017/0441* (2013.01); *A61B 2017/0464* (2013.01); *A61B 17/064* (2013.01); *A61B 2017/0649* (2013.01); *A61B 17/068* (2013.01); *A61F 2220/0016* (2013.01); *A61F 2230/0091* (2013.01)

(58) Field of Classification Search

CPC .......... A61B 2017/0649; A61B 17/869; A61B 17/3468; A61B 2017/00292; A61B 2017/00309; A61B 2017/00477; A61B 2017/0441; A61B 2017/0464; A61M 25/0013; A61F 2/2427; A61F 2/2466; A61F 2220/0016; A61F 2230/0091

See application file for complete search history.

(56) References Cited

U.S. PATENT DOCUMENTS

| | | | |
|---|---|---|---|
| 5,837,006 | A | 11/1998 | Ocel et al. |
| 6,296,656 | B1 | 10/2001 | Bolduc et al. |
| 6,704,605 | B2 | 3/2004 | Soltis et al. |
| 8,092,444 | B2 | 1/2012 | Lentz et al. |
| 8,579,919 | B2 | 11/2013 | Bolduc et al. |
| 8,747,462 | B2 | 6/2014 | Hill et al. |
| 8,784,337 | B2 | 7/2014 | Voeller et al. |
| 8,821,477 | B2 | 9/2014 | Northrop et al. |
| 8,870,790 | B2 | 10/2014 | Davis et al. |
| 8,903,513 | B2 | 12/2014 | Ollivier |
| 9,295,807 | B2 | 3/2016 | Chin et al. |
| 9,327,112 | B2 | 5/2016 | Ollivier |
| 9,462,932 | B2 | 10/2016 | Ostrovsky et al. |
| 9,788,828 | B2 * | 10/2017 | Housman ............. A61B 17/869 |
| 11,399,867 | B2 | 8/2022 | Azar et al. |
| 2003/0229350 | A1 * | 12/2003 | Kay ....................... A61B 17/86 470/10 |
| 2004/0193217 | A1 * | 9/2004 | Lubbers ............... A61B 17/683 606/232 |
| 2005/0251240 | A1 | 11/2005 | Doan |
| 2006/0247642 | A1 * | 11/2006 | Stone ................. A61B 17/8605 623/13.14 |
| 2007/0135763 | A1 | 6/2007 | Musbach et al. |
| 2007/0244555 | A1 | 10/2007 | Rafiee et al. |
| 2008/0319520 | A1 | 12/2008 | Hill |
| 2009/0118704 | A1 | 5/2009 | Sharrow et al. |
| 2010/0076462 | A1 | 3/2010 | Bakos et al. |
| 2012/0022557 | A1 * | 1/2012 | Cabiri .................. A61B 17/064 606/139 |
| 2013/0096672 | A1 * | 4/2013 | Reich ................. A61B 17/0401 623/2.11 |
| 2016/0074131 | A1 | 3/2016 | Lubinski |
| 2017/0135692 | A1 | 5/2017 | Belson et al. |

FOREIGN PATENT DOCUMENTS

| | | |
|---|---|---|
| EP | 2246091 | 11/2010 |
| WO | WO-2016098082 A1 | 6/2016 |
| WO | WO-2019116322 A1 | 6/2019 |

OTHER PUBLICATIONS

International Search Report issued by the World Intellectual Property Organization on Mar. 28, 2019 for PCT application PCTIB2018060073 from which the present application claims priority.

U.S. Appl. No. 16/771,835 Notice of Allowance dated Jun. 20, 2022.

U.S. Appl. No. 16/771,835 Office Action dated Apr. 13, 2022.

* cited by examiner

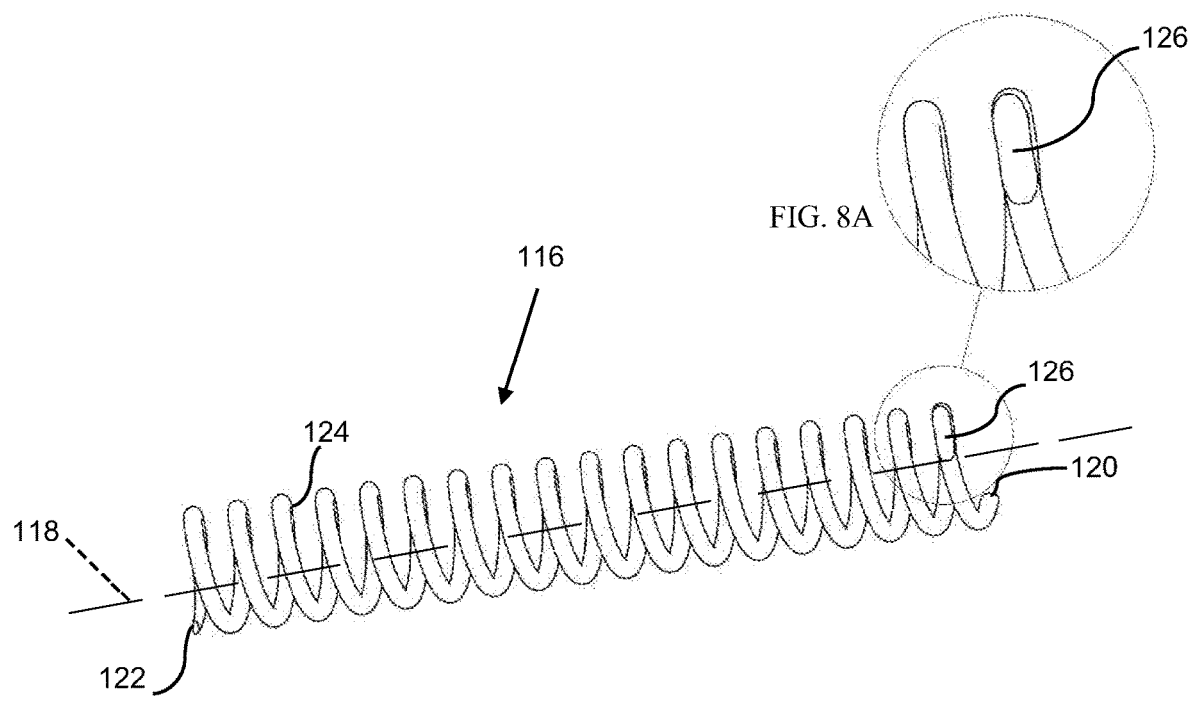
FIG. 8A
FIG. 8
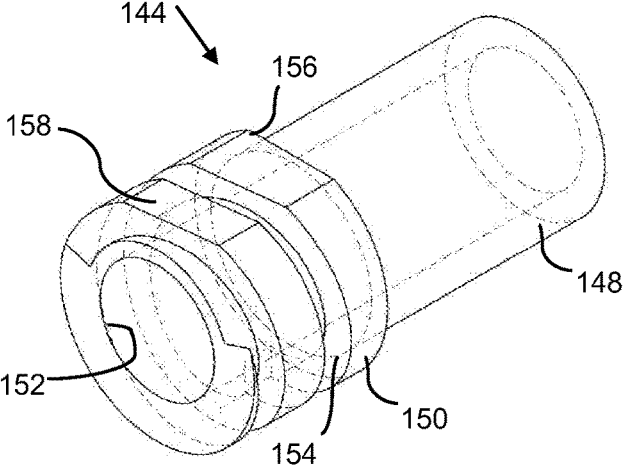
FIG. 9

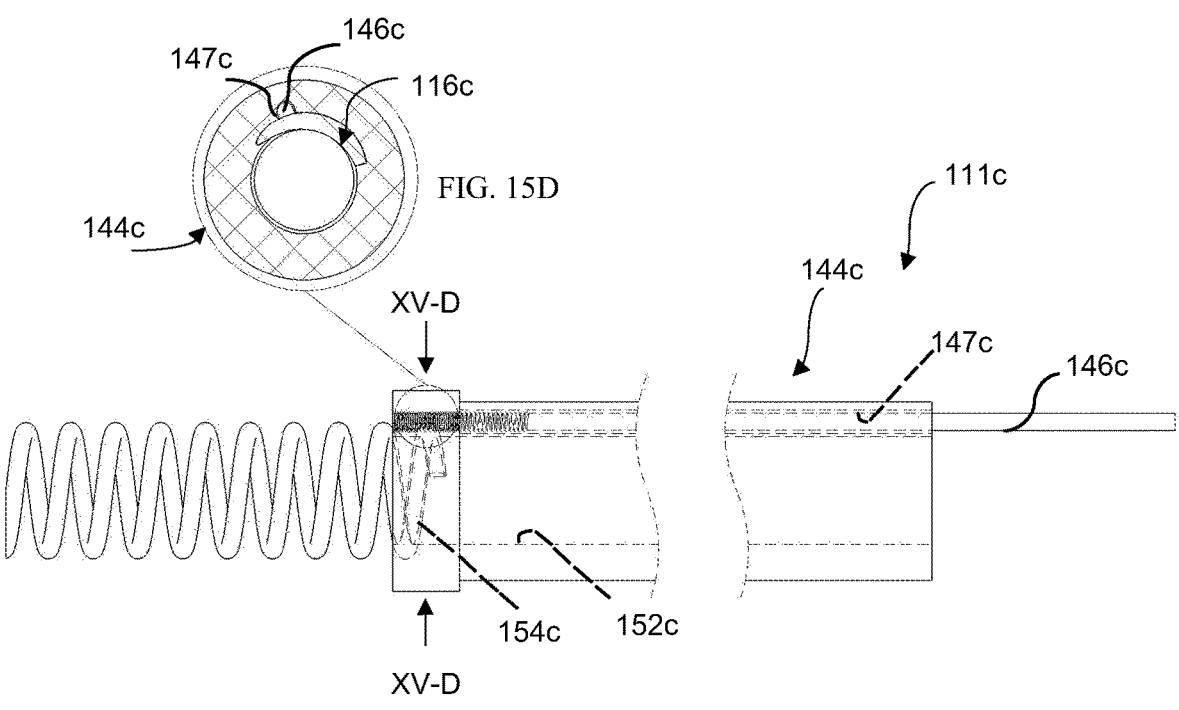
FIG. 15D
FIG. 15A
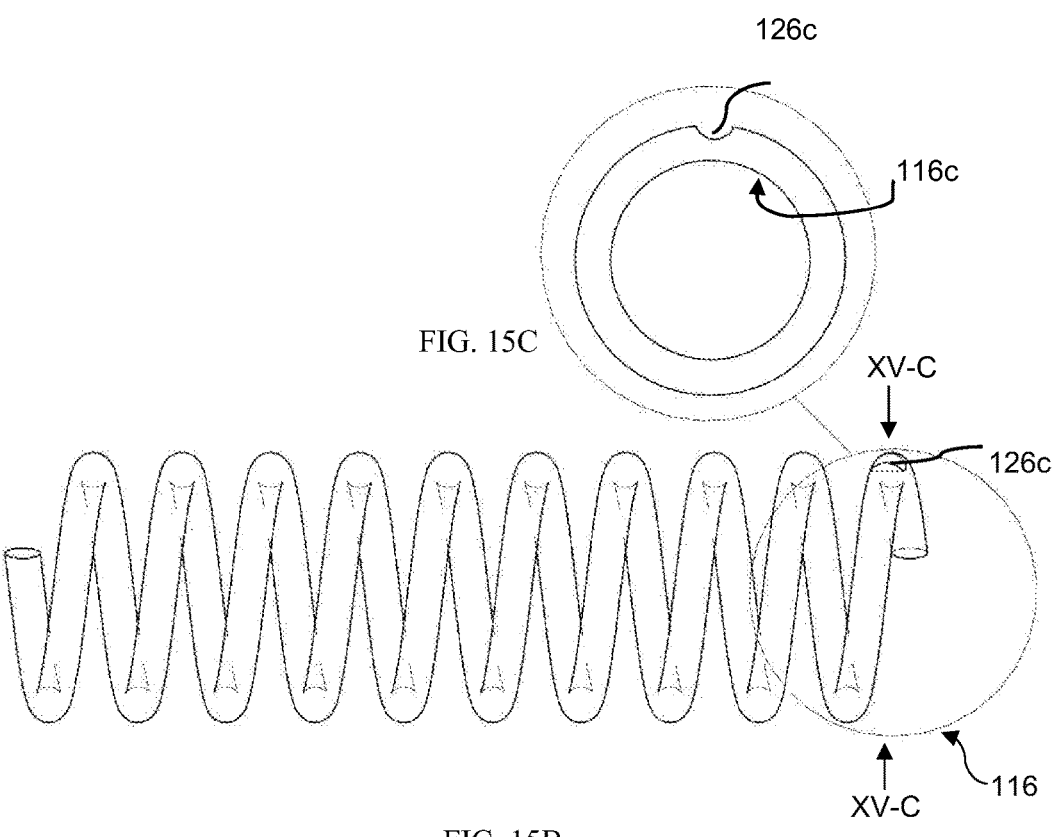
FIG. 15C
FIG. 15B

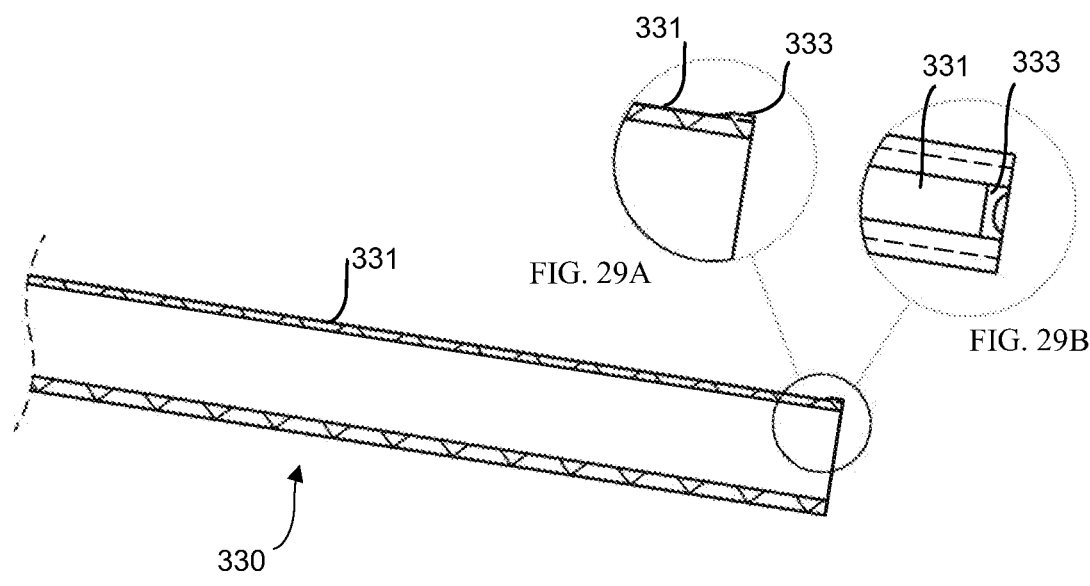
FIG. 29A
FIG. 29B
FIG. 29
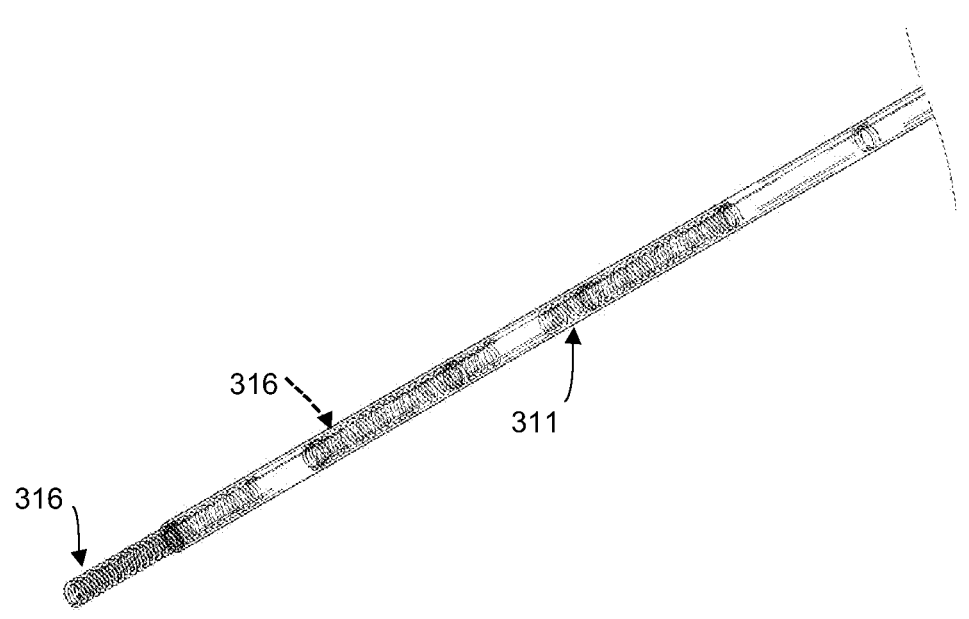
FIG. 30

134g

147g

170g

144g

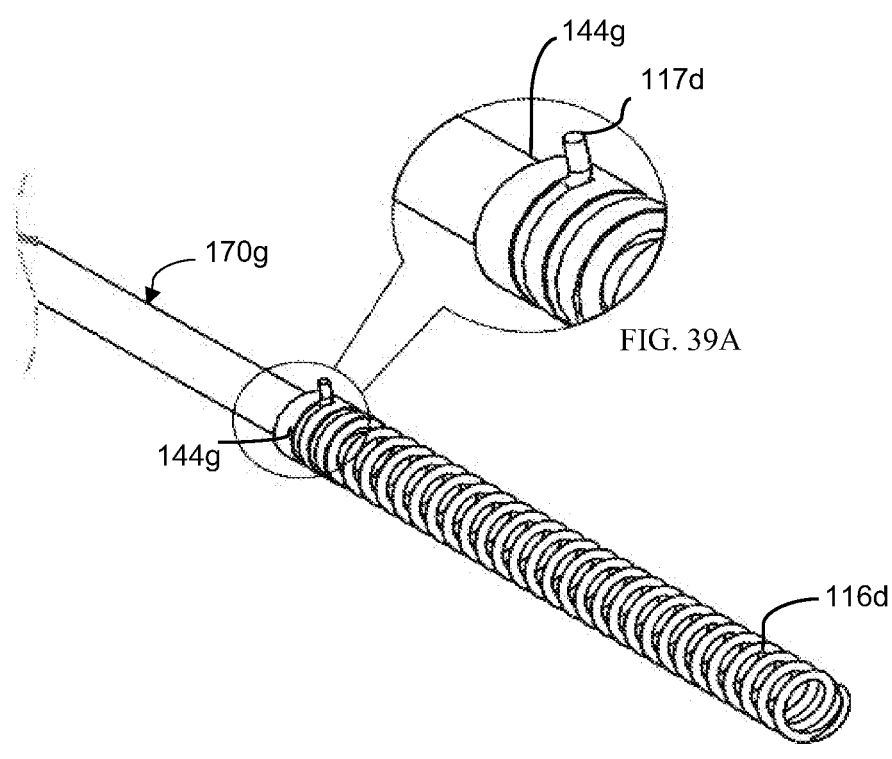
FIG. 39A
FIG. 39
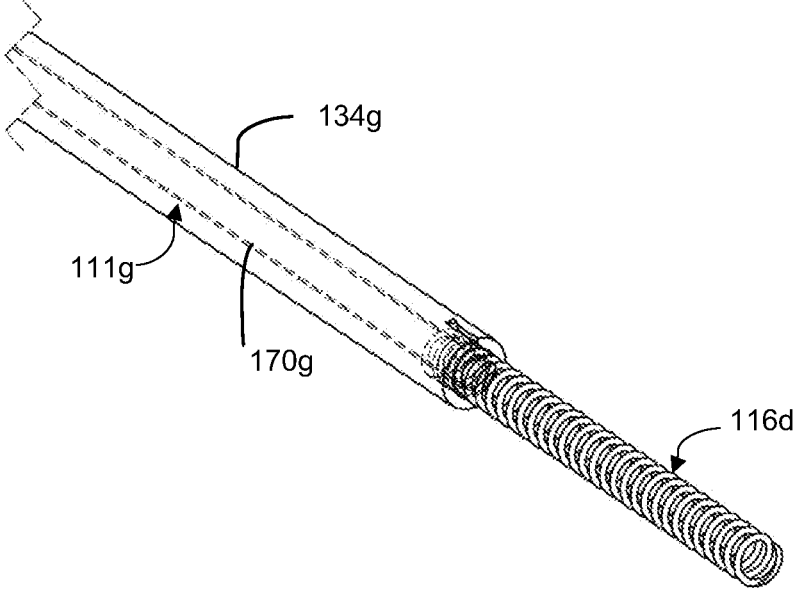
FIG. 40

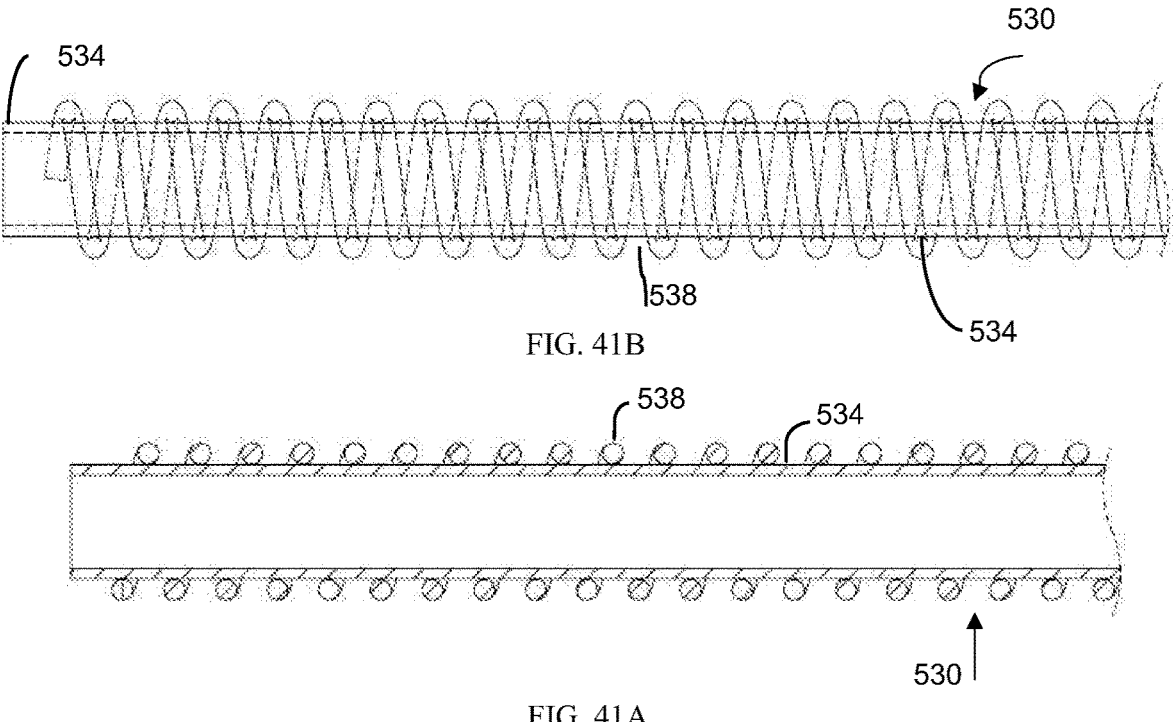
FIG. 41B
FIG. 41A
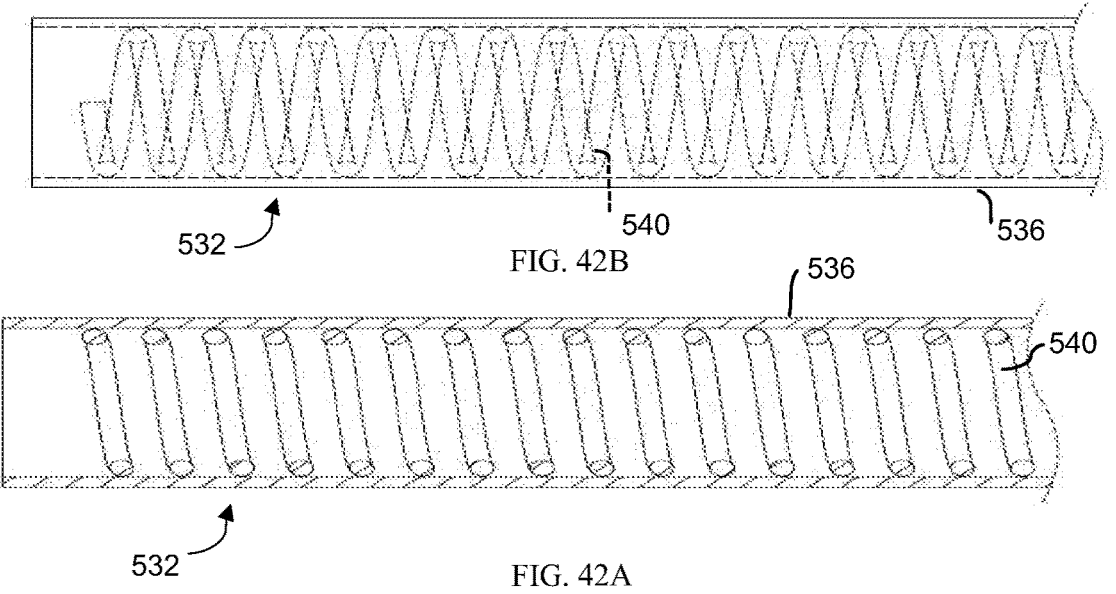
FIG. 42B
FIG. 42A

516a

522a

516b

522b

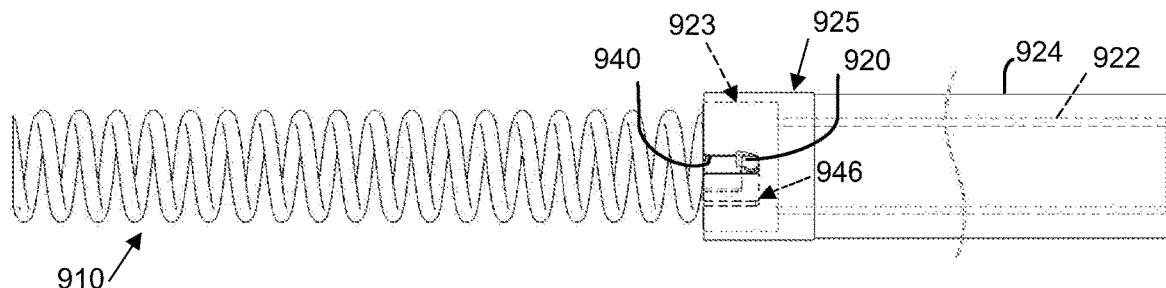
FIG. 75
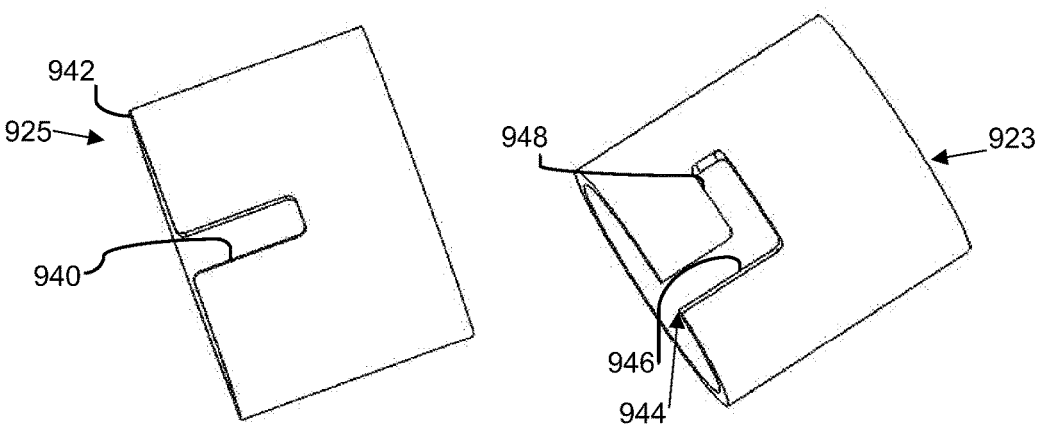
FIG. 76                    FIG. 77
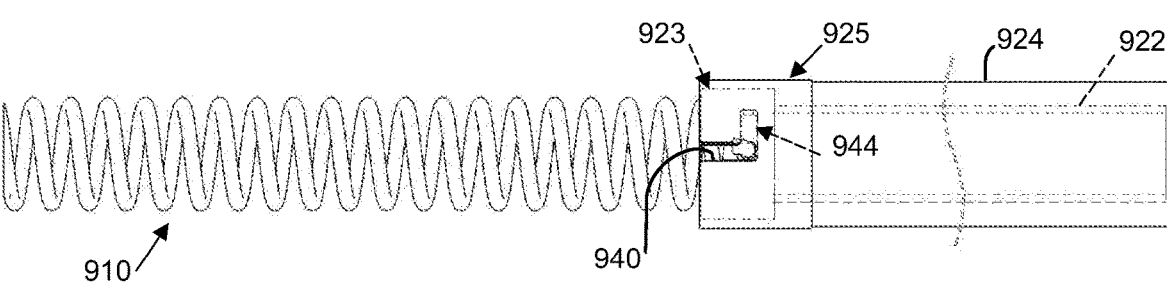
FIG. 78

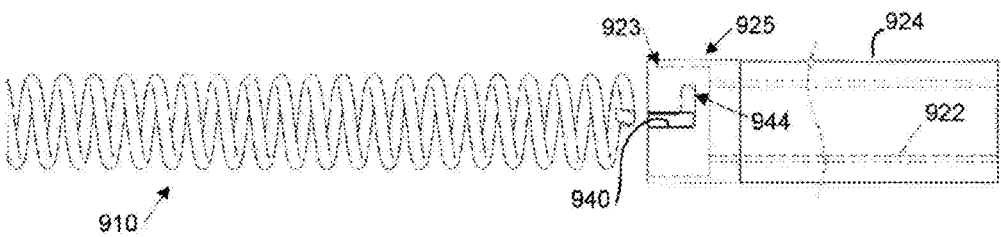
FIG. 79
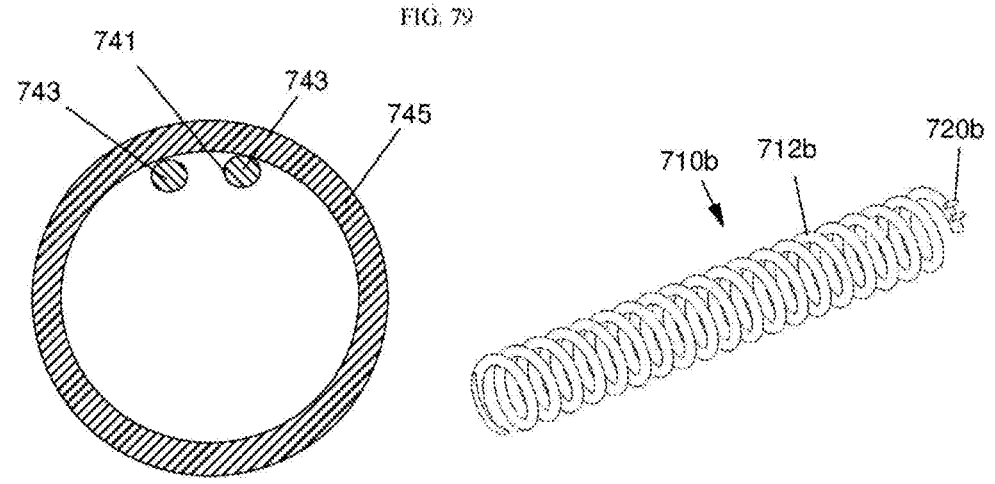
FIG. 80
FIG. 81
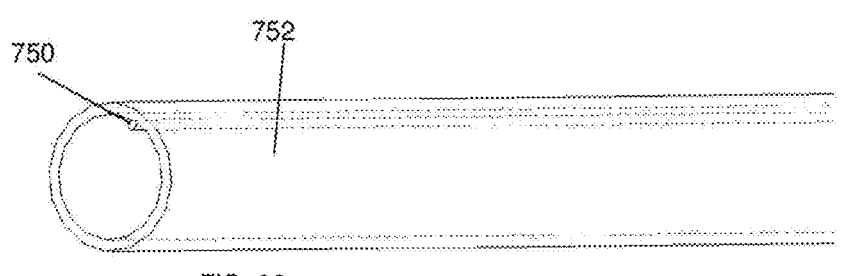
FIG. 82
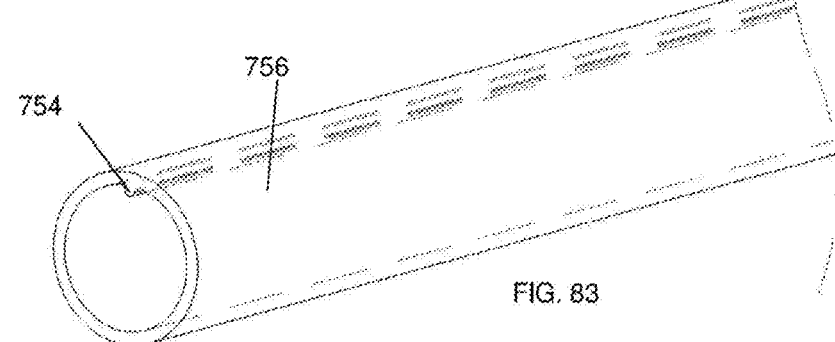
FIG. 83

DEVICES FOR DELIVERING HELICAL ANCHORS

FIELD OF THE INVENTION

The present invention relates to the general field of surgical devices, and is more particularly concerned with a flexible catheter segment.

BACKGROUND

PCT patent application PCT/IB2015/059806 filed Dec. 19, 2015 in the name of AZAR et al. describes a system for implanting a helical anchor in tissues, for example during cardiac surgery. The system includes an elongated guide that can be selectively adhered parallel to a tissue and a driving mechanism allowing rotation of the anchor around the guide so that the anchor can be advanced in the tissue. While the system described in the aforementioned PCT patent application is suitable for its purpose, it is not well adapted to the anchoring of many anchors serially at the same location.

Accordingly, there exists a need for improved helical anchor driving systems and for such systems including flexible catheter segments. An object of the invention is to provide such systems.

SUMMARY OF THE INVENTION

Generally speaking, the present document describes various systems for driving helical anchors over an elongated guide. In some embodiments, the elongated member has a tip that can be adhered to tissue either through cryoadhesion or through suction. However, in other embodiments, the tip of the guide is adhered to tissue using any other suitable method or is simply free to move relative to the tissue. Typically, the proposed systems is used in percutaneous surgery, but may be used in other contexts.

The proposed system is used to perform three functions. First, the system is used to advance the helical anchor along the guide. Second, the system is used to rotate the anchor in the tissue so that the anchor is advanced in the tissue. Finally, the system is used to release the anchor from the system so that the system can be completely removed from the patient with the anchor remaining embedded in the tissue.

Advantageously, the proposed system is usable in some embodiments to advance many successive helical anchors without requiring withdrawal and reinsertion of the guide. This decreases the duration of the surgical procedure and improves accuracy of anchor positioning. In other embodiments, the system is used to implant anchors individually.

The present application claims priority from U.S. provisional patent application 62/598,525 filed Dec. 14, 2017, the contents of which is hereby incorporated by reference in its entirety.

In a broad aspect, there is provided a system for driving a helical anchor into biological tissue, the helical anchor including a substantially helical anchor body defining anchor body proximal and distal ends and an anchor body passageway extending therethrough between the anchor body proximal and distal ends, the anchor body being delimited inside a generally cylindrical shape, an anchor protrusion extending radially from the anchor body at the anchor body proximal end, the system comprising: substantially elongated inner and outer drivers concentric relative to each other and defining a driver passageway therebetween, the helical anchor being mountable between the inner and outer drivers in the driver passageway, the inner driver defining longitudinally opposed inner driver proximal and distal ends and the outer driver defining longitudinally opposed outer driver proximal and distal ends, the inner and outer drivers being axially rotatable relative to each other and longitudinally substantially fixed relative to each other; a first driver selected from the inner and outer drivers defining a first driver surface facing the driver passageway and provided with at least one protrusion protruding in the driver passageway and configured for engaging the helical anchor when the helical anchor is mounted in the driver passageway and preventing pure translation of the helical anchor along the first driver while allowing helical movements of the helical anchor relative to the first driver; a second driver selected from the inner and outer drivers and differing from the first driver including a driving section extending from a second driver distal end towards a second driver proximal end, the driving section being provided with a slot extending therealong from the second driver distal end towards the second driver proximal end, the slot being configured and sized for receiving the anchor protrusion thereinto and allowing movements of the anchor protrusion along the slot; and an actuator operatively coupled to the inner and outer drivers at the inner and outer driver proximal ends for selectively rotating the inner and outer driver relative to each other.

There may also be provided a system wherein the driving section is hollow and defines opposed driving section inner and outer surfaces, the slot extending between the driving section inner and outer surfaces; the driving section defines a slot region, at least one backbone region and intermediate regions all distributed circumferentially around the driving section, each intermediate region extending between either adjacent backbone regions or between one of the backbone regions and the slot region, the slot, backbone and intermediate regions each extending along the driving section from a distalmost location to a proximalmost location, the slot and backbone regions being all disjoint from each other; the slot region includes the slot and extends circumferentially along a circumferential width wider than the slot; the slot region defines opposed slot region first and second side edges, the slot being spaced apart from each of the slot region first and second side edges; each backbone region defines opposed backbone region first and second side edges; the driving section further defines a plurality of first slits and a plurality of second slits, each of the first and second slits extending between the driving section inner and outer surfaces, the first and second slits being all disjoint from each other, each first slit extending around the driving section between the slot region first and second side edges and the second slits each extending between one of a backbone region first and second side edges and either a backbone region first or second side edge of an adjacent backbone region or the slot.

There may also be provided a system wherein the slot and backbone regions are substantially parallel to each other.

There may also be provided a system wherein the slot and backbone regions are substantially helical around the second driver.

There may also be provided a system wherein the second slits define slit groups including second slits in prolongation of each other around the driving section, each slit group defining an interrupted slit extending around the driving section and interrupted in the backbone regions.

There may also be provided a system wherein the first slits and the slit groups alternate longitudinally along the driving section.

There may also be provided a system wherein the first and second slits are each substantially circumferential.

There may also be provided a system wherein all the first slits are substantially parallel to each other.

There may also be provided a system wherein all the second slits are parallel to the first slits.

There may also be provided a system wherein all the first and second slits are all arc segment shaped with a center of rotation at a longitudinal axis of the driving section.

There may also be provided a system wherein the slot is helical around the driving section.

There may also be provided a system wherein the driving section includes two backbone regions.

There may also be provided a system wherein the slot terminates short of the second driver proximal end.

There may also be provided a system wherein the second driver defines a torque section between the second driver proximal end and the driving section, the torque section being more rigid in torsion and flexion than the driving section.

There may also be provided a system wherein the at least one protrusion includes a series of pegs longitudinally spaced apart from each other, each protruding from the first driver surface in the driver passageway.

There may also be provided a system wherein the at least one protrusion includes a helical protrusion protruding from the first driver surface in the driver passageway.

There may also be provided a system wherein the at least one protrusion includes a series of helical protrusions longitudinally spaced apart from each other and each protruding in the driver passageway from the first driver surface, the helical protrusions being separated longitudinally from each other by regions of the first driver surface devoid of protrusions protruding in the driver passageway.

There may also be provided a system wherein the first driver is the inner driver and the second driver is the outer driver, the anchor protrusion protruding radially outwardly relative to the anchor body.

There may also be provided a system further comprising an outer shell covering at least the driving section.

There may also be provided a system wherein the driver passageway is substantially annular.

There may also be provided a system wherein the inner driver is hollow.

There may also be provided a system wherein the inner driver protrudes distally relative to the outer driver.

In another broad aspect, there is provided a catheter segment, the catheter segment being hollow and defining substantially longitudinally opposed segment first and second ends, the catheter segment also defining opposed segment outer and inner surfaces, the catheter segment comprising: a slot region, at least one backbone region and intermediate regions extending between either adjacent backbone regions or between one of the backbone region and the slot region, each of the slot, backbone and intermediate regions extending between the segment first and second ends, the slot and backbone regions being all disjoint from each other, the slot region, at least one backbone region and intermediate regions being all distributed circumferentially around the driving section; the slot region including a slot extending therealong, the slot being narrower circumferentially than the slot region, the slot region defining opposed slot region first and second side edges; each backbone region defining respective opposed backbone region first and second side edges; the catheter segment further comprising a plurality of first slits and a plurality of second slits, each of the first and second slits extending between the segment inner and outer surfaces, the first and second slits being all disjoint from each other, each first slit extending around the catheter segment between the slot region first and second side edges and the second slits each extending between one of a backbone region first and second side edges and either a backbone region first or second side edges of an adjacent backbone region or the slot.

There may also be provided a catheter segment wherein the slot and backbone regions are substantially parallel to each other.

There may also be provided a catheter segment wherein the slot and backbone regions are substantially helical around the catheter segment.

There may also be provided a catheter segment wherein the second slits define slit groups including second slits in prolongation of each other around the catheter segment, each slit group defining an interrupted slit extending around the catheter segment and interrupted in the backbone regions.

There may also be provided a catheter segment wherein the first slits and the slit groups alternate longitudinally along the catheter segment.

There may also be provided a catheter segment wherein the first and second slits are each substantially circumferential.

There may also be provided a catheter segment wherein all the first slits are substantially parallel to each other.

There may also be provided a catheter segment wherein all the second slits are parallel to the first slits.

There may also be provided a catheter segment wherein all the first and second slits are all arc segment shaped with a center of rotation at a longitudinal axis of the catheter segment.

There may also be provided a catheter segment wherein the slot is helical.

There may also be provided a catheter segment wherein the driving section includes two backbone regions.

In another broad aspect, there is provided a surgical catheter including the catheter segment.

In another broad aspect, there is provided a system comprising: a helical anchor drivable into biological tissue, the helical anchor including a substantially helical anchor body defining anchor body proximal and distal ends and an anchor body passageway extending therethrough between the anchor body proximal and distal ends, the anchor body being being delimited inside a generally cylindrical shape, an anchor protrusion extending radially from the anchor body at the anchor body proximal end: substantially elongated inner and an outer drivers concentric relative to each other and defining a driver passageway therebetween, the helical anchor being mounted between the inner and outer drivers in the driver passageway, the inner driver defining longitudinally opposed inner driver proximal and distal ends and the outer driver defining longitudinally opposed outer driver proximal and distal ends, the inner and outer drivers being axially rotatable relative to each other and longitudinally substantially fixed relative to each other; a first driver selected from the inner and outer drivers defining a first driver surface facing the driver passageway and provided with at least one protrusion protruding in the driver passageway and engaging the helical anchor, the at least one protrusion preventing pure translation of the helical anchor along the first driver while allowing helical movements of the helical anchor relative to the first driver; a second driver selected from the inner and outer drivers and differing from the first driver including a driving section extending from a second driver distal end towards a second driver proximal end, the driving section being provided with a slot extending therealong from the second driver distal end towards the second driver proximal end, the slot receiving the anchor protrusion thereinto, the anchor protrusion being movable along the slot; and an actuator operatively coupled to the inner and outer drivers at the inner and outer driver proximal ends operable for selectively rotating the inner and outer driver relative to each other.

The various aspects that this system may have are similar to the characteristics mentioned hereinabove with respect to the system described starting at paragraph [0008].

Advantageously, the systems described hereinabove can, in some embodiments, deliver many helical anchors in succession, without being withdrawn from a patient.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the drawings:

FIG. 2C, in a side cross-sectional view midway therethrough, illustrates a portion of the actuator of FIG. 2A;

FIG. 8, in a perspective view, illustrates a helical anchor usable with the system of FIG. 1;

FIG. 8A, in a perspective view, illustrates an anchor locking surface part of the helical anchor of FIG. 8;

FIG. 9, in a perspective view, illustrates a piston part of the attachment shown in FIGS. 6 and 7;

FIG. 15A, in a side elevation view, illustrates an alternative embodiment of a distal portion usable in the system of FIG. 1, the distal portion including an attachment for attaching a helical anchor thereto, the attachment being shown in a locked position;

FIG. 15B, in a side elevation view, illustrates a helical anchor usable with the system of FIG. 15A FIG. 15C, in a front cross-sectional view along section line XV-C of FIG. 15A, illustrates the distal portion of FIG. 15A;

FIG. 15D, in a front cross-sectional view along section line XV-D of FIG. 15B, illustrates the helical anchor of FIG. 15B;

FIG. 29, in a side cross-sectional view, illustrates an inner driver part of the distal portion of FIG. 26;

FIG. 29A, in a side cross-sectional view, illustrates a ramp part of the inner driver of FIG. 29;

FIG. 29B, in a top elevation view, illustrates the ramp of FIG. 29A;

FIG. 30, in a perspective view, illustrates a step in the deployment of multiple helical anchors sequentially using the distal portion of FIG. 26;

FIG. 36B, in a side elevation view, illustrates part of the piston of FIG. 36A;

FIG. 39, in a perspective view, illustrates the piston and of FIG. 38 with a helical anchor mounted thereto;

FIG. 39A, in a perspective view, illustrates mounting of the helical anchor to the piston of FIG. 39;

FIG. 40, in a perspective view, illustrates an alternative distal portion usable in the system of FIG. 1 including the linking element of FIG. 37 and the piston of FIG. 38;

FIG. 41A, in a side cross-sectional view midway therethrough, illustrates an alternative inner driver usable in an alternative distal portion usable with a system similar to the system of FIG. 1;

FIG. 41B, in a side elevation view, illustrates the inner driver usable of FIG. 41A;

FIG. 42A, in a side cross-sectional view midway therethrough, illustrates an alternative outer driver usable with the inner driver of FIGS. 41A and 41B;

FIG. 42B, in a side elevation view, illustrates the outer driver of FIG. 42A;

FIG. 75, in a side elevation view, illustrates yet another manner of attaching an anchor in the system of FIG. 1 using inner and outer sleeves, the inner and outer sleeves being shown in a locked configuration;

FIG. 76, in a perspective view, illustrates the outer sleeve of FIG. 75;

FIG. 77, in a perspective view, illustrates the inner sleeve of FIG. 75;

FIG. 78, in a side elevation view, the inner and outer sleeves of FIG. 75 in a locked configuration;

FIG. 79, in a side elevation view, the inner and outer sleeves of FIG. 75 in the locked configuration with a helical anchor removed therefrom;

FIG. 80, in a front cross-sectional view, illustrates a slot in yet another outer driver;

FIG. 81, in a perspective view, illustrates yet another helical anchor;

FIG. 82, in a perspective view, illustrates an outer driver usable with the anchor of FIG. 81; and FIG. 83, in a perspective view, illustrates another outer driver usable with the anchor of FIG. 81.

DETAILED DESCRIPTION

Figure 1:
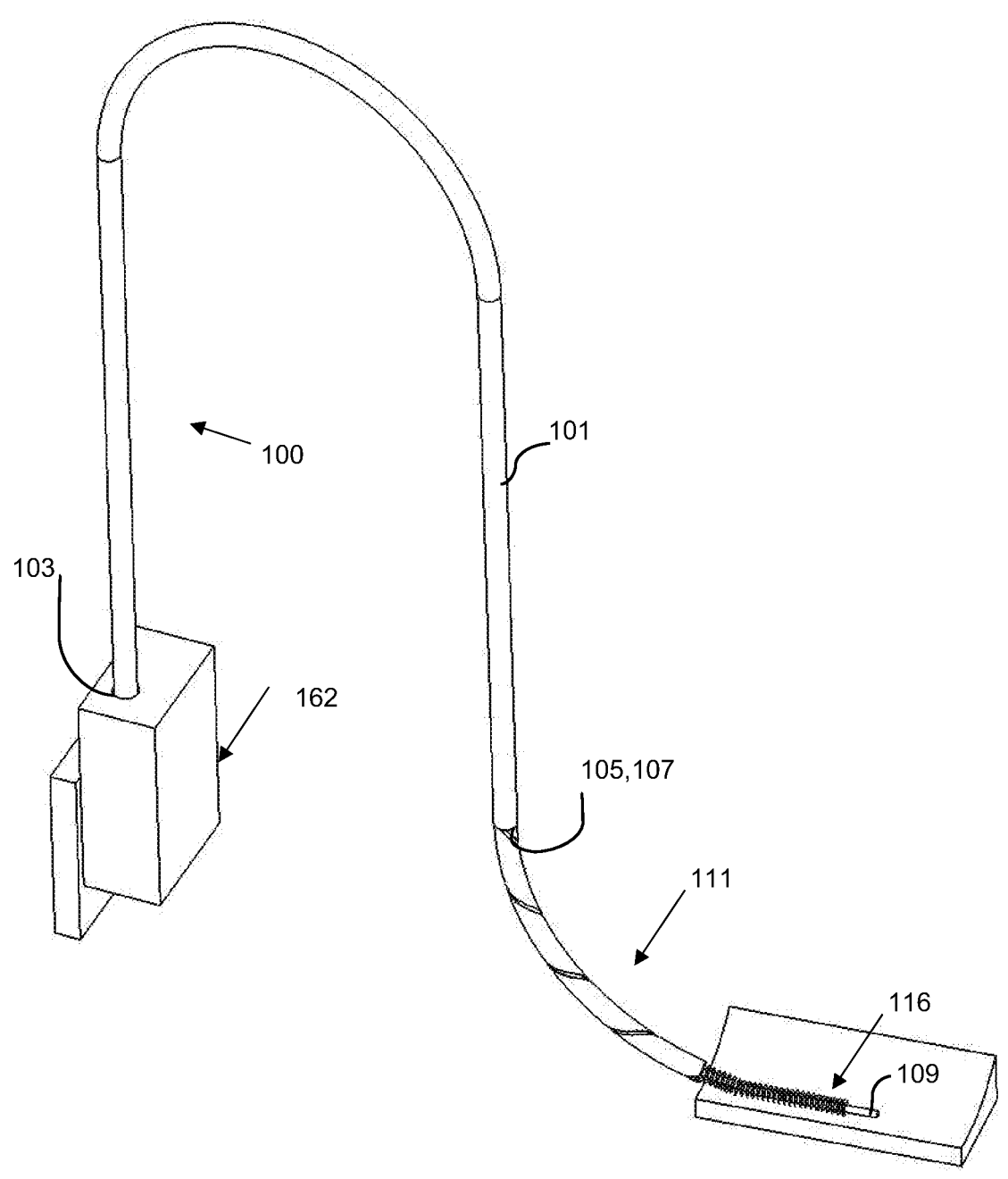
FIG. 1, in a schematic view, illustrates an embodiment of a helical anchor driving system.

FIG. 1 illustrates an embodiment of a helical anchor driving system 100. The system 100 is usable for driving a helical anchor 116, and other similar helical anchors 116.

The system 100 is particularly useful in surgical procedures that are performed with the hands of a surgeon away from the target biological tissue, for example through a laparoscopy, percutaneous or a transcatheter procedure. In this latter case, as see in FIG. 2, the system 100 is inserted through a substantially elongated catheter 101 defining substantially opposed catheter proximal and distal ends 103 and 105 and a catheter lumen 107 extending therebetween. A guide 109 protrudes from the catheter lumen 107 at the catheter distal end 105. However, the present invention may also be used without the catheter when easy access to the target biological tissue exists. In other embodiments, the guide 109 is not provided.

The system 100 is usable with the helical anchor 116. As better seen in FIG. 8, the helical anchor 116 defines a helical anchor longitudinal axis 118 and substantially longitudinally opposed helical anchor proximal and distal ends 120 and 122. A helical anchor passageway 124 extends longitudinally between the helical anchor proximal and distal ends 120 and 122. The guide 109 is positionable to be extending at least partially through the helical anchor 116 along the helical anchor longitudinal axis 118.

In the present document, the terminology distal and proximal refers to the location relative to an operator (not shown in the drawings) using the system 100. Distal elements are closer to the target biological tissue, while proximal elements are closer to the operator of the system 100. This terminology is used to facilitate the description of the system 100 and should not be used to restrict the scope of the present invention. Also, the terminology "substantially" and "about" is used to denote variations in the thus qualified terms that have no significant effect on the principle of operation of the system 100. These variations may be minor variations in design or variations due to mechanical tolerances in manufacturing and use of the system 100. These variations are to be seen with the eye of the reader skilled in the art.

In some embodiments, the helical anchor 116 has the same shape, or substantially the same shape, before and after insertion in the target biological tissue. In other words, the helical anchor 116 does not deform substantially during insertion. In other embodiments, the helical anchor 116 includes a shape memory material, for example Nitinol™ and changes between a helical anchor first configuration and a helical anchor second configuration at a transition temperature. For example, the transition temperature is between 20° C. and 37° C. In some embodiments, the helical anchor first and second configurations have different pitches. The pitch is defined in the present document as the longitudinal distance covered when advancing along the helical anchor 116 one full turn about the helical anchor longitudinal axis 118.

In some embodiments, as seen in FIG. 8, the pitch of the helical anchor 116 is constant along the whole helical anchor 116. In other embodiments (not shown in the drawings), the helical anchor 116 has a pitch that varies between the helical anchor proximal and distal ends 120 and 122. In such embodiments, the pitch may be larger at the helical anchor distal end 122 than at the helical anchor proximal end 120. This configuration provides a compression of the target biological tissue as the helical anchor 116 is advanced thereinto. In yet other embodiments, the diameter of the helical anchor 116 is not constant therealong. For example, a few coils closer to the anchor distal end 122 may be smaller than the remainder of the helical anchor 116. The helical anchor distal end 122 sharpness is varied depending on target biological tissue properties.

The helical anchor 116 may be metallic. The helical anchor 116 may be biodegradable. Also, in some embodiments, the helical anchor 116 may be provided with small tins on its surface or finishing that increases the friction with surrounding target biological tissue. In yet other embodiments, the helical anchor 116 is hollow.

The system 100 includes a distal portion 111 that is used to deliver the helical anchor 116. Various configurations of the distal portion 111 are described hereinbelow. In some embodiments, the distal portion 111 is configured to deliver a single helical anchor 116. In other embodiments, the distal portion 111 can deliver a series of helical anchors 116 without requiring withdrawal from the patient in which the helical anchors 116 are driven.

In a first embodiment, the distal portion 111 includes an attachment 160 (seen for example in FIGS. 6 and 7), provided for example at the catheter distal end. The system 100 also includes an actuator 162 (seen for example in FIGS. 1, 2A and 2B) and a linking element 134 (seen for example partially in FIGS. 6 and 7) extending therebetween. The helical anchor 116 is securable to the attachment 160. The actuator 162 is the part of the system 100 that is handled by a surgeon or any other suitable operator while the system 100 is use to implant the helical anchor 116. The linking element 134 extends between the actuator 162 and the attachment 160 and transmits movements of the actuator 162 to the attachment 160. Typically, the actuator 162 can be moved longitudinally, to advance or retract the attachment 160, and/or rotated, to rotate the attachment 160. The linking element 134 is typically sufficiently rigid to efficiently transmit longitudinal forces and torques about the helical anchor longitudinal axis 118. In some embodiments, the actuator 162 is also operative for selectively detaching the helical anchor from the attachment 160. If the actuator 162 is not operated to intentionally perform this detachment, the helical anchor 116 remains secured to the attachment 160.

The attachment 160, linking element 134 and actuator 162 are typically hollow and define a system passageway 102 through which the guide 109. However, in other embodiments, the system passageway 102 is omitted.

In some embodiments, the actuator 162 is operative for selectively simultaneously rotating the helical anchor 116 along the helical anchor longitudinal axis 118 and advancing the helical anchor 116 along the helical anchor longitudinal axis 118 in a distally oriented direction. In some embodiments, the actuator 162 is configured so that the helical anchor 116 is actively advanced while rotated. In other embodiments, the actuator 162 is simply free to move longitudinally and is advanced by the helical anchor 116 as the latter advances in the target biological tissue due to rotation of the helical anchor 116.

Figure 6:
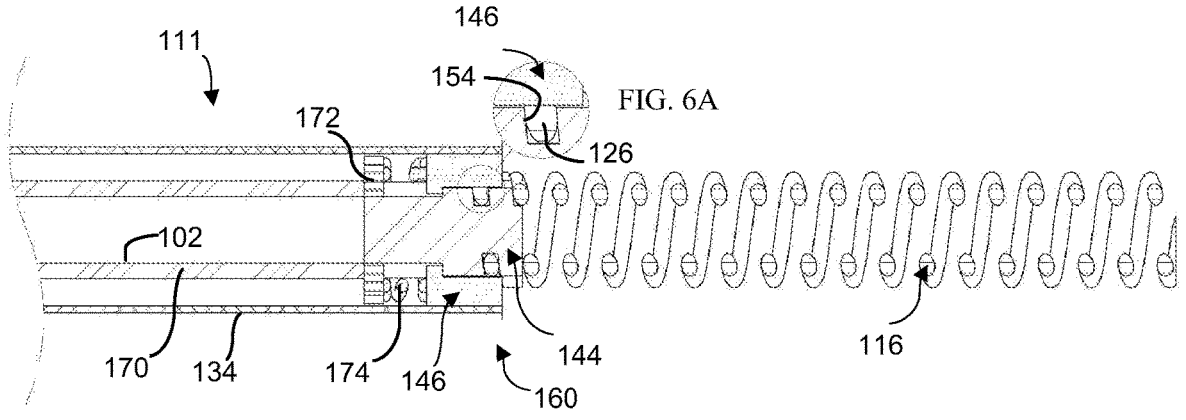
FIG. 6A, in a side cross-sectional view, illustrates mating between the anchor locking surface of FIG. 8A and the sleeve of FIG. 10.
Figure 7:
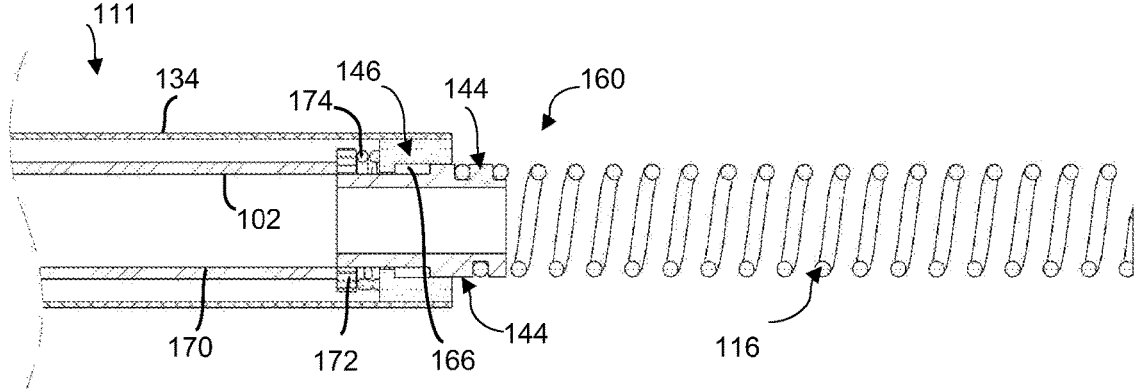
FIG. 7, in a side cross-sectional view midway therethrough, illustrates the distal portion of the system of FIG. 1 with the attachment being shown in a released position.

The specific embodiment of the attachment 160 shown in FIGS. 6 and 7 is now described in greater details. The attachment 160 includes a piston 144 and a sleeve 146 movable substantially longitudinally relative to each other between a locked position, seen in FIG. 6, and a released position, seen in FIG. 7. The helical anchor 116 is mountable to the piston 144. In the locked position, the helical anchor 116 is prevented from being released from the piston 144. In the released position, the helical anchor 116 can be selectively removed from the piston 144.

The piston 144 is better seen in FIG. 9. The piston 144 defines piston proximal and distal portions 148 and 150, the latter having a larger diameter than the former. A piston passageway 152 extends longitudinally through the piston 144. The piston distal portion 150 defines an external thread 154 having pitch and diameter similar to the pitch and diameter of the helical anchor 116 so that the latter can be screwed thereonto. The piston distal portion 150 terminates proximally by a ledge 156 extending generally radially, and therefore extends radially to a greater extent than the piston proximal portion 148. The piston distal portion 150 is typically generally cylindrical but is truncated axially so as to define a generally flat piston coupling surface 158 extending longitudinally, parallel to the longitudinal axis of the piston 144. The piston coupling surface 158 is retracted radially relative to the surface of a cylinder having the general shape of the remainder of the piston distal portion 150. The piston proximal portion 148 is also typically substantially cylindrical.

As seen in FIGS. 8 and 8A, the helical anchor 116 defines an anchor locking surface 126 adjacent to the helical anchor proximal end 120. The anchor locking surface 126 is configured to be substantially flush and continuous with the piston coupling surface 158 when the helical anchor 116 is secured to the piston 144. If the anchor locking surface 126 were not defined in the generally helically formed wire defining the helical anchor 116, the helical anchor 116 would protrude from the anchor locking surface 126 when mounted to the piston 144.

Figure 10:
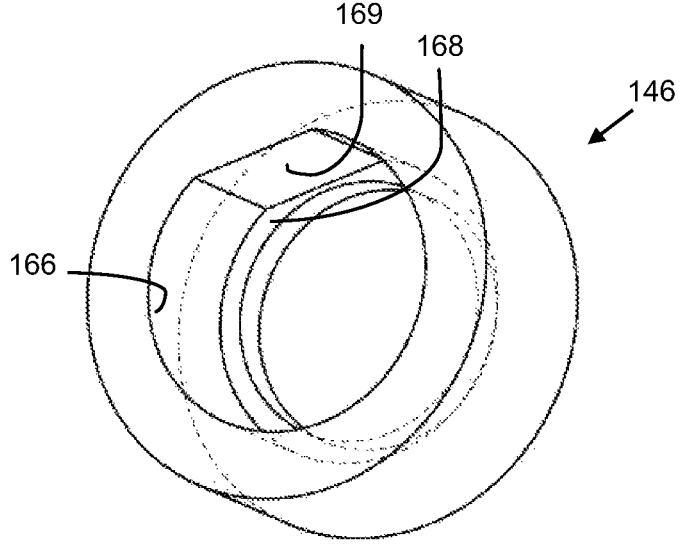
FIG. 10, in a perspective view, illustrates a sleeve part of the attachment shown in FIGS. 6 and 7.
Figure 11:
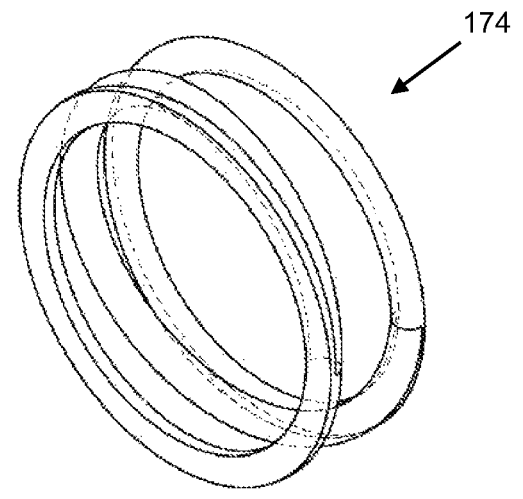
FIG. 11, in a perspective view, illustrates a biasing element part of the distal portion of FIG. 3A.

FIG. 10 illustrates the sleeve 146. The sleeve 146 is generally cylindrical and defines a sleeve passageway 166 extending longitudinally therethrough. The sleeve passageway 166 is of generally cylindrical transversal cross-section and defines a sleeve flange 168 extending radially inwardly at its proximal end, reducing the diameter of the sleeve passageway 166. The diameter of the sleeve passageway 166 at the sleeve flange 168 is substantially similar to the diameter of the piston proximal portion 148, which is received therethrough. The sleeve passageway 166 also defines a substantially flat sleeve coupling surface 169. The sleeve passageway 166 at the sleeve coupling surface 169 has a transversal cross-sectional configuration substantially similar to the transversal cross-sectional configuration of the piston distal portion 150 and receives the latter therethrough so the piston distal portion 150 protrudes distally from the sleeve 146. Due to the parallel sleeve coupling surface 169 and piston coupling surface 158, the piston 144 and sleeve 146 do not rotate relative to each other.

As seen in FIG. 6, in the locked position, the anchor locking surface 126 is inside the sleeve 146 and the helical anchor 116 is prevented from rotating about the external thread 154. In the released position, as seen in FIG. 7, the piston 144 is positioned distally with respect to the sleeve 146 relative to the locked position so that the helical anchor 116 is outside of the sleeve passageway 166. This is achieved by either withdrawing proximally the sleeve 146 relative to the piston 144, as in the system 100, or by pushing the piston 144 distally relative to the sleeve 146. In this configuration, the helical anchor 116 can be removed from the piston 144 by unscrewing the piston 144 and helical anchor 116 from each other.

The sleeve 146 is secured to the distal end of the linking element 134, for example using an adhesive or through welding. Rotating the linking element 134 therefore allows the intended user of the system 100 to rotate the helical anchor 116. The system 100 also includes a piston actuating element 170, typically hollow, extending through the linking element 134 to reach the actuator 162. The piston actuating element 170 is terminated distally by a radially outwardly extending piston actuating element flange 172 and the piston 144 is mounted at its proximal end to the distal end of the piston actuating element 170. A biasing element 174, for example a coil spring, or any other suitable spring, extends between the sleeve 146 and the piston actuating element flange 172 and biases the piston 144 towards the locked position. In some embodiments, the biasing element 174 is omitted.

Movements of the piston 144 in the sleeve 146 are therefore limited proximally by abutment of the ledge 156 against the sleeve flange 168, and distally by contact between the piston actuating element flange 172, the biasing element 174 and the sleeve 146.

Figure 2A:
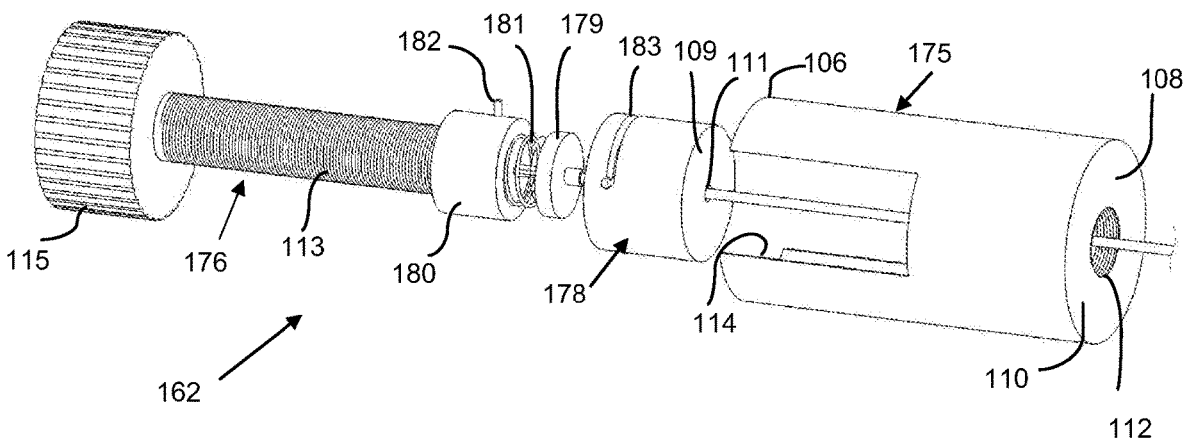
FIG. 2A, in a perspective exploded view, illustrates an actuator part of the system of FIG. 1.
Figure 2B:
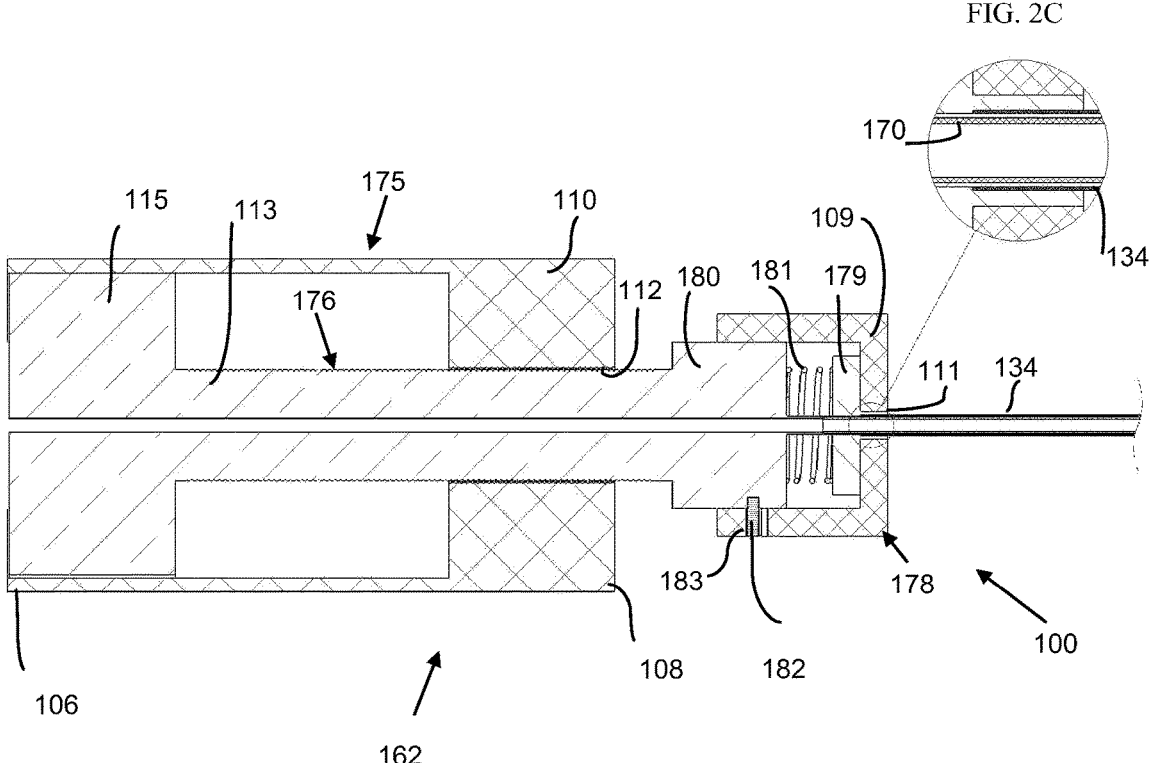
FIG. 2B, in a side cross-sectional view midway therethrough, illustrates the actuator of FIG. 2A.

FIGS. 2A and 2B illustrate an exemplary embodiment of an actuator 162. The actuator 162 includes an actuator body 175, a driving element 176 and a piston actuating element controller 178. In some embodiments, a washer 179 and/or an actuator biasing element 181 are provided. However, in other embodiments, the washer 179 and actuator biasing element 181 are omitted. Typically, the components that connect the actuator 162 to the distal elements, such as the piston 144 and 146, are selected so that they don't elongate relative to each other in use.

Referring to FIG. 2A, the actuator body 175 is generally cylindrical and tubular and defines substantially longitudinally opposed actuator body proximal and distal ends 106 and 108. A radially inwardly extending actuator body flange 110 provided at the actuator body distal end 108 defines an axially extending threaded aperture 112. One or more recesses 114 extend longitudinally in the actuator body 175 from the actuator body proximal end 106 and provide access to the interior of the actuator body 175 radially from the outside.

The driving element 176 defines a proximal end knob 115 of a diameter substantially similar to the internal diameter of the actuator body 175 at the actuator body proximal end 106, and a threaded shaft 113 extending distally therefrom. The threaded shaft 113 threadedly engages the threaded aperture 112 and protrudes distally therefrom. The proximal end knob 115 is in register with the recess 114. The threaded shaft 113 is distally terminated by a radially outwardly extending shaft flange 180, provided outside of the actuator body 175, from which a pin 182 extends radially outwardly.

Figure 4:
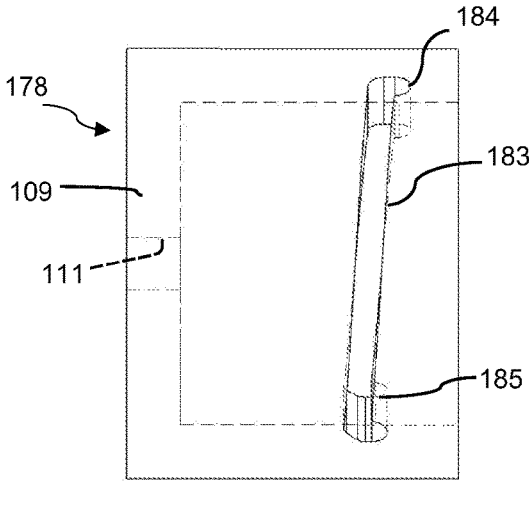
FIG. 4, in a side elevation view, illustrates a piston actuating element controller part of the actuator of FIGS. 2A and 2B FIG. 5, in a side elevation view, illustrates an alternative piston actuating element controller usable in the actuator of FIGS. 2A and 2B FIG. 6, in a side cross-sectional view midway therethrough, illustrates a distal portion of the system of FIG. 1, the distal portion including an attachment for attaching a helical anchor thereto, the attachment being shown in a locked position.

Referring for example to FIG. 4, the piston actuating element controller 178 is also generally cylindrical and tubular and is terminated distally by a distal end wall 109 defining an axial end wall aperture 111 extending therethrough. The piston actuating element controller 178 defines a control slot 183 in its peripheral surface receiving the pin 182 (not shown in FIG. 4) radially therethrough. The control slot 183 defines control slot proximal and distal ends 184 and 185 circumferentially spaced apart from each other. The pin 182 is movable along the control slot 183 between the control slot proximal and distal ends 184 and 185. In some embodiments, the control slot 183 is terminated at the control slot proximal and distal ends 184 and 185 by proximally extending portions that provide a locking action under the action of the actuator biasing element 181 maintaining the pin 182 in one of the control slot proximal and distal ends 184 and 185. The piston actuating element controller 178 receives the shaft flange 180 and is movable relative thereto.

Referring to FIG. 2B, when provided, the washer 179 and actuator biasing element 181 are in the piston actuating element controller 178 between the shaft flange 180 and distal end wall 109, the washer 179 being distal relative to the actuator biasing element 181. The actuator biasing element 181 is for example a coil spring or a wave spring and biases the shaft flange 180 and distal end wall 109 away from each other.

The linking element 134 is fixedly secured to the piston actuating element controller 178 at the end wall aperture 111. The piston actuating element 170 is fixedly secured to the threaded shaft 113.

In use, rotating the end knob 115 advances and retreats the threaded shaft 113 in the threaded aperture 112, resulting in simultaneous advancement and retraction of the helical anchor 116 while rotating the latter. To detach the helical anchor 116, the piston actuating element 170 is rotated to transfer the pin 182 from the control slot proximal end 184 to the control slot distal end 185, which retracts the sleeve 146 relative to the piston 144.

Figure 5:
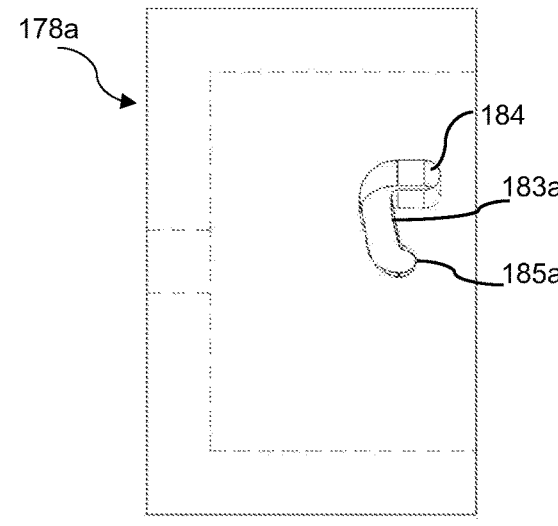

As seen in FIG. 5, in alternative embodiments of the piston actuating element controller 178a, the control slot 183a may be relatively small in circumferential extension and have a generally J-shaped configuration. In this embodiment, passage of the pin 182 between the control slot proximal end 184a and the control slot distal end 185b involves a longitudinal movement of the piston actuating element 170 in addition to a small rotation, relative the threaded shaft 113.

Figures 12, 13, 13A, 14:
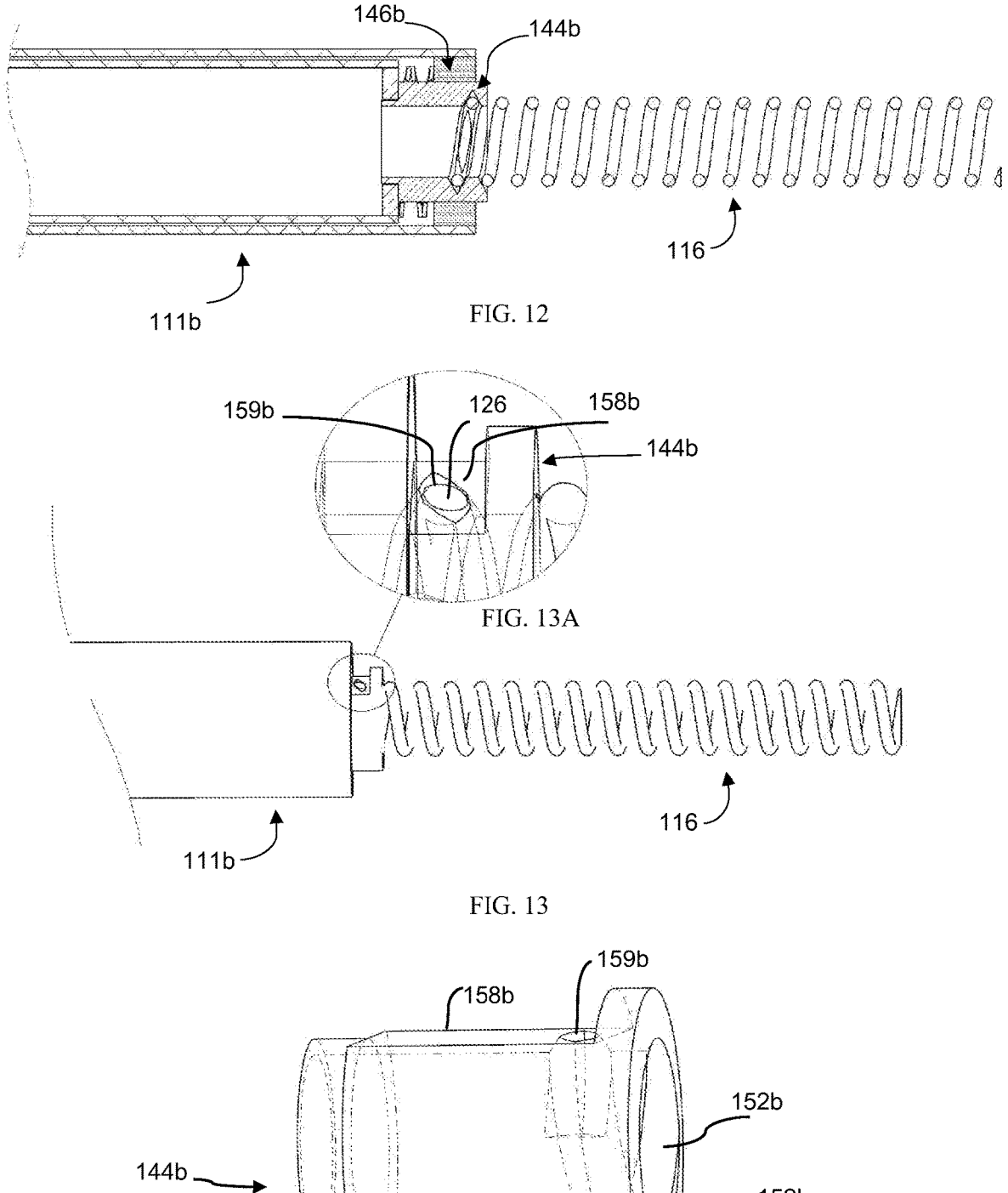
FIG. 12, in a side cross-sectional view midway therethrough, illustrates an alternative embodiment of a distal portion usable in the system of FIG. 1, the distal portion including an attachment for attaching a helical anchor thereto, the attachment being shown in a locked position.
FIG. 13, in a side elevation view, illustrates the distal portion of FIG. 12 with the attachment being shown in a released position.
FIG. 13A, in a side elevation view, illustrates part of the distal portion of FIG. 12.
FIG. 14, in a perspective view, illustrates a piston part of the attachment shown in FIGS. 13 and 14.

FIGS. 12 to 14 illustrate a variant of the distal portion 111, distal portion 111b usable in the system 100. The distal portion 111b is similar to the distal portion 111 and operates using similar principles Notably, the actuator 162 is used to operate the distal portion 111b. However, the piston 144b of the distal portion 111b differs from the piston 144 in that is is internally threaded, and not externally threaded like the piston 144. More specifically, referring to FIG. 14, the piston 144b is hollow and defines an internal thread 154b in the peripheral surface of the piston passageway 152b. The internal thread 154b intersects the piston coupling surface 158b so that an aperture 159b leads into the internal thread 154b from the piston coupling surface 158b. As seen in FIG. 13A, when the helical anchor 116 is attached to the piston 144b, the anchor locking surface 126 is in register with the aperture 159b and extends continuously and coplanarly with the piston coupling surface 158b. Other than this difference, the remainder of the distal portion 111b is similar to the system 100 and operates in a similar manner.

FIG. 15A illustrates another distal portion 111c usable to implant the helical anchor 116c. As in the distal portion 111b, a hollow piston 144c defining an internal thread 154c is used. However, instead of using interference between a sleeve 146 and the helical anchor 116, the helical anchor 116c interferes with a wire 146c that can be selectively moved back and forth through a wire passageway 147c extending substantially parallel to the sleeve passageway 152c. In opposition to the pistons 144 and 144b, the piston 144c does not define the piston coupling surface 158 and is substantially cylindrical. The sleeve 146 can thus be omitted. The internal thread 154c intersects the wire passageway 147c. As seen for example in FIGS. 15B and 15C, a notch 126c is defined in the helical anchor 116c. When the wire 146c is fully inserted distally in the wire passageway 147c and the helical anchor 116c is received in the internal thread 154c, the wire 146c engages the notch 126c and prevents rotation of the helical anchor 116c relative to the internal thread 154c. When the wire 146c is retracted so as to disengage from the notch 126c, the helical anchor 116c can rotate relative to the internal thread 154c and disengage therefrom.

In some embodiments, the wire 146c can slide longitudinally freely in the wire passageway 147c. In other embodiment, the wire 146c is threaded at its distal end, and the wire passageway 147c is complementarily threaded at its distal end so that one needs to rotate the wire 146c to withdraw the latter from the notch 126c.

Figure 55:
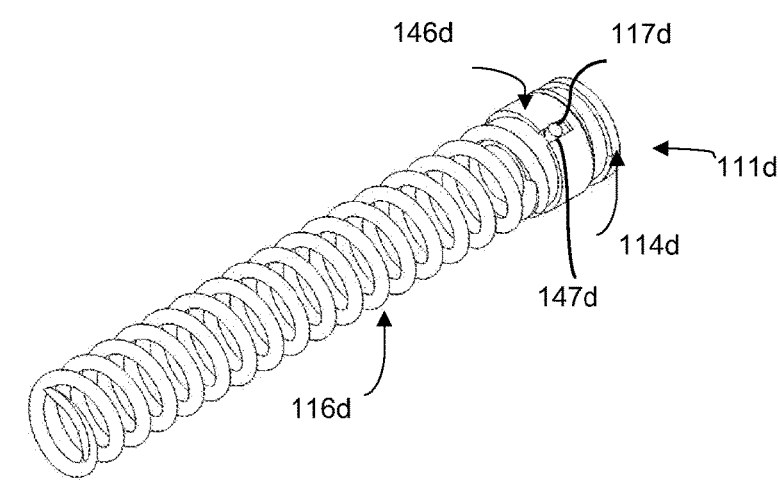
FIG. 55, in a perspective view, illustrates an alternative distal portion usable in the system of FIG. 1, here shown in a locked configuration.
Figure 56:
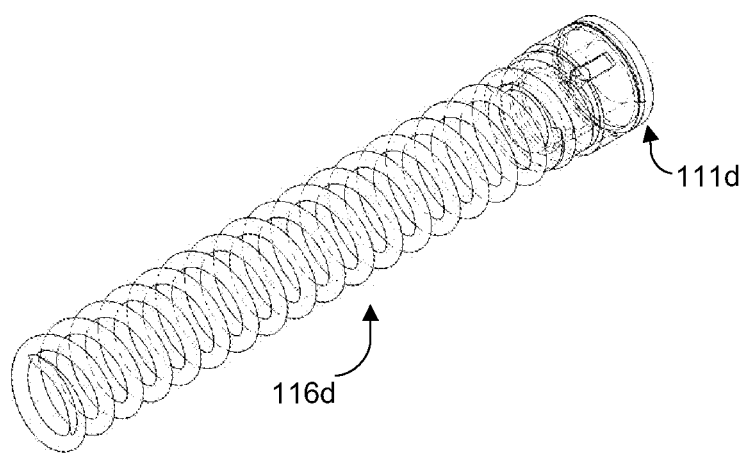
FIG. 56, in a perspective view, illustrates the distal portion of FIG. 55 in a released configuration.
Figure 57:
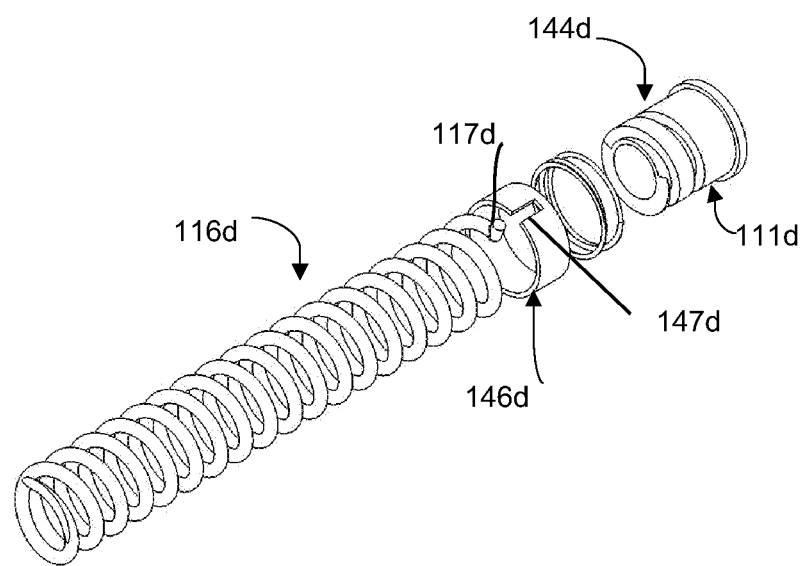
FIG. 57, in a perspective exploded view, illustrates the distal portion of FIG. 55.

FIGS. 55 to 57 illustrate respectively in a locked configuration, released configuration and exploded view yet another distal portion 111d usable in the system 100, system 100d. The actuator 162 is usable with in the distal portion 111d. However, the piston 144d of the system 100d has a completely cylindrical symmetry in that the piston coupling surface 158 is omitted. Instead, the helical anchor 116d defines a radially outwardly extending pin 117d at its proximal end. The sleeve 146d defines a longitudinal slot 147d extending from its distal end for receiving the pin 117d thereinto. When the piston 144d is retracted, in the locked configuration, the pin 117d is engaged in the slot 147d and the helical anchor 116d is locked to the piston 144d. Fully withdrawing the sleeve 144d from the piston 144d withdraws the slot 147d from the pin 117d longitudinally and proximally, which allows unscrewing the helical anchor 116d from the piston 144d. Other than these differences, the remainder of the system 100d is similar to the system 100 and operates in a similar manner.

Figure 3A:
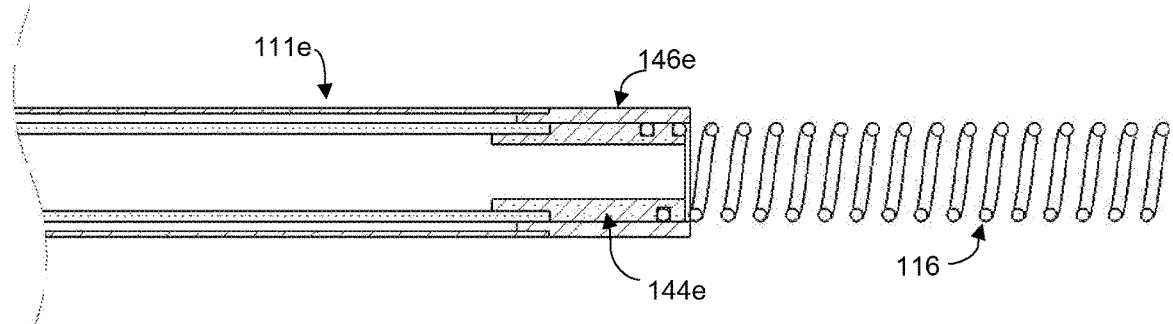
FIG. 3A, in a side cross-sectional view midway therethrough, illustrates an alternative distal portion usable in the system of FIG. 1, here shown in a locked configuration.
Figure 3B:
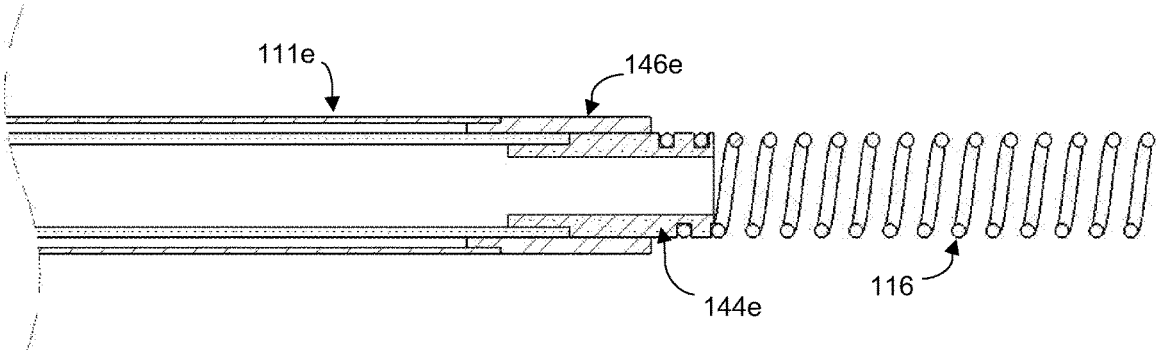
FIG. 3B, in a side cross-sectional view midway therethrough, illustrates the distal portion of FIG. 3A in a released configuration.

FIGS. 3A and 3B, in locked and released configurations respectively illustrate yet another distal portion 111e usable in the system 100. The piston 144e and sleeve 146e work similarly to the way the piston 144 and sleeve 146 work, except that there is no biasing element linking the piston 144 and sleeve 146 to each other.

Figure 36A:
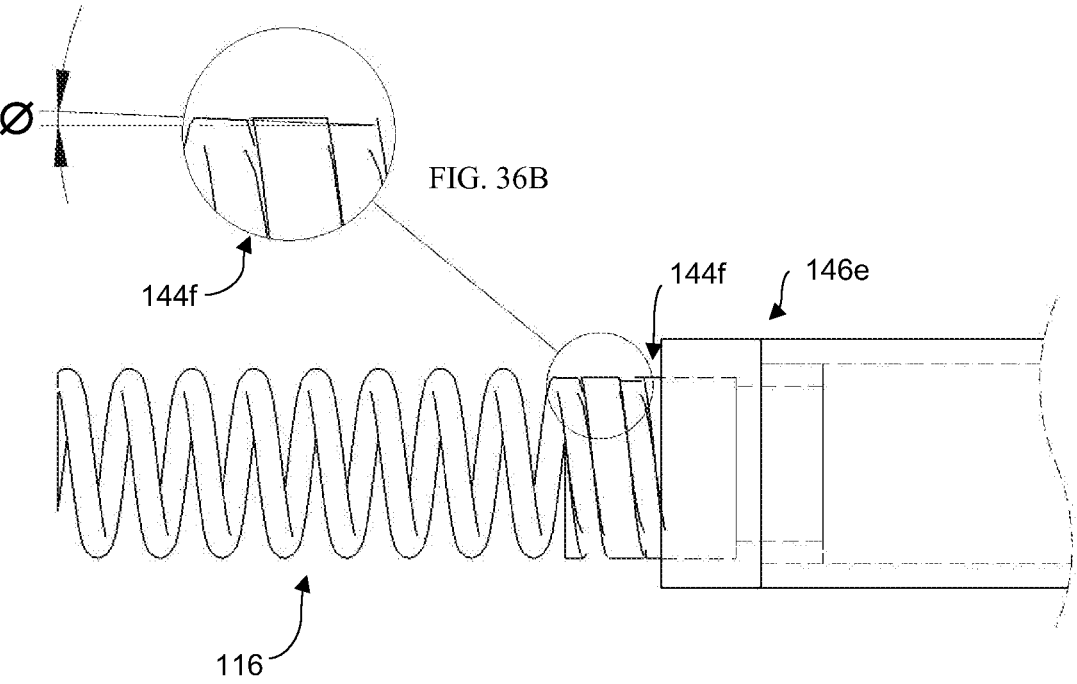
FIG. 36A, in a side elevation view, illustrates an alternative piston usable in the distal portion of FIG. 3A.

As seen in FIGS. 36A and 36B, in some embodiments, the piston 144f may be slightly tapered in a direction leading distally with an angle θ relative to a line parallel to the longitudinal axis of the piston 144f. For example, and non-limitingly, θ is about 2.5°.

Figure 37:
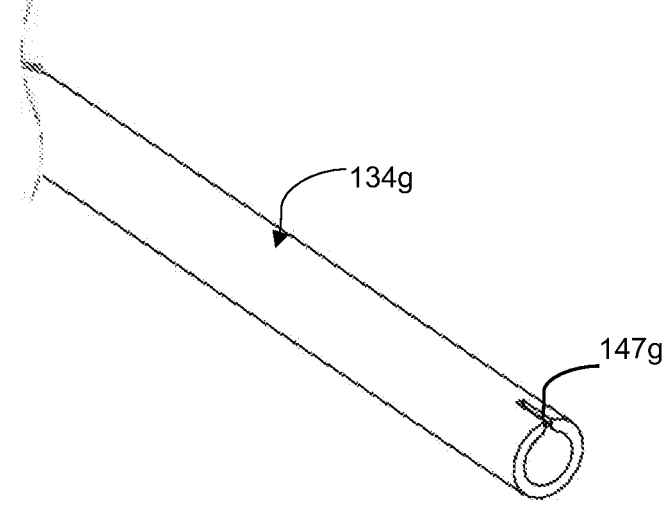
FIG. 37, in a perspective view, illustrates an alternative linking element usable of an alternative distal portion usable in the system of FIG. 1.
Figure 38:
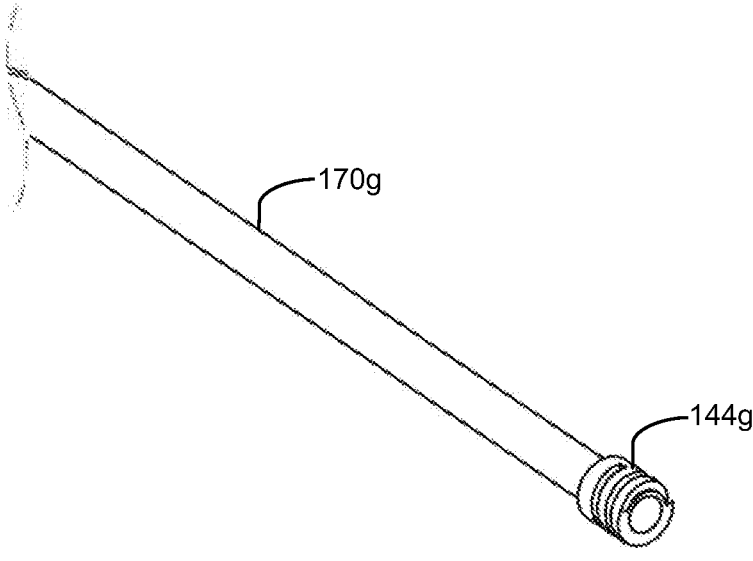
FIG. 38, in a perspective view, illustrates an alternative piston and an alternative piston linking element usable of an alternative distal portion usable in the system of FIG. 1.

Referring to FIG. 40, in some embodiments similarly to the distal portion 111d shown in FIGS. 55 to 57, a distal portion 111g omits the sleeve 146d. Instead, as seen in FIG. 37, the linking element 134g defines a slot 147g, similar to the slot 147d at its distal end. Also, the piston 144g is formed integrally at the distal end of the piston actuating element 170g. Also, the biasing element between the piston 144d and the sleeve 146d is omitted, similarly to the system 100e. Otherwise, the distal portion 111g works similarly to the distal portion 111d.

FIGS. 16 to 25 illustrate various aspects of a distal portion 211 in accordance with a second embodiment of the present invention, along with some variants thereof. The distal portion 211, seen in FIG. 16 for example, is usable to implant more than one helical anchor 216 one after the other. The distal portion 211 must be able to advance each helical anchor 216 to the implantation location, to rotate each helical anchor 216 to drive the helical anchor 216 in to the tissue and to release the helical anchor 216 so that the next helical anchor 216 can be suitably positioned. The helical anchors 216 are similar to the helical anchors 116 described hereinabove.

Figure 16:
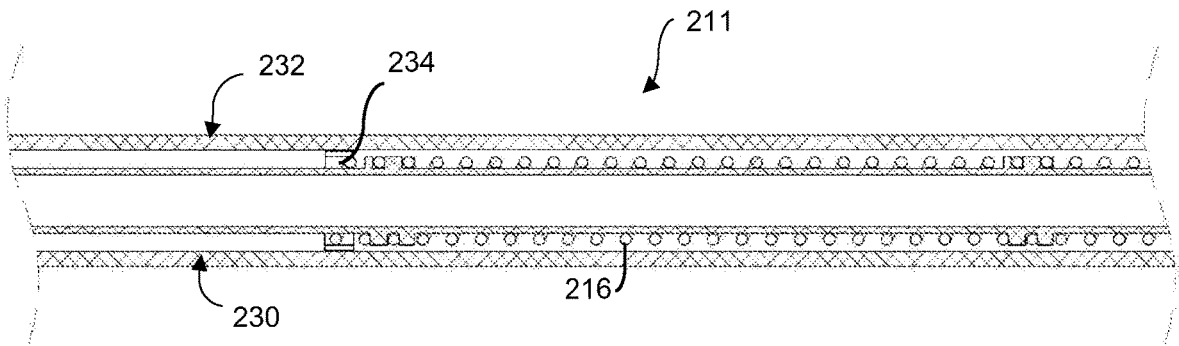
FIG. 16, in a side cross-sectional view midway therethrough, illustrates an alternative distal portion usable in a system similar to the system of FIG. 1.

The distal portion 211 includes an internal drive mechanism in which the helical anchors 216 are advanced over an inner driver 230. As seen in FIG. 16, an outer driver 232 surrounds the helical anchor 216 and is longitudinally fixed relative to the inner driver 230. The inner driver 230 can however be rotated along its longitudinal axis relative to the outer driver 232. The helical anchors 216 are each secured proximally to a respective anchor support 234. Rotating the inner driver 230 relative to the outer driver 232 moves the helical anchor 216 longitudinally, without rotation, along the inner and outer drivers 232 and 234. Rotating jointly the inner and outer drivers 230 and 232 rotates the helical anchor 216 without advancing the latter therealong. The anchor support 234 maintains the orientation of the helical anchor 216 relative to the outer driver 234. More than one helical anchor 216 can be mounted serially along the inner and outer drivers 230 and 232.

Figure 21:
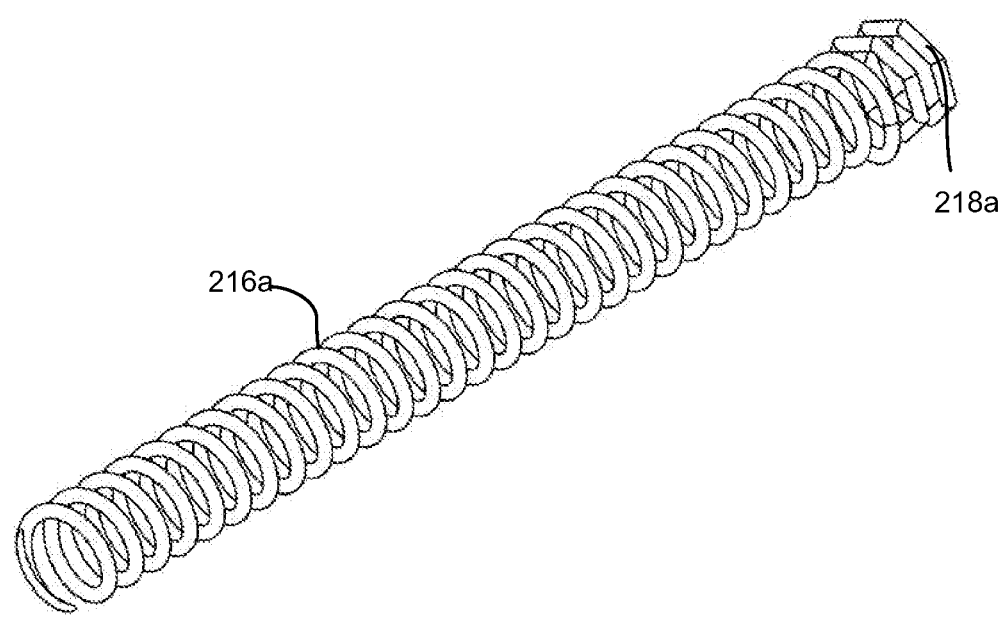
FIG. 21, in a perspective view, illustrates an alternative helical anchor usable in the distal portion of FIG. 16.

In some embodiments, the anchor support 234 is omitted and a suitable helical anchor 216a, shown in FIG. 21 is used instead. The helical anchor 216a is similar to the helical anchor 116 except that is it terminated proximally by a mounting portion 218a. The mounting portion 218a has a shape and pitch similar to the remainder of the helical anchor 216a, except that is has a generally hexagonal transversal configuration, as opposed to a generally circular configuration for the remainder of the helical anchor 216a. It should be noted that other polygonal configurations, such as square or octagonal configurations, among others, or other non-circular configurations, are within the scope of the invention for the mounting portion 218. The configuration of the mounting portion 218 matches the configuration of the anchor support 234.

Figure 20:
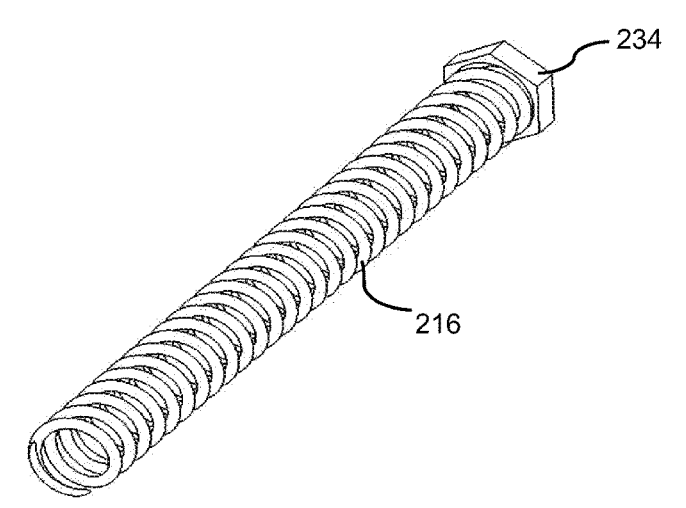
FIG. 20, in a perspective view, illustrates a helical anchor secured to an anchor support, both usable in the distal portion of FIG. 16.

As seen in FIG. 20, in other embodiments, the mounting portion 218a is replaced by an anchor support 234, which is generally annular with a substantially hexagonal configuration on the outside and a generally circular configuration on the inside. The anchor support 234 supports the remainder of the helical anchor 216. As with the mounting portion 218, other configurations of the anchor support 234 are within the scope of the invention. The anchor support 234 is permanently secured to the helical anchor 216 and remains in the patient once the helical anchor 216 is implanted. The anchor support 234 and/or the mounting portion 218 may be bioresorbable or not bioresorbable.

Figure 22:
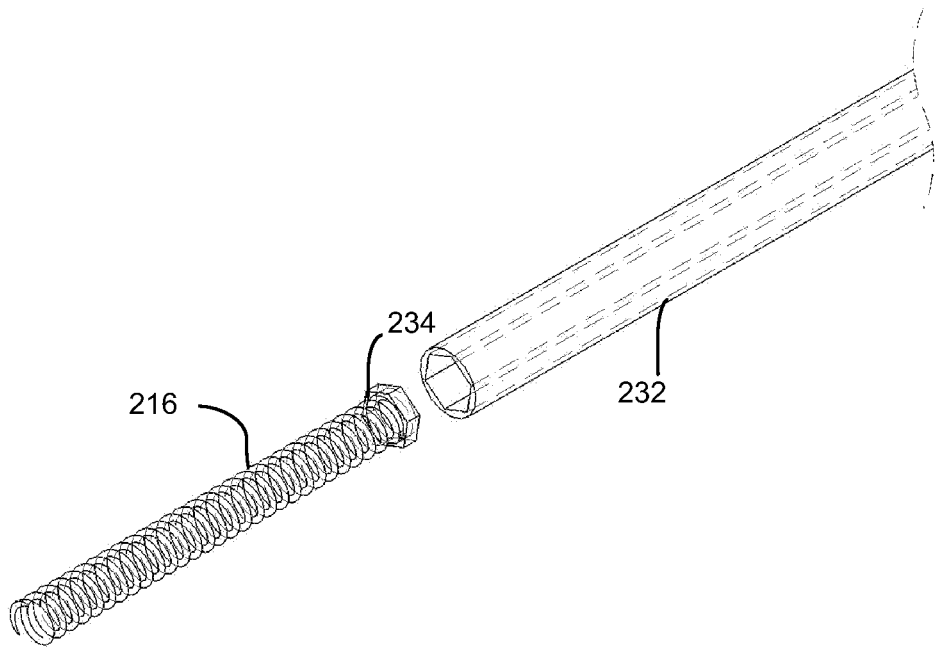
FIG. 22, in a perspective view, illustrates an outer driver part of the distal portion of FIG. 16.

As seen in FIG. 22, the outer driver 232 is tubular with an inside configuration that is substantially hexagonal and substantially snugly fitting to the hexagonal configuration of the anchor support 234. The external configuration of the outer driver is substantially circular. If the anchor support 234 has another external configuration, the internal configuration of the anchor support 234 is adapted accordingly so that the anchor support 234 can advance and retract longitudinally along the outer driver 232, but cannot rotate relative thereto. The outer driver 232 is sufficiently rigid in rotation to allow transmission of torque to the helical anchor 216 from the proximal end of the outer driver 232.

Figure 17:
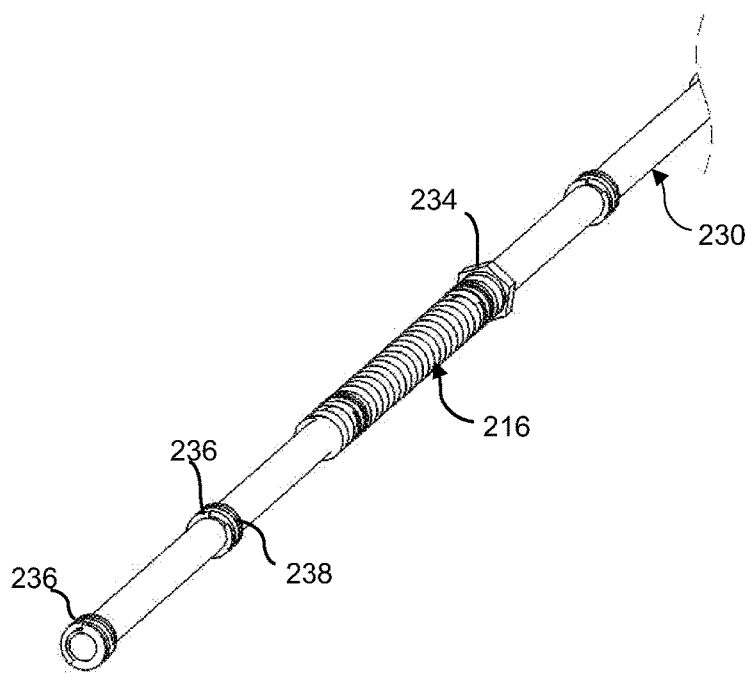
FIG. 17, in a perspective view, illustrates an inner driver part of the distal portion of FIG. 16.

Referring to FIG. 17, the inner driver 230 is generally tubular with a circular outside configuration. The inner driver 230 may be hollow to allow passage of a guide therethrough, as described with respect to the system 100. The inner driver 230 defines a plurality of driving sections 236 at longitudinally spaced apart locations therealong. Each driving section defines a thread 238 having generally the same dimensions and configurations as the helical anchor 216. The driving sections 236 are separated from each other by a distance that is at least slightly smaller than the length of the helical anchor 216 so that at all times while the helical anchors 216 are advanced along the inner driver 230, they are engaged with at least one of the driving sections 236. The whole inner driver 230 may alternatively be threaded. However, it may be advantageous in some embodiments to have distinct driving sections 236 to minimize frictions. The inner driver 230 is sufficiently rigid in rotation to allow transmission of torque to driving sections 236 from its proximal end.

Figure 18:
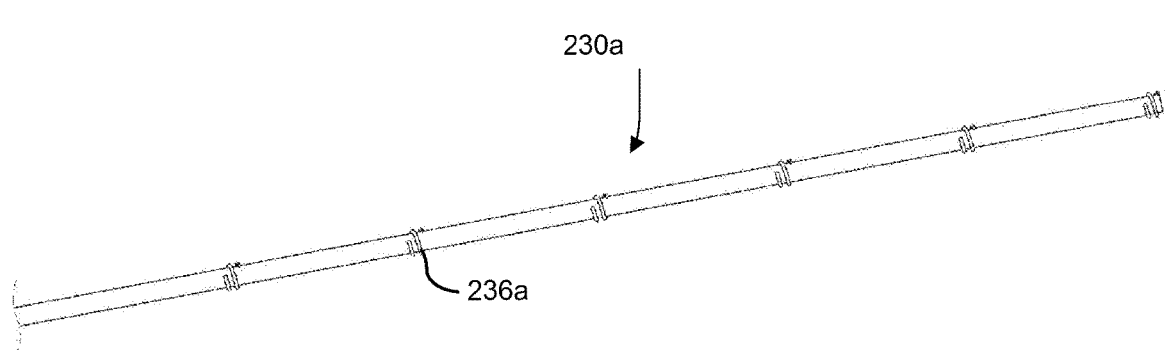
FIG. 18, in a perspective view, illustrates an alternative inner driver usable in the distal portion of FIG. 16.
Figure 19:
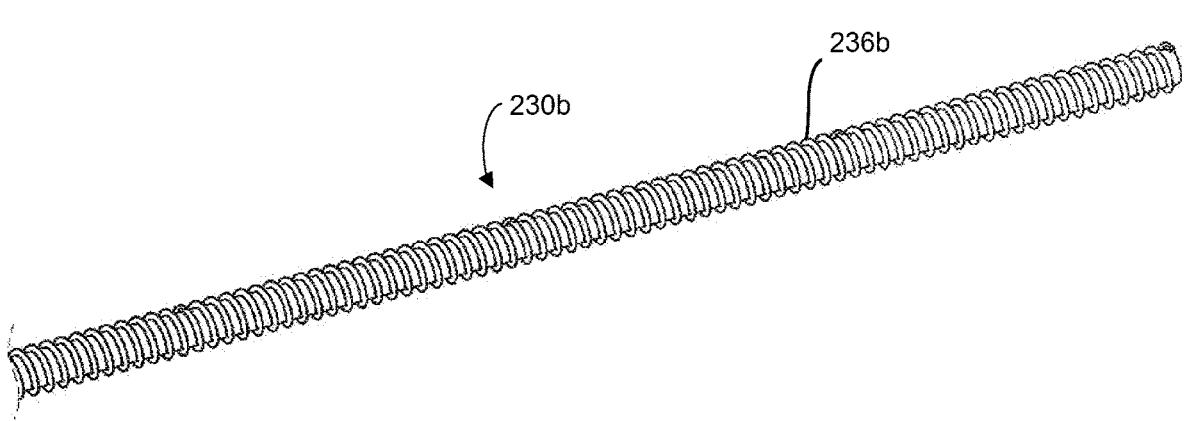
FIG. 19, in a perspective view, illustrates an other alternative inner driver usable in the distal portion of FIG. 16.

FIG. 18 illustrates an alternative inner driver 230a usable to replace the inner driver 230. The inner driver 230a includes alternative driving sections 236a that are formed by helical sections protruding from the remainder of the inner driver 230. The driving sections 236a have pitch and diameter similar to the pitch and diameter of the helical anchor 216. As seen in FIG. 19, in yet another inner driver 230b, the driving sections 236a are replaced by a long helical protrusion 236b matching the configuration of the helical anchors 216.

Figure 49:
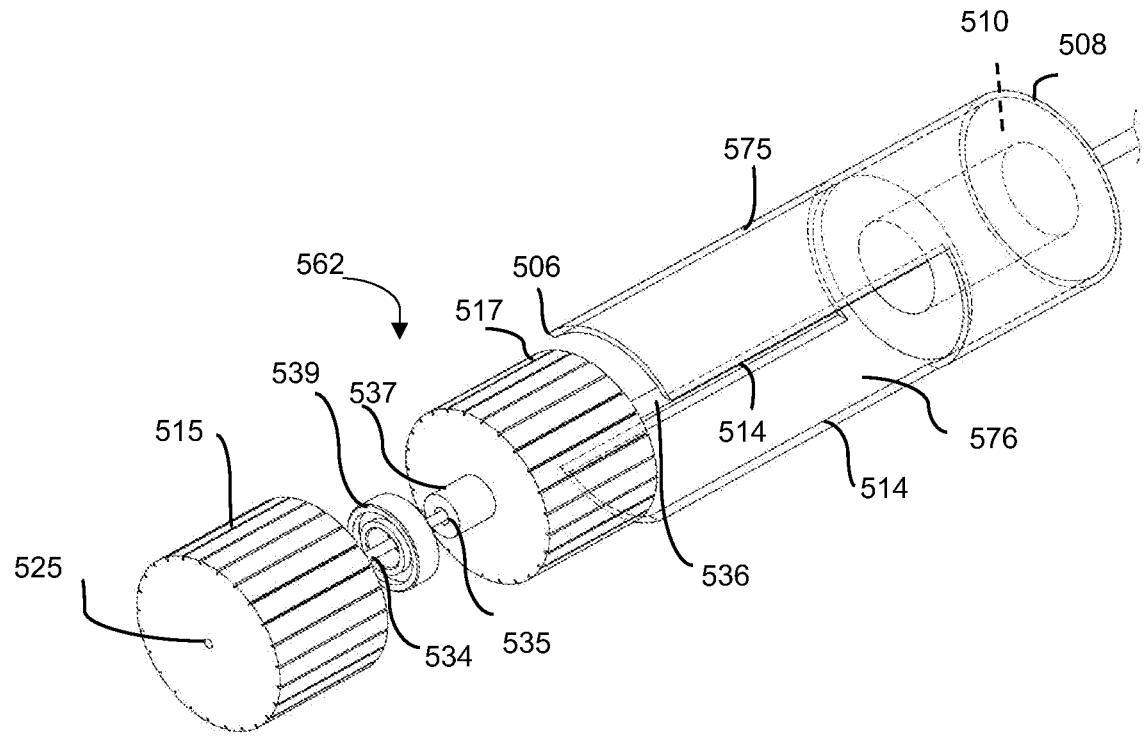
FIG. 49, in a perspective exploded view, illustrates an alternative actuator.

The inner drivers 230, 230a and 230b and the outer driver 232 can be rotated relative to each other in any suitable manner. FIG. 49 illustrates a suitable actuator 562 that can be used to that effect and is described in further details hereinbelow. In alternative embodiments, the inner drivers 230, 230a and 230b are polygonal and the interior surface of the outer driver 232 is provided with driving sections. That is, in such embodiments, the function of the inner and outer drivers is reversed, but the total overall functionality of these embodiments remain as in the above-described embodiments.

Figure 23:
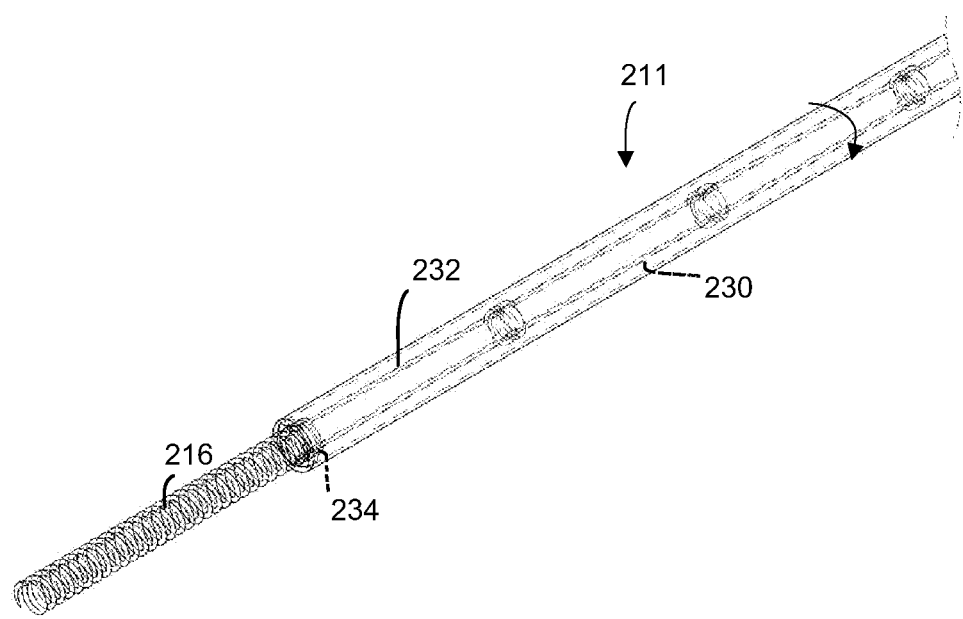
FIG. 23, in a perspective view, illustrates the distal portion of FIG. 16.
Figure 24:
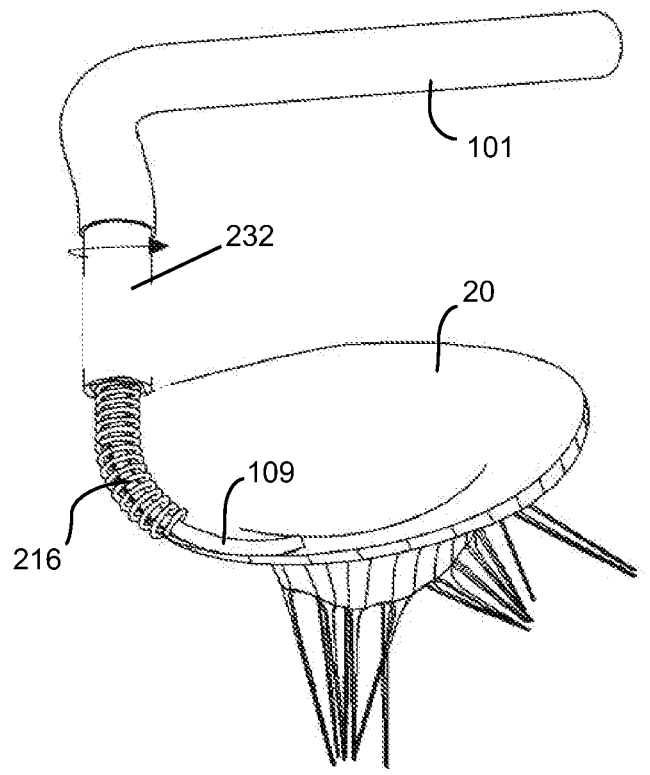
FIG. 24, in a perspective view, illustrates a step of an example of use of the distal portion of FIG. 16.
Figure 25:
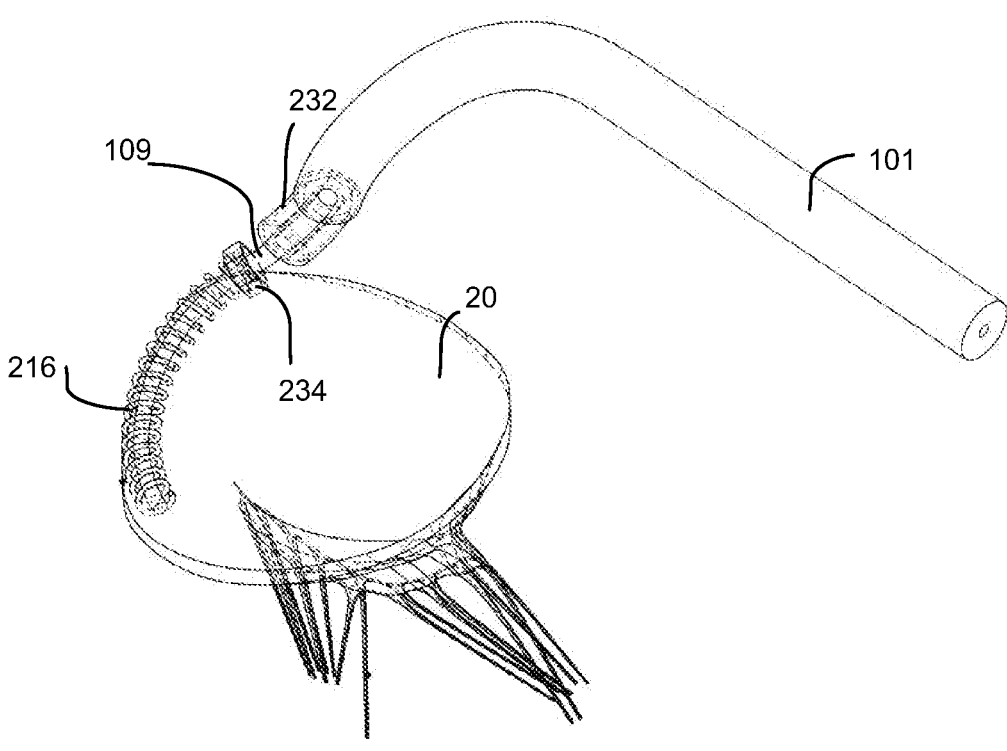
FIG. 25, in a perspective view, illustrates another step of an example of use of the distal portion of FIG. 16.
Figure 26:
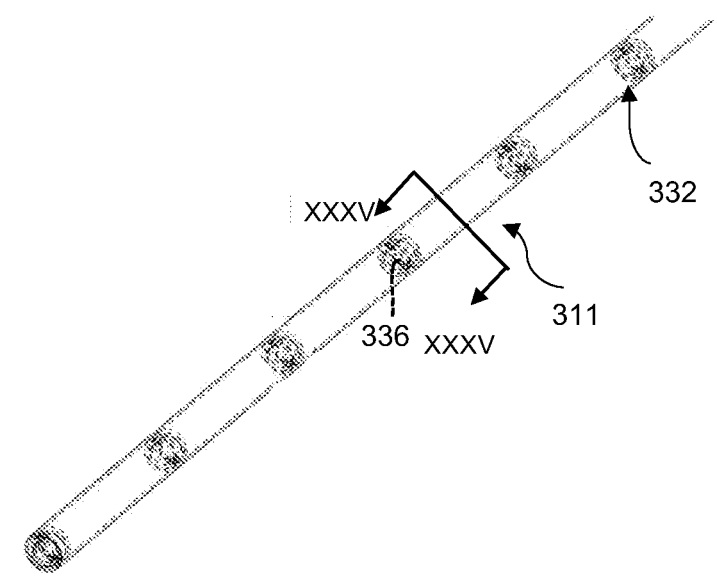
FIG. 26, in a perspective view, illustrates an alternative distal portion usable in a system similar to the system of FIG. 1.
Figure 27:
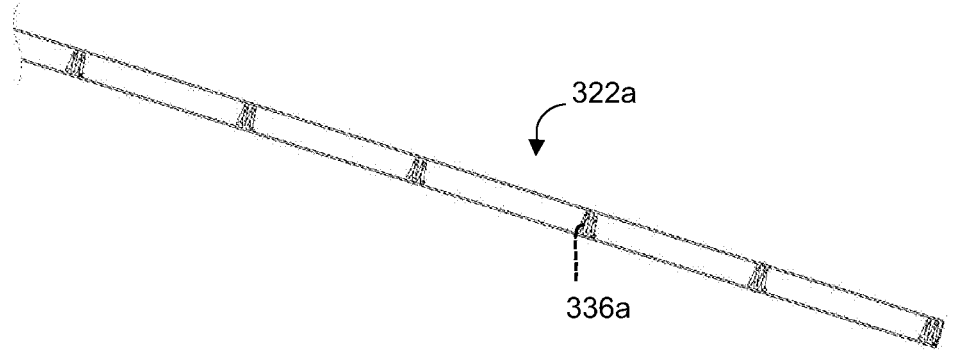
FIG. 27, in a perspective view, illustrates an alternative outer driver usable in the distal portion of FIG. 26.
Figure 28:
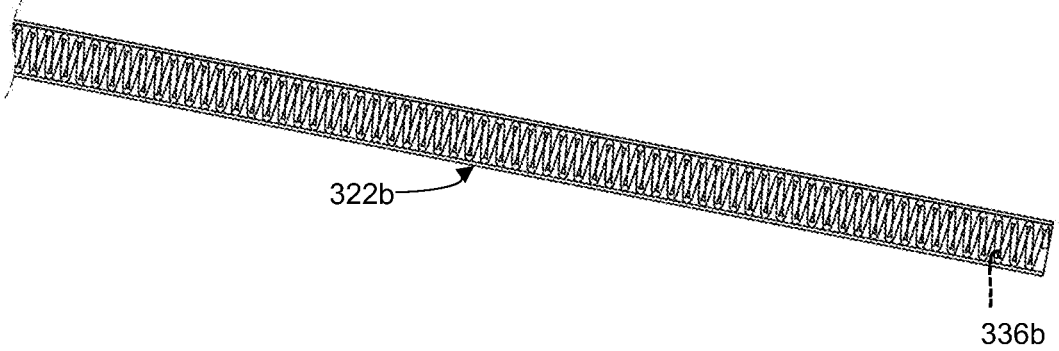
FIG. 28, in a perspective view, illustrates an other alternative outer driver usable in the distal portion of FIG. 26.

FIGS. 23 to 25 illustrate an example of use of the distal portion 211. For example, referring to FIG. 24, the proposed distal portion 211 is usable to implant the helical anchor 216 along the periphery of a cardiac valve 20, for example a mitral valve. The outer driver 232 is provided in a catheter 101 that remains fixed relative to the heart. The catheter 101 can be moved through a patient's vasculature until it is adjacent the valve 20 using conventional techniques. A guide 109 inserted through the inner driver 230 and protruding therefrom is positioned at the location where the helical anchor 216 is to be implanted. In some embodiments, the guide 109 is adhered to tissues using cryoadhesion, or in any other suitable manner.

Referring to FIG. 23, after the inner and outer drivers 230 and 232 have been positioned accordingly, a first one of the helical anchors 216 is advanced by rotating the inner driver 230 relative to the outer driver 232 until the helical anchor 216 protrudes from the inner and outer drivers 230 and 232 with only a small portion thereof and the anchor support 234 remaining in the outer driver 232. Then, as seen in FIG. 24, the outer driver 232 and inner driver 230 are jointly rotated to drive the helical anchor 216 into the tissues in which it is to be implanted. The inner and outer drivers 230 and 232 are allowed to advance along the guide 26 with the helical anchor 216 so that the anchor support 234 remains at the end of the outer driver 232. Once the helical anchor 216 is fully implanted, the inner driver 230 is rotated relative to the outer driver 232 to fully eject the helical anchor 216 and anchor support 234, as seen in FIG. 25. The guide 109 can then be repositioned and these steps can be repeated for the next helical anchor 216.

FIGS. 26 to 35 illustrate various aspects of an alternative distal portion 311 (seen for example in FIG. 311), along with some variants thereof. The distal portion 311 uses concepts similar to the distal portion 211 to implant anchors 316. However, the driving sections 336, 336a or 336b, (similar to the driving sections 236, 236a and 236b, and seen in FIGS. 26, 27 and 28 respectively) are provided in the inside surface of the outer driver 332, 332a and 332b respectively, and it is the inner driver 330 that is configured to prevent rotation relative to the helical anchor 316.

Figure 35:
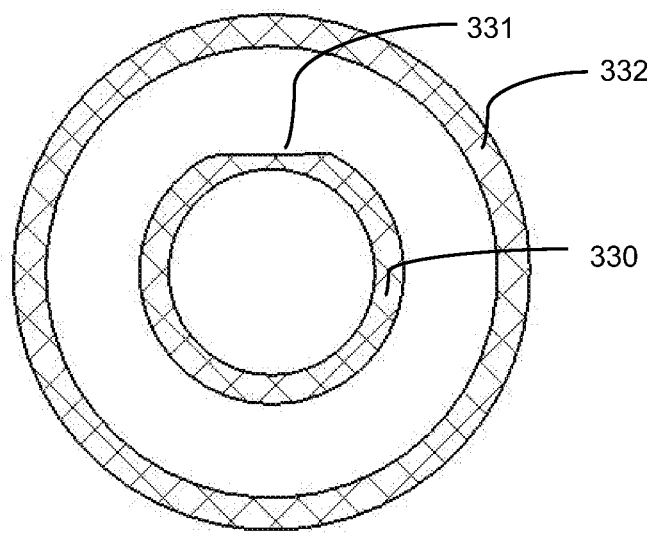
FIG. 35, in a front cross-sectional view along section line XXXV-XXXV of FIG. 36, illustrates the distal portion of FIG. 26.

Indeed, as seen for example in FIG. 35, the outer driver 332 has a generally circular inner and outer configuration. The inner driver 330 is hollow and has a generally circular outer configuration, but defines a longitudinally extending and flat inner driver coupling surface 331. Therefore the outer surface of the inner driver 330 is that of a truncated cylinder. However, any other shape that prevents rotation of the helical anchor 316 relative to the inner driver 330 is within the scope of the invention.

Figure 32:
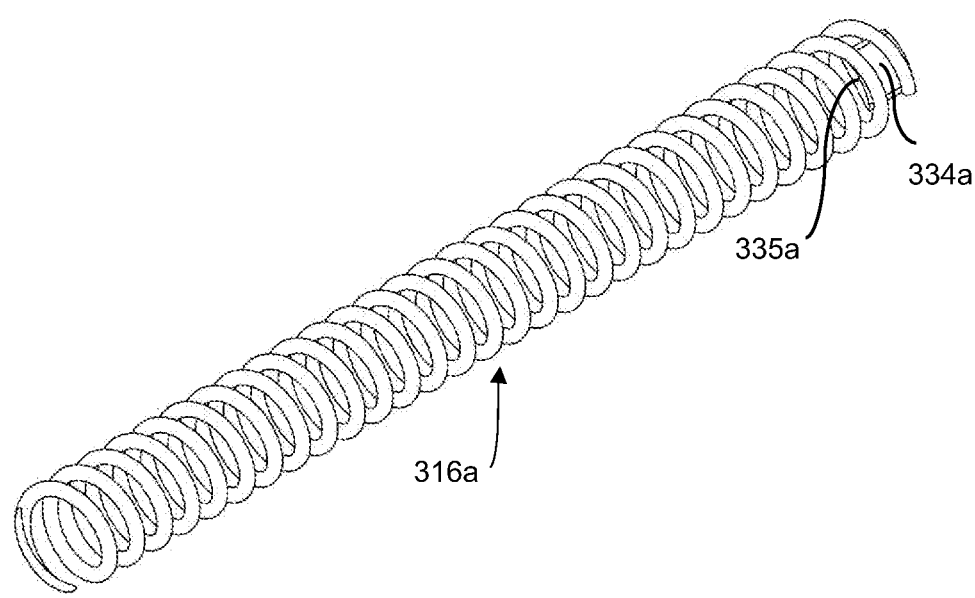
FIG. 32, in a perspective view, illustrate a helical anchor usable with the distal portion of FIG. 26.
Figure 33:
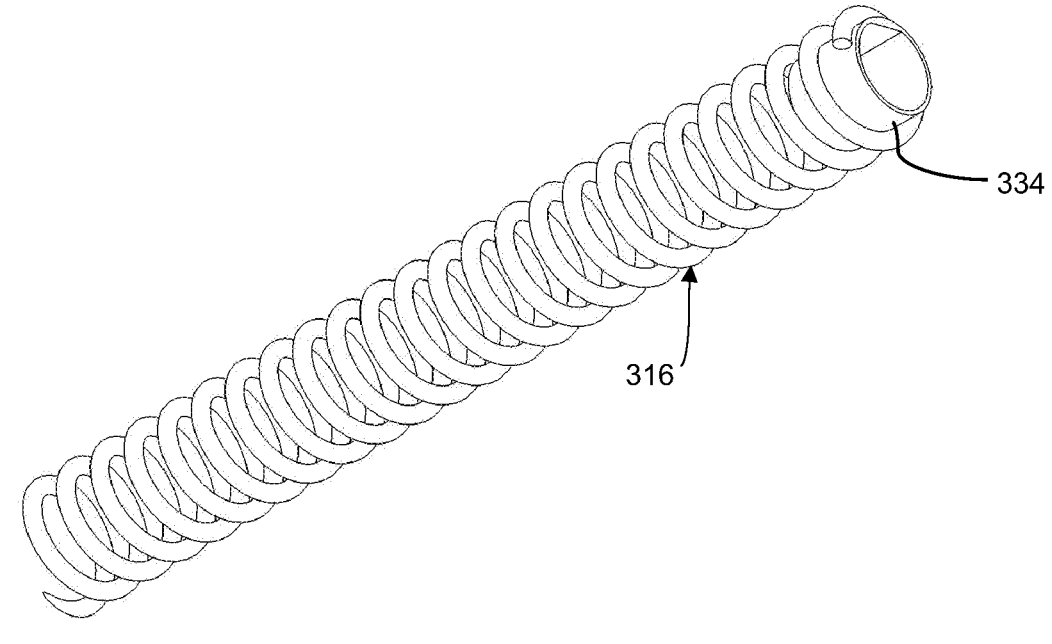
FIG. 33, in a perspective view, illustrate another helical anchor usable with the distal portion of FIG. 26.
Figure 34:
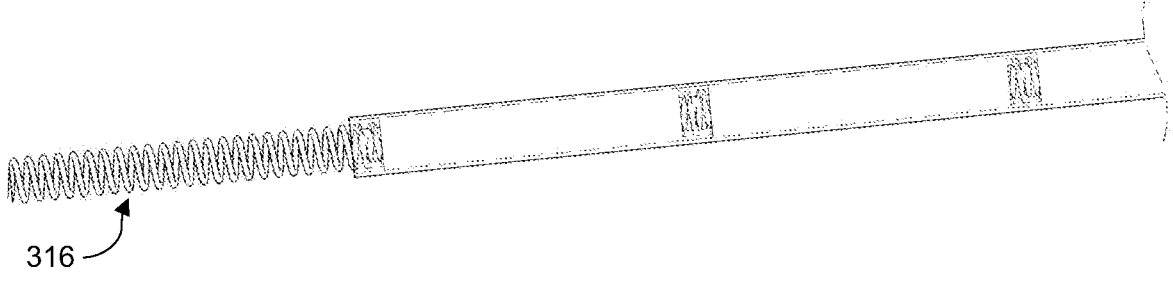
FIG. 34, in a side elevation view, illustrates the step of FIG. 30.

Referring to FIG. 33, the helical anchor 316 is provided with a hollow internal anchor support 334 around which the proximal end of the helical anchor 316 is fixedly mounted. The interior of the internal anchor support 334 is configured and sized to substantially snugly fit the inner driver 330 so that the anchor support 334 cannot rotate relative thereto, but can advance or retreat longitudinally relative thereto. In alternative embodiments, as seen in FIG. 32, a coupling element 334a is mounted to the helical anchor 316a at its proximal end, replacing the internal anchor support 334. The coupling element 334a defines an anchor coupling surface 335a that abuts against the driver coupling surface 331 and is parallel thereto when the anchor 316a is mounted to the inner driver 330. The rest of the helical anchor 316a fits snugly to the inner driver 330. Therefore, most of the anchor support 334 is not needed.

Figure 31:
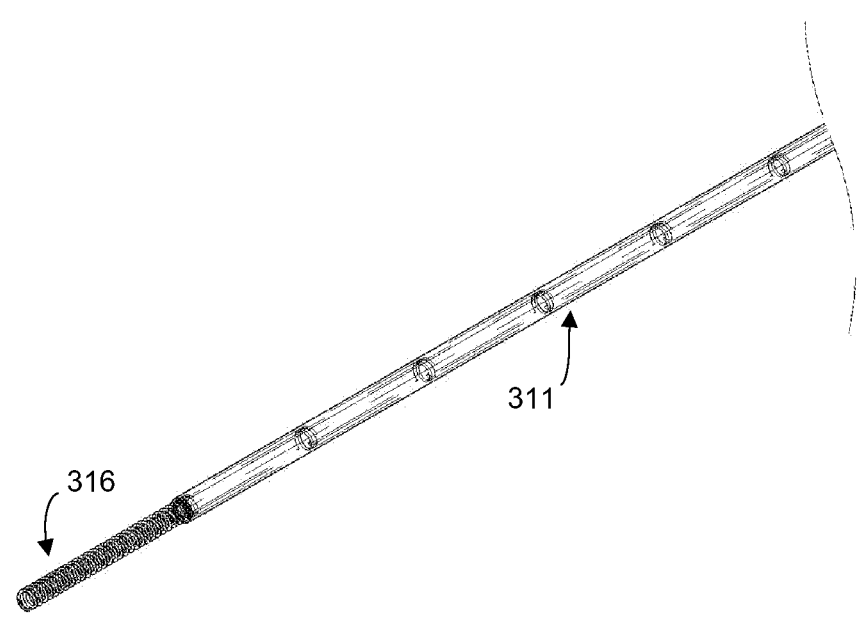
FIG. 31, in a perspective view, illustrates another step in the deployment of multiple helical anchors sequentially using the distal portion of FIG. 26.

In some embodiments, as seen in FIG. 29, the inner driver 330 is provided with a ramp 333 at its distal end. The ramp 333 protrudes slightly from the generally flat driver coupling surface 331 and provide feedback to the operator of the system 300 as an increased resistance will be felt when the distal end of the helical anchor 316 reaches the ramp 333. The ramp 333 however is shallow enough to allow the operator to push the anchor support 334 or the coupling element 334a over the ramp 333. FIGS. 30 and 31 illustrate successive steps in the deployment of the helical anchors 316 and FIG. 32 illustrates the step of FIG. 32 in a different view.

FIGS. 41A to 54 illustrate various aspects of an other distal portion 511 usable in the system of FIG. 1. This distal portion is similar to the distal portions 211 and 300 in that it includes an inner driver 530 (seen for example in FIGS. 41A and 41B) and an outer driver 532 (seen for example in FIG. 42). The inner and outer drivers 530 and 532 include respectively an inner tube 534 and an outer tube 536. The inner and outer drivers 530 and 532 include respectively inner and outer anchor engaging elements 538 and 540. The inner and outer anchor engaging elements 538 and 540 engage respectively threadedly inner engaging and outer engaging portions 518 and 520 of the helical anchor 516 (seen for example in FIG. 45). The inner engaging and outer engaging portions 518 and 520 have opposed handedness, and are either respectively right and left handed or respectively left and right handed.

Figure 43:
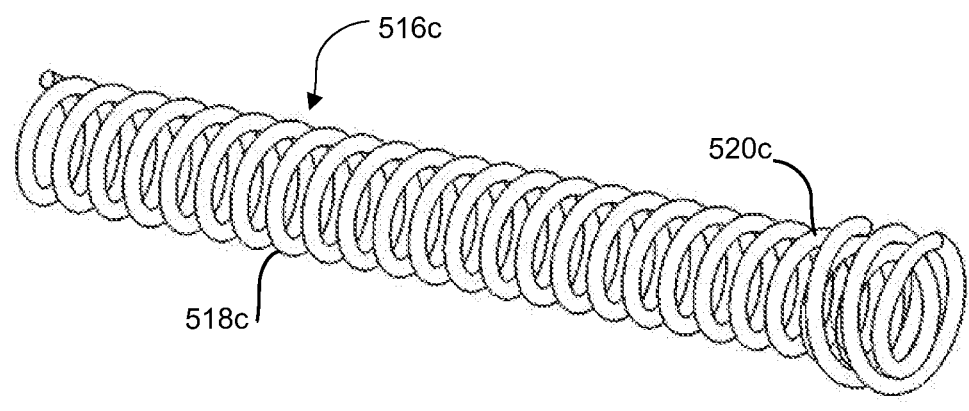
FIG. 43, in a perspective view, illustrates a helical anchor usable with the inner driver of FIGS. 41A and 41B and the outer driver of FIGS. 42A and 42B.
Figure 44:
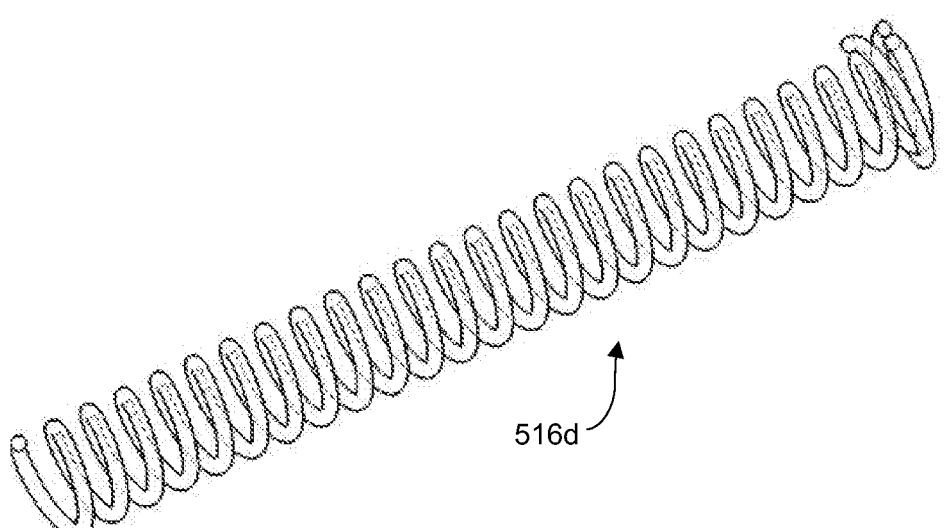
FIG. 44, in a perspective view, illustrates an alternative helical anchor usable with the inner driver of FIGS. 41A and 41B and the outer driver of FIGS. 42A and 42B.
Figure 45:
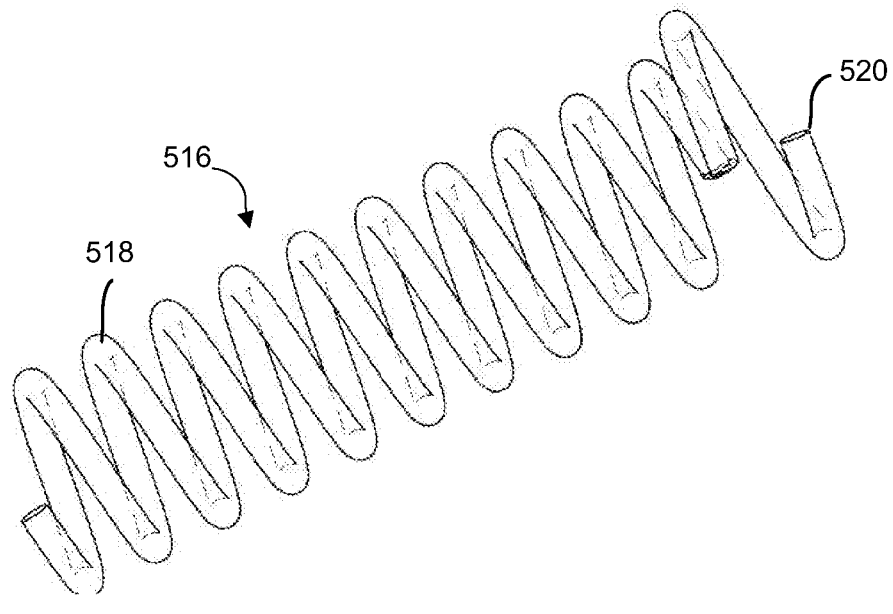
FIG. 45, in a perspective view, illustrates another alternative helical anchor usable with the inner driver of FIGS. 41A and 41B and the outer driver of FIGS. 42A and 42B.

More specifically, the helical anchor 516 includes two sections, the inner engaging and outer engaging portions 518 and 520, that extend longitudinally from each other. In the helical anchor 516 illustrated in the drawings, the inner engaging portion 518 is longer than the outer engaging portion 520, which extends along about one full turn of the helical anchor 516. However, the opposite is possible in other embodiments of the invention. The diameter of the inner engaging portion 518 is smaller than the diameter of the outer engaging section 520. For example, the outer envelope of the inner engaging portion 518 has a diameter substantially similar to the diameter of the inner envelope of the outer engaging portion 520. It should be noted that in alternative embodiments, as seen for example in FIG. 43, for helical anchor 516c, the outer engaging portion 520c, having a handedness opposite the inner engaging portion 518c, overlaps the latter over a portion thereof, instead of extending therefrom. The inner and outer engaging portions 518c and 520c may be made of two superposed coils extending from each other directly at their proximal ends, and may be, in some embodiments, welded to each other at one or multiple locations longitudinally spaced apart from each other, as seen in FIG. 43. In other embodiments, as seen in FIG. 44 for helical anchor 516d, coils of different handedness don't extend from each others.

Figure 46:
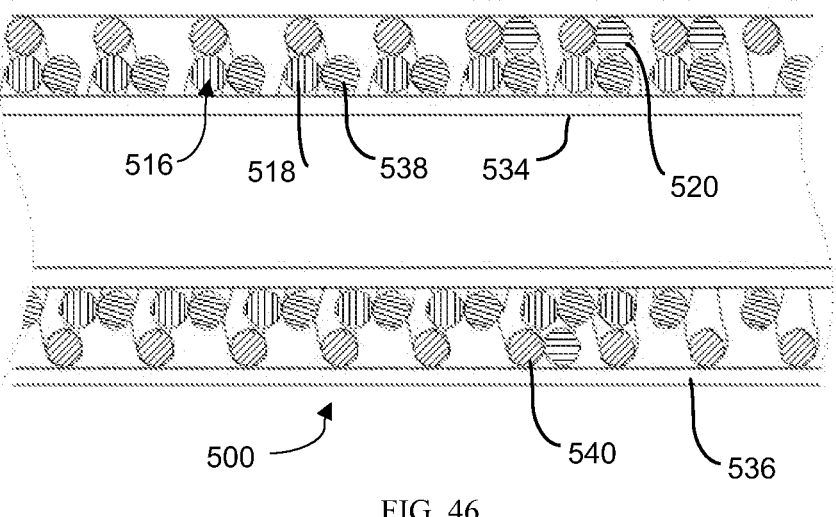
FIG. 46, in a side cross-sectional view midway therethrough, illustrates an assembly including the inner driver of FIGS. 41A and 41B, the outer driver of FIGS. 42A and 42B and the helical anchor of FIG. 45.

The inner and outer anchor engaging elements 538 and 540 may take the forms of coil springs that have substantially similar pitch and diameters to respectively the inner and outer engaging portions 518 and 520. The inner and outer anchor engaging elements 538 and 540 have a common longitudinal axis and are longitudinally fixed relative to each other, but can rotate about the common longitudinal axis relative to each other. The outer envelope of the inner anchor engaging element 538 has a diameter that is substantially similar to the diameter of the inner envelope of the outer anchor engaging element 540, so that there is no or only minimal radial gap between the inner and outer anchor engaging elements 538 and 540, as seen in FIG. 46, which illustrates in a cross-section of the inner anchor engaging element 538 (medium grey), outer anchor engaging element 540 (dark grey) and helical anchor 516 (light grey). The inner and outer anchor engaging elements 538 and 540 are configured so that the gap between two longitudinally spaced apart turns of the inner and outer anchor engaging elements 538 and 540 is large enough to receive therebetween the helical anchor 516. However in alternative embodiments, the inner and outer anchor engaging elements 538 and 540 take the form of suitable threads defined in the inner and outer tubes 534 and 536.

The inner and outer anchor engaging elements 538 and 540 may be secured respectively to the inner and outer tubes 534 and 536 or may be free to rotate relative thereto. In the first case, the actuator 562, described in further details below, may act rotate the inner and outer tubes 534 and 536 to operate the inner and outer drivers 530 and 532. In the second case the actuator 562 rotates directly the inner and outer anchor engaging elements 538 and 540, which are then free to rotate relative to the inner and outer tubes 534 and 536.

Figure 47:
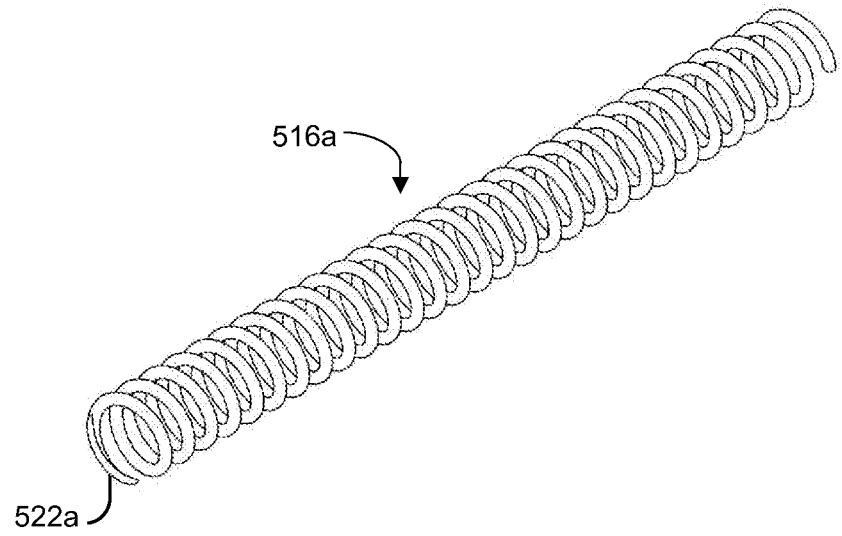
FIG. 47, in a perspective view, illustrates a helical anchor including a beveled tip.
Figure 48:
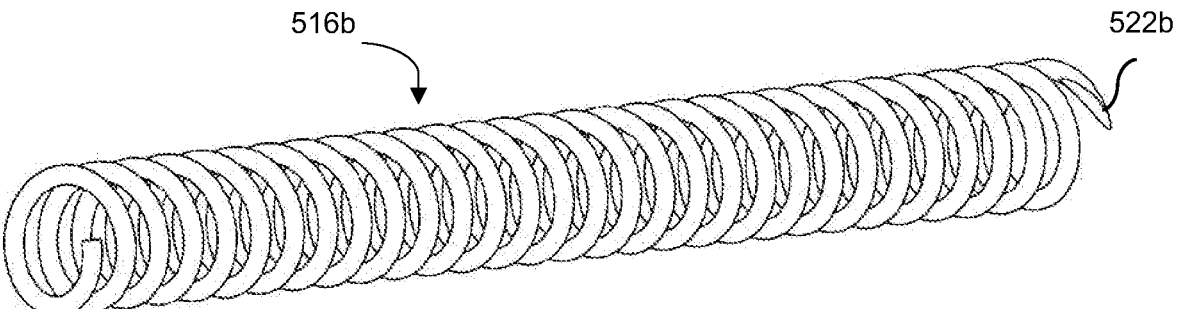
FIG. 48, in a perspective view, illustrates an alternative helical anchor including a beveled tip.

In some embodiments, the distal tip 522a and 522b of the helical anchor 516a and 516b is bevelled to terminate in a sharp edge. As seen in FIG. 47, the distal tip 522a may be bevelled by removing part of the wire forming helical anchor 516a that faces distally. In other embodiments, as seen in FIG. 48, the distal tip 522b may be bevelled by removing part of the wire forming helical anchor 516b that faces proximally.

Figure 50:
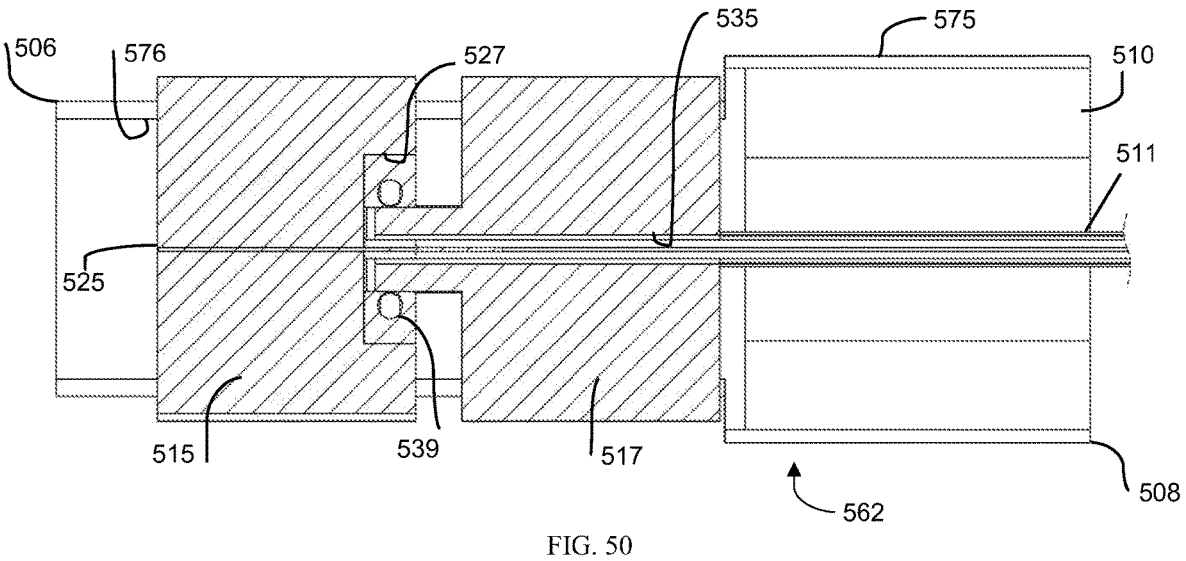
FIG. 50, in a side cross-sectional view midway therethrough, illustrates the actuator of FIG. 49.

FIGS. 49 and 50 illustrate the actuator 562. The actuator 562 is usable not with the inner and outer drivers 530 and 532, but also as an actuator for the distal portions 211 and 311. The actuator 562 includes a hollow actuator body 575 defining a substantially cylindrical body cavity 576 and first and second actuating knobs 515 and 517 mounted to the actuator body 575. The actuator body 575 defines actuator body proximal and distal ends 506 and 508. The actuator body 575 is terminated distally by a distal end wall 510 defining an end wall aperture 511 extending therethrough. One or more recesses 514 extend longitudinally along the outer surface of the actuator body 575 from the actuator body proximal end 506 to provide access laterally to the body cavity 576.

The first and second actuating knobs 515 and 517 are generally cylindrical with an outer diameter substantially similar to an inner diameter of the body cavity 576. The first and second actuating knobs 515 and 517 are received in the body cavity 576 so as to be rotatable independently from each other relative to the body cavity 576 but longitudinally fixed relative to each other. The first and second actuating knobs 515 and 517 may be provided with longitudinal ribs or grooves or a high friction surface to improve gripping by an intended user.

The first actuating knob 515 defines a first knob passageway 525 extending axially therethrough. The inner anchor engaging element 538 is mechanically coupled to the first actuating knob 515 so as to be jointly rotatable therewith. For example, the inner anchor engaging element 538 is fixed relative to the inner tube 534 and the latter is fixedly mounted to the first actuating knob 515 so that its central passageway is in continuation of the first knob passageway 525 to allow insertion of the guide 109 (not seen in FIGS. 49 and 50) therethrough. In some embodiments, the first actuating knob 515 defines a bearing receiving recess 527 at its distal end centred on the first knob passageway 525.

The second actuating knob 517 defines a second knob passageway 535 extending axially therethrough. The outer anchor engaging element 540 is mechanically coupled to the second actuating knob 517 so as to be jointly rotatable therewith, but decoupled from the second actuating knob 517. For example, the outer anchor engaging element 540 is fixed relative to the outer tube 536 and the latter is fixedly mounted to the second actuating knob 517 so that its central passageway is in continuation of the second knob passageway 535 to allow insertion of the inner tube 534 therethrough. In some embodiments, the second actuating knob 517 defines a shaft 537 protruding therefrom at its proximal end and centred on the second knob passageway 535.

A bearing 539 is fitted in the bearing receiving recess 527 and receives the shaft 537. The bearing 539 facilitates relative rotation between the first and second actuating knobs 515 and 517. However, any other suitable coupling allowing such rotation between the first and second actuating knobs 515 and 517 is possible in alternative embodiments.

In use, rotating the first actuating knob 515 while maintaining the second actuating knob 517 fixed advances and retreats the helical anchor 516. The helical anchor 516 rotates during this process in the direction opposite to the pitch of the inner anchor engaging element 538. Once the helical anchor 516 is almost entirely protruding from the outer tube 536, the first and second actuating knobs 515 and 517 can be rotated jointly to advance the helical anchor 516 in the adjacent tissue. Finally, the helical anchor 516 is released by rotating the second actuating knob 517 while maintaining the first actuating knob 515 fixed.

Figure 51:
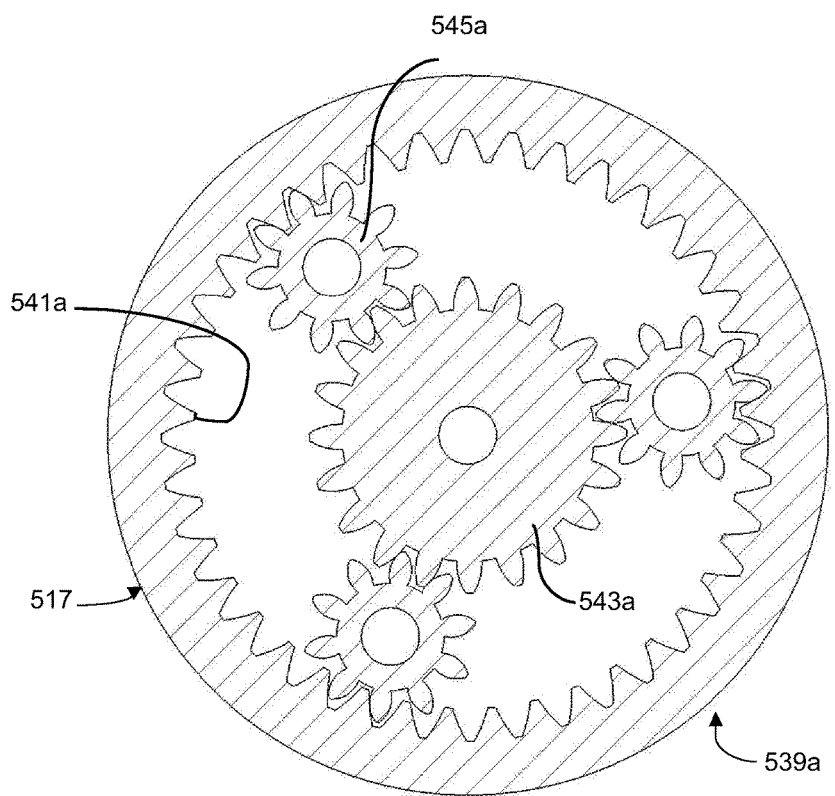
FIG. 51, in a front cross-sectional view, illustrates a planetary gear set part an alternative actuator.
Figure 52:
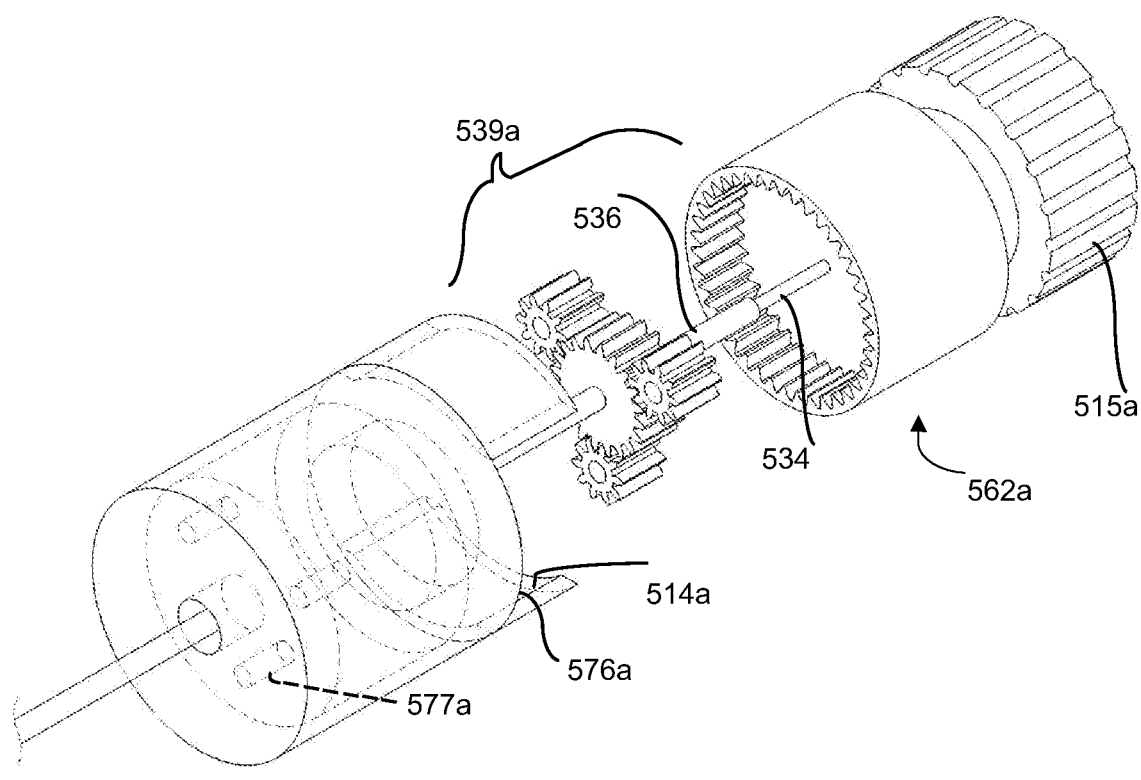
FIG. 52, in a perspective exploded view, illustrates an alternative actuator including the planetary gear set of FIG. 51.
Figure 53:
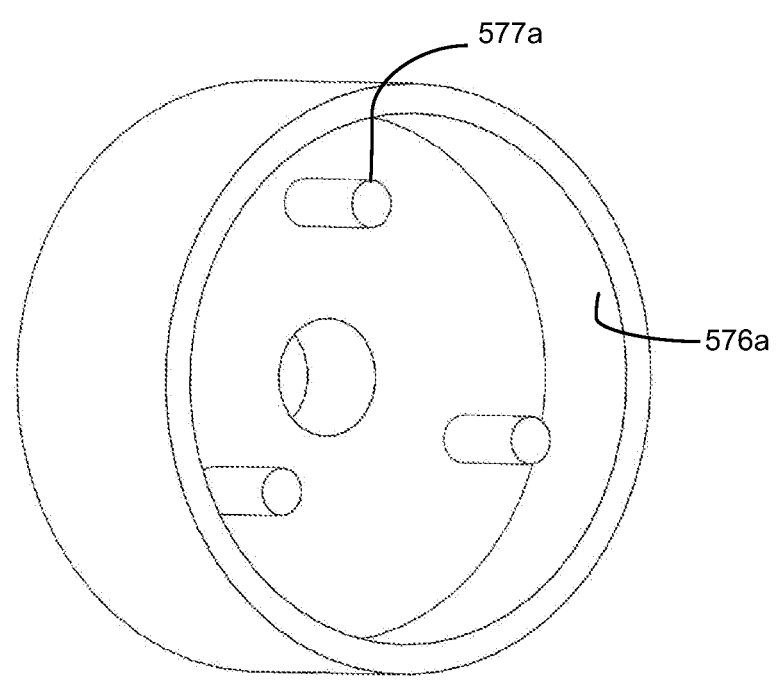
FIG. 53, in a perspective view, illustrates mounting pins part of the actuator of FIG. 52.
Figure 54:
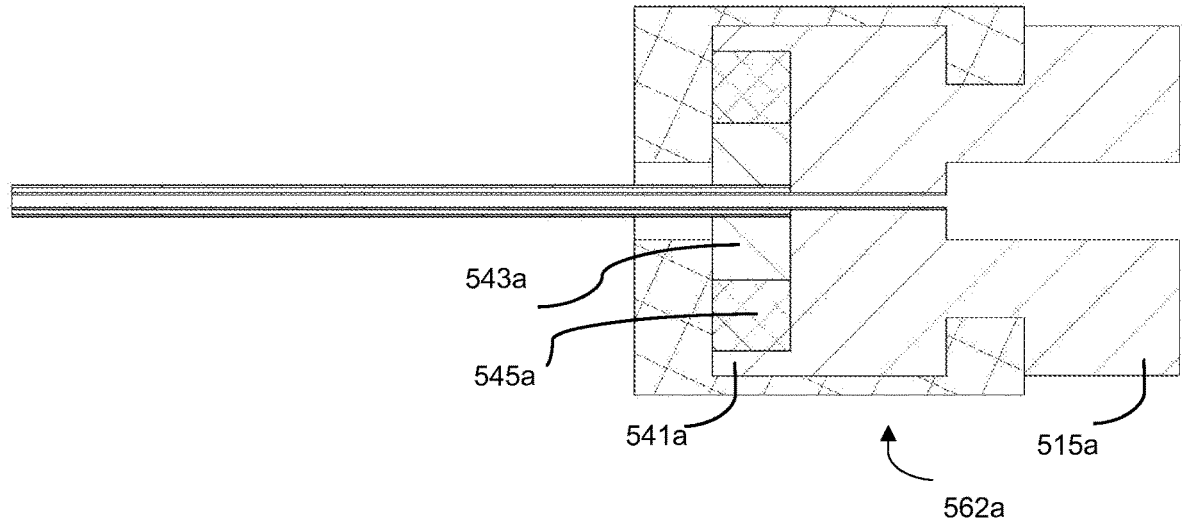
FIG. 54, in a schematic view, illustrates the actuator of FIG. 52.

The actuator 562a shown in FIG. 52 is similar to the actuator 562 except that the second actuating knob 517 is omitted. Instead, the first actuating knob 515a is directly coupled to the inner tube 534, as in the actuator 562, but is also indirectly coupled to the outer tube 536 by a planetary gear set 539a. As seen in FIG. 51, the planetary gear set 539a includes a ring gear 541a formed inside the outer periphery of the first actuating knob 515a, at its distal end, a sun gear 543a provided at the centre of the ring gear 541a and planet gears 545a extending therebetween. Three planet gears 545a are shown in the drawings, but any suitable number of planet gears 545a are within the scope of the invention. The sun gear 543a is coupled to the outer tube 536 for joint rotation therewith. In this embodiment, the helical anchor 516 both advances and rotates simultaneously, such that cinching occurs as soon as the helical anchor 516 protrudes from the outer tube 536.

The sun and planet gears 543a and 545a are external spur gears, while the ring gear 541a is an internal spur gear. The sun, planet and ring gears 543a, 545a and 541a have the same pitch/module and are designed such that no interference occurs during meshing. The sun, planet and ring gears 543a, 545a and 541 each have a central bore. The planet gears 545a are fixed to the actuator frame 545 by being rotatably mounted to mounting pins 577a extending in the body cavity 576a. Hence, the inner and outer tubes 534 and 536 rotate in opposite directions and at different speeds depending on the gear ratio between the sun and ring gears 543a and 541a. The outer tube 536 rotates at a higher speed since it is connected to the smaller gear (sun gear 543a), hence the conditions for continuous cinching can be satisfied.

In order to find the appropriate rotational speeds between the drivers, the following equations are applied:

ω: rotational speed, rpm
V: translational speed, mm/min
P: pitch, mm/rev
Subscripts:
h: outer anchor engaging element 540
d: inner anchor engaging element 538
a: helical anchor 516
Sign convention: ω and V are positive in the direction that is favorable for suturing and advancing distally in the tissue. Hence both values should be positive for the anchor simultaneously for continuous suturing. Also, note that $P_d$ and $P_h$ have opposite signs since the springs are coiled in opposite directions. $P_d$ is positive since the spring meshes with the distal portion of the anchor. Note that:

$$\omega_a = (\omega_h P_h - \omega_d P_d)/(P_h - P_d)$$

$$V_a = P_h P_d (\omega_d - \omega_h)/(P_h - P_d)$$

Based on the above relations, the conditions for continuous suturing ($\omega_a > 0$; $V_a > 0$) translate to the following:

$$\omega_d > \omega_d$$

$$|P_d/P_h| < |\omega_h/\omega_d|$$

Figure 58:
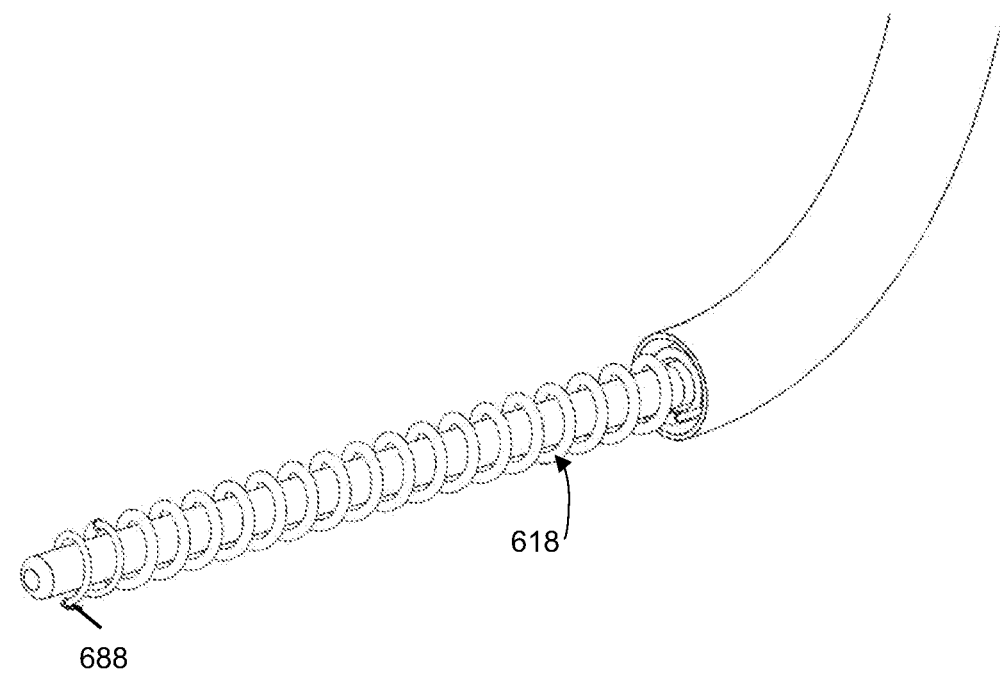
FIG. 58, in a perspective view, illustrates an alternative helical anchor.
Figure 59:
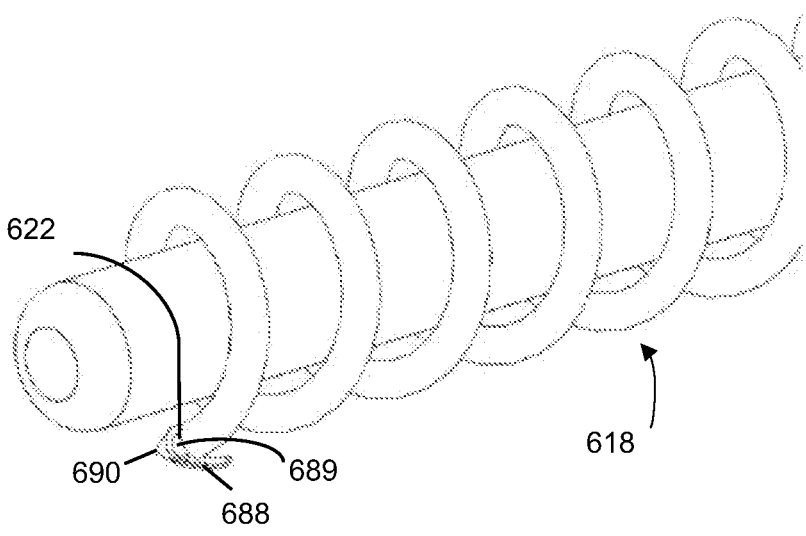
FIG. 59, in a perspective view, illustrates part of the helical anchor of FIG. 58.
Figure 60:
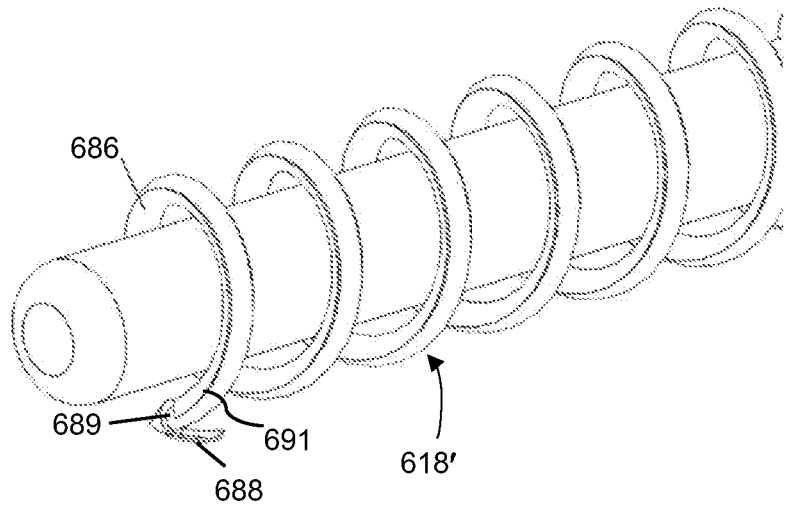
FIG. 60, in a perspective view, illustrates an other alternative helical anchor.

FIGS. 58 to 60 illustrate alternative helical anchors usable in the helical anchor driving system of FIGS. 1 to 57. Referring to FIG. 59, in some embodiments a hook 688 is removably mountable to the helical anchor 618. A suture thread 686 (seen in FIG. 60) is secured to the hook 688. For example, the hook 688 is crimped to the end of the suture thread 686. In other embodiments (not shown in the drawings), the hook 688 defines a suture eye and a suture thread 686 is attachable to the suture eye. In some embodiments, the helical anchor 618 is made of a hollow tube and the suture thread 686 extends through the helical anchor 618. The hook 688 has a part thereof insertable in the hollow tube at the helical anchor distal end 622. For example, a hook attachment 689 part of the hook 688 is configured to be slidably inserted in the helical anchor 618. The hook 688 is typically terminated by a sharp point 690. In other embodiments, the helical anchor 618', seen in FIG. 60, defines an helicoidal groove 691 therealong receiving the suture thread 86.

The hook 688 is configured so that the helical anchor 618 may be advanced relatively easily in the target biological tissue 12 with the hook 688 remaining secured to the helical anchor 618. The hook 688 is also configured so that withdrawing the helical anchor 618 from the target biological tissue 12 causes the latter to catch the hook 688 so that the hook 688 is detached from the helical anchor 618 or 618' as the target biological tissue pulls on the hook 688. In these embodiments, the helical anchor 618 or 618' can be withdrawn and removed from the patient.

FIGS. 61 to 68 illustrate other variants of the system 100. Only the distal portion 111 of the system 100 is modified in these variants, and, accordingly, only this distal portion is described. Notably, the actuator 562 described hereinabove and the connections between the actuator 562 and the inner and outer drivers of the present variant remain as described hereinabove for the previously described variants.

Figure 61:
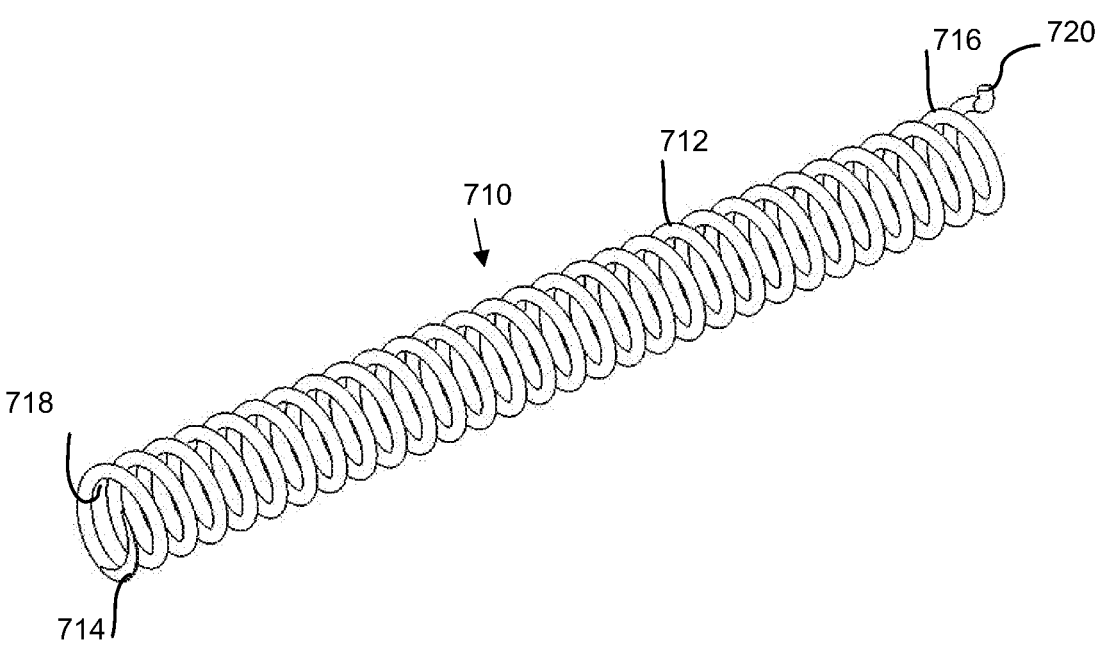
FIG. 61, in a perspective view, illustrates yet another embodiment of a helical anchor.
Figure 62:
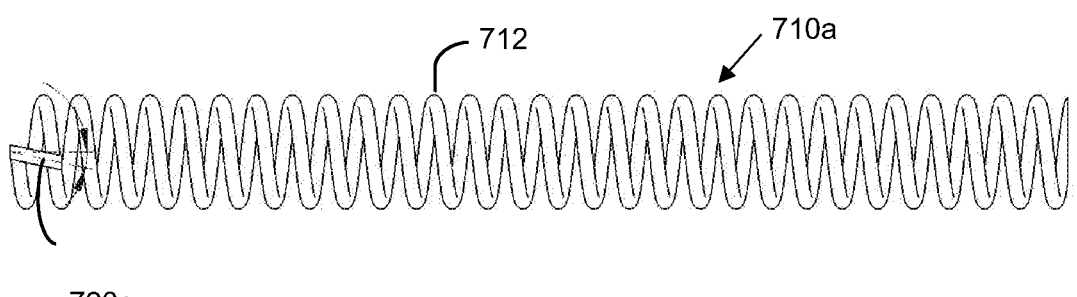
FIG. 62, in a side elevation view, illustrates yet another embodiment of a helical anchor.

The present variant is usable with a helical anchor 710, shown in FIG. 61. The helical anchor 710 includes a substantially helical anchor body 712 defining anchor body proximal and distal ends 716 and 714 and an anchor body passageway 718 extending therethrough between the anchor body proximal and distal ends. The anchor body 712 is delimited inside a generally cylindrical shape and has an anchor body outer diameter. The anchor body 712 is for example formed of a coiled wire or other similar structure. An anchor protrusion 720 protrudes radially outwardly from the anchor body 712 further than the anchor body outer diameter at the anchor body proximal end 716. The anchor protrusion 720 is for example formed by bending the proximal end of a wire used to form the anchor body 712. The anchor protrusion 720 is for example a wire segment that extends substantially radially. In other embodiments, a suitably shaped piece of material is welded or otherwise attached to a helical coil to form the anchor protrusion 720.

However, the anchor protrusion 720 may take any other suitable shape. For example, the helical anchor 710a seen in FIG. 62 includes an anchor protrusion 720a that takes the form of a short rectilinear segment oriented along the anchor body 712 outside of the anchor body 712. The anchor protrusion 720a is angled relative to a longitudinal axis of the anchor body 712a to match a corresponding angle of a slot described in further details hereinbelow. Other shapes of the anchor protrusion 720a that can suitably engage this slot are also usable.

Figure 63:
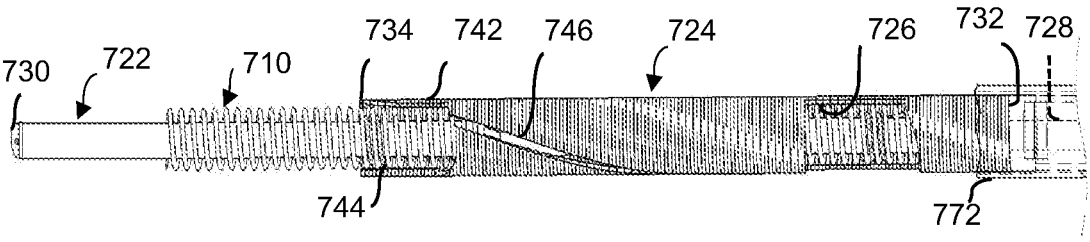
FIG. 63, in a side cut away view, illustrates inner and outer drivers usable with the helical anchors of FIGS. 61 and 62.

Referring to FIG. 63, the helical anchors 710 and 710a are drivable into biological tissue using substantially elongated inner and outer drivers 722 and 724, the helical anchor 710 being used in FIG. 63. The inner and outer drivers 722 and 724 are concentric relative to each other, with the inner driver 722 inside the outer driver 724, and define a driver passageway 726 therebetween. The helical anchor 710 and 710a is mountable between the inner and outer drivers 722 and 724 in the driver passageway 726. Typically, but not necessarily, the driver passageway 726 is substantially annular.

The inner driver 722 defines longitudinally opposed inner driver proximal and distal ends 728 and 730. The outer driver defines longitudinally opposed outer driver proximal and distal ends 732 and 734. The inner and outer drivers 722 and 724 are axially rotatable relative to each other and longitudinally substantially fixed relative to each other. This relationship is achieved by suitably connecting the inner and outer drivers 722 and 724 to the actuator 562, through suitable structures, such an elongated tubes extending through the catheter 109. Thus, the inner and outer drivers are operatively coupled to the inner and outer drivers 722 and 724 at the inner and outer driver proximal ends 728 and 732 for selectively rotating the inner and outer drivers 722 and 724 relatively to each other.

Figure 64:
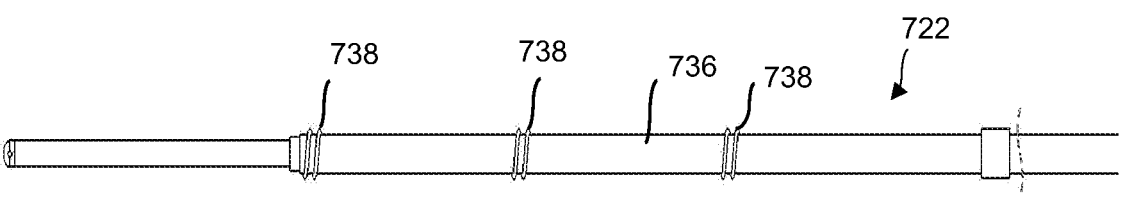
FIG. 64, in a side elevation view, illustrates the inner driver of FIG. 63.

Referring for example to FIG. 64, the inner driver 722 defines an inner driver outer surface 736 facing the driver passageway (not shown in FIG. 64) and provided with at least one protrusion 738 protruding in the driver passageway and configured for engaging the helical anchor (not shown in FIG. 64) when the helical anchor is mounted in the driver passageway and preventing pure translation of the anchor along the inner driver 722 while allowing helical movements of the helical anchor relative to the inner driver 722. FIG. 64 illustrates three protrusions 738, but any suitable number of protrusions 738 is usable. The protrusions 738 are further described hereinbelow.

The inner driver 722 may terminate flush with the outer driver 724 or may protrude distally therefrom. Also, the inner driver 722 may be hollow to allow circulation of a cooling fluid thereinto so that the inner driver 722 may be cryogenically adhered to biological tissue in use.

Figure 65:
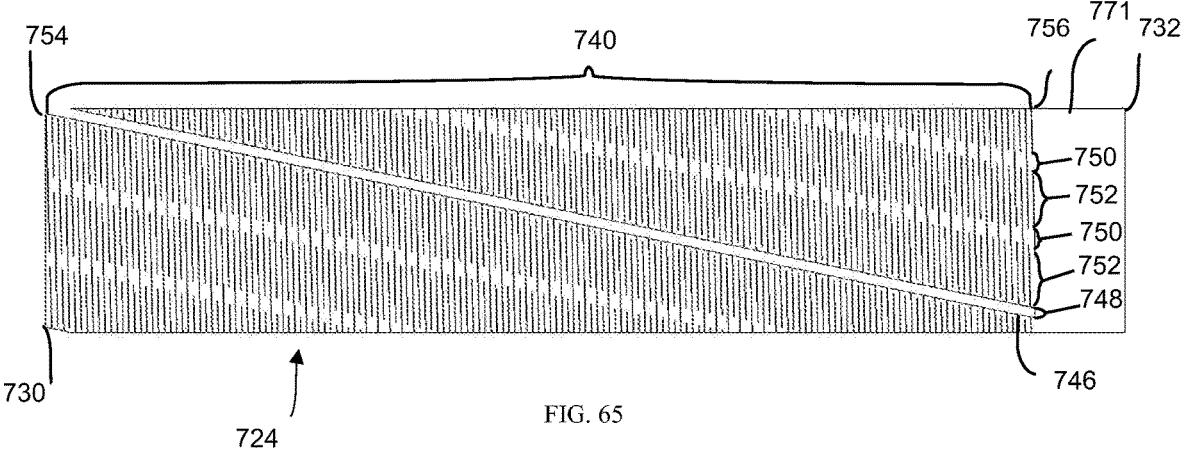
FIG. 65, in a flattened view, illustrates a driving portion part of the outer driver of FIG. 63.

The structure of the outer driver 724 is better understood with reference to FIG. 65. In FIG. 65, the typically generally cylindrical shape of the outer driver 724 has been flattened. In other words, FIG. 65 illustrates the outer driver 724 as it would appear is a longitudinal cut was performed therealong and the resulting structure was unrolled to produce a flat sheet. The outer driver 724 includes a driving section 740 extending from the outer driver distal end 730 towards the outer driver proximal end 732. The driving section 740 defines opposed driving section outer and inner surfaces 742 and 744 (seen for example in FIG. 63). The driving section inner surface 744 faces the driver passageway 726. The driving section 740 is provided with a slot 746 between the driving section inner and outer surfaces 744 and 742. The slot 746 extends along the driving section from the outer driver distal end 730 towards the outer driver proximal end 732. The slot 746 is configured and sized for receiving the anchor protrusion 720 or 720a thereinto and allowing movements of the anchor protrusion 720 or 720a along the slot 746. For example, the anchor protrusion 720 has a cylindrical shape of a diameter substantially similar to a width of the slot 746.

Figure 68:
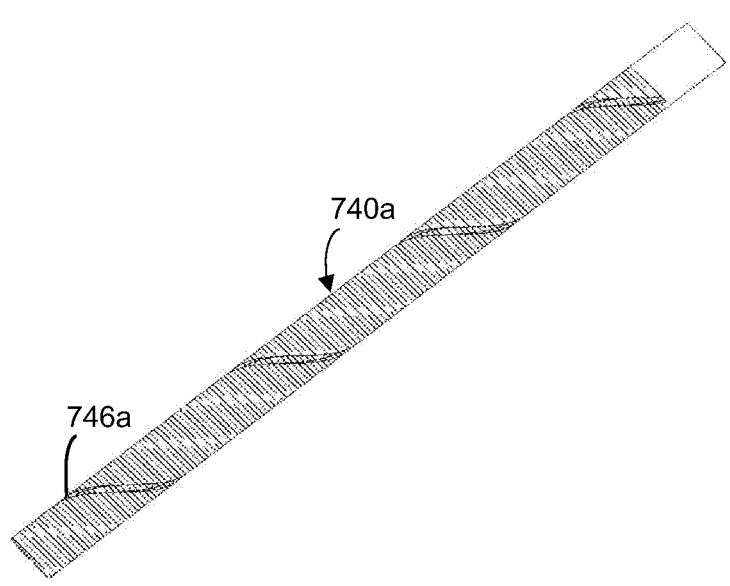
FIG. 68, in a perspective view, illustrates an alternative driving portion.

In some embodiments, the slot 746 is helical around the driving section 740, but other shapes, such as a rectilinear slot 746, are possible. The slot 746 may extend so that it covers a single turn around the driving section 740, as seen in FIG. 63. In other embodiments, as seen in FIG. 68, the slot 746a covers more than one turn around the driving section 740a.

The inner and outer drivers 722 and 724 may be relatively short so that only one helical anchor 710 and 710a fits therebetween. However, in other embodiments, the inner and outer drivers 722 and 724 are relatively long so that more than one helical anchor 710 and 710a fit therebetween. In such embodiments, many helical anchors 710 and 710a can be deployed one after the other without having to reload a new helical anchor 710 and 710a after each deployment.

Returning to FIG. 65, a specific embodiment of the driving section 740 is now further described. While in some embodiments other structures of the driving section 740 are usable, for example a full cylinder in which the slot 746 would be defined, the embodiment described hereinbelow has proven to be highly advantageous as it is relatively rigid in torsion, while being relatively flexible in flexion. In other words, the driving section 740 described hereinbelow can transmit relatively large torques to drive the helical anchor 710 and 710a into tissue while being relatively easily bent to navigate for example through a patient's vasculature for catheter-based operation. It should also be noted that the structure of the driving section 740 may be also used in other catheter-based applications wherein these properties are useful, without requiring for example the inner driver 722.

The driving section 740 defines a slot region 748, at least one backbone region 750 and intermediate regions 752 all distributed circumferentially around the driving section 740. Each intermediate region 752 extends between either adjacent backbone regions 750 or between one of the backbone regions 750 and the slot region 748. The slot, backbone and intermediate regions 748, 750 and 752 each extend along the driving section 740 from a distalmost location 754 to a proximalmost location 756. The slot and backbone regions 748 and 750 are all disjoint from each other and separated from each other by the intermediate regions 752. The circumferential distribution of the slot, backbone and intermediate regions 748, 750 and 752 does note require that each of the slot, backbone and intermediate regions 748, 750 and 752 extends purely longitudinally along the driving section 740. While such a configuration is possible in other embodiments, in some embodiments, the slot, backbone and intermediate regions 748, 750 and 752 each extend helically around the driving section 740. Also, FIG. 65 illustrates an embodiment including two backbone regions 750, and therefore three intermediate regions 752. However, other suitable number of backbone and intermediate regions are also possible in other embodiments.

Figure 66:
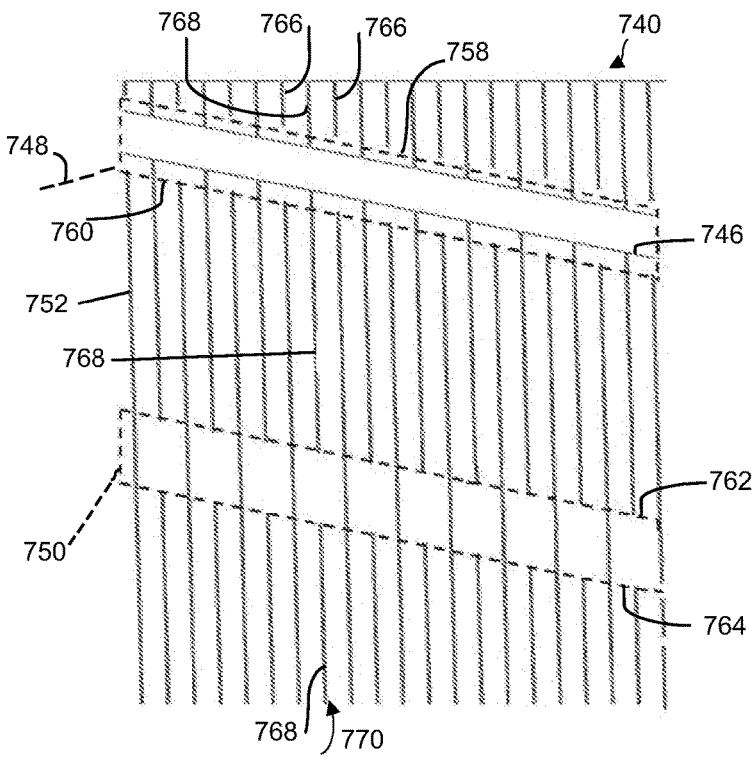
FIG. 66, in an enlarged flattened view, illustrates part of the driving portion of FIG. 65.

FIG. 66 shows a portion of the driving section 740 and better illustrates details of the structure of the driving section 740. The slot region 748 includes the slot 746 and extends circumferentially along a circumferential width wider than the slot 746. In other words, at each circumference around the driving section 740, the slot region 748 occupies a larger angular extent than the slot 746. The slot region 748 defines opposed slot region first and second side edges 758 and 760, the slot 746 being spaced apart from each of the slot region first and second side edges 758 and 760, typically centered therebetween. Each backbone region 750 similarly defines opposed backbone region first and second side edges 762 and 764. Thus, when going circumferentially around the driving section 740 at any longitudinal position therealong starting from the slot region first side edge 758 towards the slot 746, the following regions are crossed in sequence: the slot 746, the slot region second side edge 760, one of the intermediate regions 752, a backbone region first side edge 762, the backbone region to which the backbone region first side edge 760 belongs, a backbone region second side edge 764 and another intermediate region 752. If there are more than one backbone region 750, they will also be crossed alternatively with intermediate regions 752 until returning to the slot region first side edge 758, at which point a whole circumference of the driving section 740 has been traveled along. It should be noted that in embodiments in which the slot, backbone and intermediate regions 748, 750 and 752 are helical, these crossings will occur at different angular positions around the driving section 740 for different longitudinal positions therearound.

The driving section 740 further defining a plurality of first slits 766 and a plurality of second slits 768. Each of the first and second slits 766 and 768 extend between the driving section inner and outer surfaces 744 and 742, the first and second slits 766 and 768 being all disjoint from each other. Each first slit 766 extend around the driving section 740 between the slot region first and second side edges 758 and 760. The second slits 768 each extend between one of a backbone region first and second side edges 762 and 764 and either a backbone region first or second side edge 762 and 764 of an adjacent backbone region 750 or the slot 746. Thus, the first slits 766 each extend along most of the circumference of the driving section 740, only coming slightly short of the slot 746. The second slits 768 each extend along a smaller portion of the circumference of the driving section 740. Some of the second slits 768 reach the slot 746. Other ones extend between adjacent backbone regions 750. Only the first slits 766 interrupt the backbone regions 750. The slot 746 and the first and second slits 766 and 768 can be for example laser cut from a cylindrical blank or from a flat blank that is afterwards rolled to form a cylinder, among other possibilities.

Although not necessarily the case in all embodiments, the slot and backbone regions 748 and 750 are typically substantially parallel to each other. In some embodiments, the slot and backbone regions 748 and 750 are substantially helical around the outer driver.

In some embodiments, the second slits 768 define slit groups 770 including second slits 768 in prolongation of each other around the driving section 740. Each slit group 770 thus defines an interrupted slit extending around the driving section 740 and interrupted in the backbone regions 750.

Typically, but not necessarily, the first slits 766 and the slit groups 770 alternate longitudinally along the driving section 740. That is, if one was to travel along the driving section 740 parallel to the slot 746 in one of the intermediate regions 752, one would cross alternatively first and second slits 766 and 768. In the backbone regions 750, one would only cross first slits 766 as the second slits 768 are not present in the backbone regions 750.

Typically, the first and second slits 766 and 768 are each substantially circumferential. However, first and second slits 766 and 768 that have a pitch relative to the driving section 768, or that are in other words helical or similarly shaped, are within the scope of the invention. The first and second slits 766 and 768 are also typically substantially rectilinear when flattened.

In a typical embodiment, all the first slits 766 are substantially parallel to each other and all the second slits 768 are parallel to the first slits 766. For example, all the first and second slits 766 and 768 are arc segment shaped with a center of rotation at a longitudinal axis of the driving section 740. However, slits having different orientations or having different shapes are also possible.

In some embodiments, the slot 746 terminates short of the outer driver proximal end 732. In such embodiments, the outer driver 724 may define a torque section 771 between the outer driver proximal end 732 and the driving section 740, the torque section 771 being more rigid in torsion and flexion than the driving section 740. This may be required to properly transmit torque between the actuator 562 and the driving section 740 in embodiments in which the driving section 740 is relatively far away from the actuator 562.

Referring to FIG. 64, in some embodiments, the protrusions 738 are substantially helical, for example going twice around the inner driver 722, and protrude from the inner driver outer surface 736. The protrusions 738 have a pitch similar to the pitch of the helical anchor 710 and 710a and a width typically similar to the gap between adjacent coils of the helical anchor 710 and 710a. Also, the protrusions 738 typically have a thickness similar to that of the coils of the helical anchor 710 and 710a. While a single long coil that would cover the whole length of the inner driver 722 is possible, in some embodiments, a series of helical protrusions 738 are provided, longitudinally spaced apart from each other and each protruding from the inner driver outer surface 736. These helical protrusions 738 are separated longitudinally from each other by regions of the inner driver outer surface 736 devoid of protrusions protruding in the driver passageway 726. This configuration reduces friction between the inner driver 722 and the helical anchors 710 and 710a. The spacing between the protrusions 738 is smaller than the length of the helical anchors 710 and 710a so that at any time, at least one protrusion 738 engages the helical anchors 710 and 710a.

Figure 67:
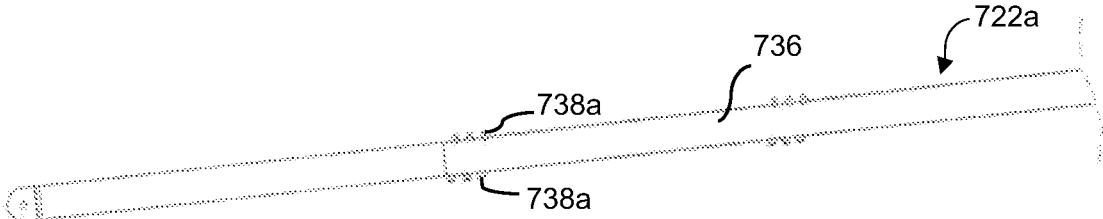
FIG. 67, in a side elevation view, illustrates an alternative inner driver.

In another example, as seen in FIG. 67, the protrusions 738*a* of an alternative inner driver 722*a* take the form of series of pegs longitudinally spaced apart from each other, each protruding from the inner driver outer surface 736. The pegs 738*a* may be grouped in groups of relatively tightly packed pegs, with a spacing corresponding to the pitch of the helical anchor 710 and 710*a*, separated by larger gaps devoid of pegs. Also, the pegs 738*a* may be distributed at various angular positions about the inner driver 722*a*. In other words, the pegs 738*a* are similar to what would be obtained by removing most of the helical protrusions 738 and keeping only small portions thereof.

In some embodiments, as seen in FIG. 63, an outer shell 772 covers the driving section 740 and in some embodiments other portions of the outer driver 724. The outer shell 772 is for example heat shrunk to the outer driver 724.

In some embodiments, the inner driver 722 is of fixed length. In other embodiments, the inner driver includes a telescopic tip that may be deployed distally. In such embodiments, the protrusions 738 are provided on the fixed part of the inner driver.

In other embodiments, as seen in FIG. 80, the slot 741 is formed by running a pair of wires 743 parallel to each other, for example each having a helical shape or a straight shape, along the interior surface of a catheter 745. The gap between these wires defines a slot that can then receive the anchor protrusion 720. An inner driver usable in this embodiment is similar to the above-described inner driver 722.

In yet other embodiments (not shown in the drawings), the slot 746 is provided on the inner driver and the outer driver is provide with the protrusions 738 that then protrude inwardly in the anchor passageway 726. Thus, the inner and outer driver described above have their positions switched relative to the above-described embodiment.

More generally, the helical anchor 710 may be understood as being advanced using a mating portion of the helical anchor 710 that mates and engages a guide of a driver along which the mating portion is movable. The guide extends along a catheter, for example longitudinally or helically. The mating portion cannot however do a pure rotation about the guide. Above, the mating portion is the anchor protrusion 720 and the guide is the slot 746. The guide may be provided in an outer or an inner driver. The helical anchor 710 also engages protrusions on the other one of the inner and outer driver, so that the helical anchor 710 can have a helical movement around the protrusions. The protrusions 738 have this role in the embodiment described above.

FIG. 81 illustrates such an alternative embodiment of a helical anchor 710*b* in which the mating portion 820*b* takes the form of a pair of parallel rails provided outside of the anchor body 712*b*. The guide is for example a wire 750 secured inside a tube 752, as seen in FIG. 82, or simply a rib 754 extruded inside the tube 756, as seen in FIG. 83, both extending longitudinally along the tubes 752 and 756. The tubes 752 and 756 are in the embodiments outer drivers. A suitable inner driver (not shown) is also provided, as in the above embodiments.

Figure 69:
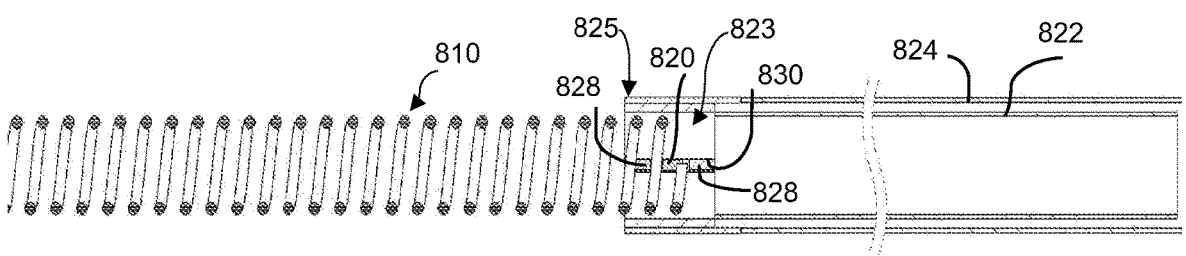
FIG. 69, in a side cross-sectional view, illustrates another manner of attaching an anchor in the system of FIG. 1 using inner and outer sleeves.

A helical anchor 810 similar to the helical anchor 710*a* is also usable in another variant illustrated with reference to FIGS. 69 to 73 in which only one anchor can be deployed before reloading. Referring to FIG. 69, in this embodiment, the anchor protrusion 820 is parallel to the longitudinal axis of the helical anchor 810. Inner and outer drivers 822 and 824 are provided respectively with inner and outer sleeves 823 and 825 at their distal ends.

Figure 70:
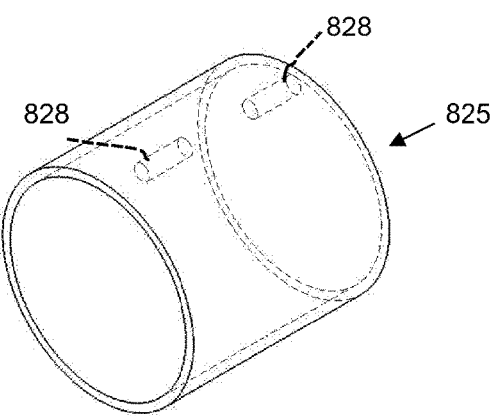
FIG. 70, in a perspective view, illustrates the outer sleeve of FIG. 69.

Referring to FIG. 70, the outer sleeve 825 is substantially cylindrical and hollow and defines a pair of longitudinally aligned protrusions 828 protruding thereinto. The protrusions 828 are spaced apart by a gap having a length similar to a length of the anchor protrusion 820 and have circumferential dimensions similar to that of the anchor protrusion 820.

Figure 71:
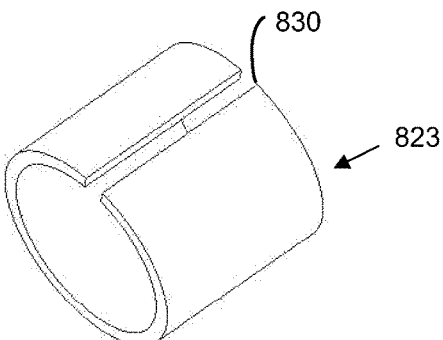
FIG. 71, in a perspective view, illustrates the inner sleeve of FIG. 69.

Referring to FIG. 71, the inner sleeve 823 is also hollow and defines a slit 830 extending therealong and leading thereinto. The inner sleeve 823 is fittingly received in the outer sleeve 825 and the slit 830 is sized for fittingly receiving the protrusions 828 and the anchor protrusion 820 thereinto. The outer diameter of the inner sleeve 823 is such that the anchor protrusion 828 is received in the slit 830 without protruding outwardly therefrom. The inner diameter of the inner sleeve 823 is such that the body of the helical anchor 810 can be received thereinto. While the interior surface of the inner sleeve 823 can be smooth, in some embodiments, the interior surface of the inner sleeve 823 is provided with a thread sized for engaging the helical anchor 810 when the latter is received in the inner sleeve 823.

Figure 72:
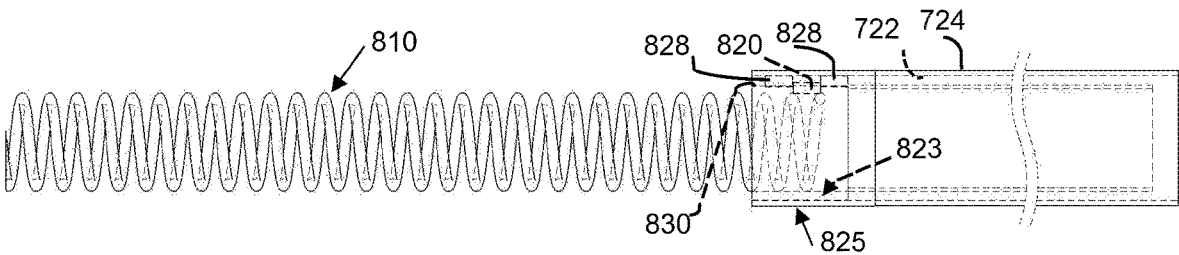
FIG. 72, in a side elevation view, illustrates the inner and outer sleeves of FIG. 69 in an extended position.
Figure 73:
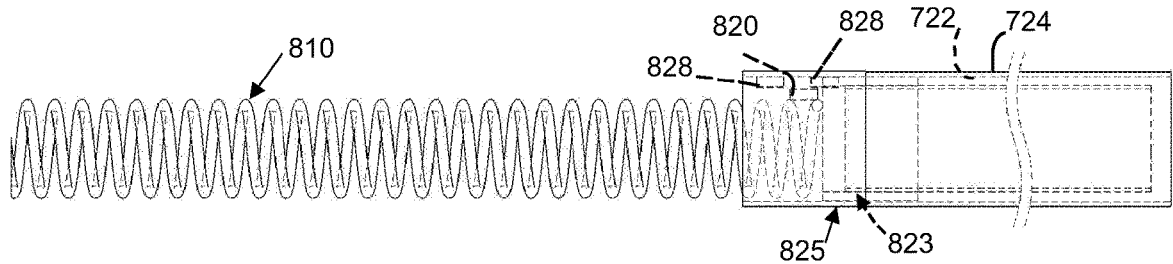
FIG. 73, in a side elevation view, illustrates the inner and outer sleeves of FIG. 69 in a retracted position.

The inner and outer drivers 722 and 724 are axially movable relative to each other between an extended position, seen in FIG. 72, in which the inner and outer sleeves 723 and 725 are in register from each other, and a retracted position, seen in FIG. 73, in which the inner sleeve 723 is retracted proximally from the outer sleeve 725.

When the helical anchor 810 is attached to the inner and outer sleeves 823 and 825, the proximal end of the helical anchor 810 is inserted in the inner sleeve 823 and the inner and outer sleeves 823 and 825 are in the extended position. The anchor protrusion 820 is between the protrusions 828, and these three elements are in the slit 830. In this configuration, the inner and outer sleeves 823 and 825 are blocked in rotation relative to each other and the anchor protrusion 820 is blocked in translation relative to the inner and outer sleeves 823 and 825. By jointly rotating the inner and outer drivers 822 and 824 without translating them relative to each other, one can drive the helical anchor 810 into biological tissue.

To release the helical anchor 810, the inner sleeve is withdrawn to the retracted position. In this configuration, the anchor protrusion 828 becomes free to rotate relative to the outer sleeve, which allows withdrawing the inner and outer drivers 822 and 824 so that the anchor can be left deployed into tissue while the inner and outer drivers 822 and 824 are withdrawn from a patient.

The inner and outer drivers 822 and 824 may be operated using any suitable actuator, such as an actuator similar to the actuator 162, but configured to retract the inner driver 722 instead of retracting the outer driver 124.

Figure 74:
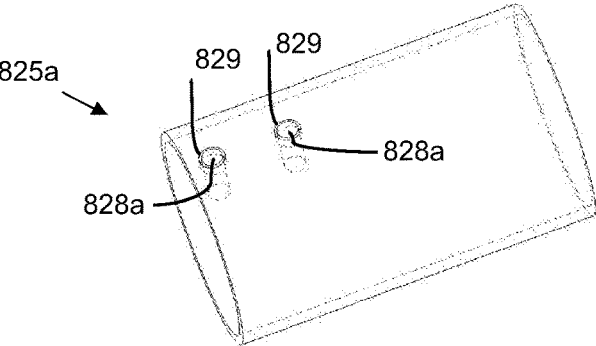
FIG. 74, in a perspective view, illustrates an alternative outer sleeve usable with the system illustrated in FIG. 69.

FIG. 74 illustrates an alternative outer sleeve 825*a* usable to replace the outer sleeve 825. In the outer sleeve 825*a*, the protrusions 828 are replaced by a pair of wires 828*a* protruding inside the outer sleeve 825*a* through a pair of suitably located apertures 829. Operation using the outer sleeve 825*a* is similar to operation using the outer sleeve 825.

FIGS. 75 to 79 illustrate yet another manner of attaching and deploying a helical anchor 910 similar to the helical anchor 710 in that it includes a radially protruding anchor protrusion 920. In some embodiments, the tip of the anchor protrusion 920 may be bent so that a small portion thereof extends parallel to the longitudinal axis of the helical anchor 910.

As seen in FIG. 75, inner and outer drivers 922 and 924 are also provided at their distal ends with respectively an inner sleeve 923 and an outer sleeve 925. Instead of releasing the helical anchor 910 by translating the inner and outer sleeves 925 relative to each other, the inner and outer sleeves 925 are rotated relative to each other to perform this release. The inner sleeve 923 is inside the outer sleeve 925, typically fittingly received thereinto.

More specifically, referring to FIG. 76, the outer sleeve 925 is cylindrical and hollow and defines an outer sleeve slot 940 extending longitudinally from the outer sleeve distal end 942 along part of the outer sleeve 925. The outer sleeve slot 940 extends between the outer and inner surfaces of the outer sleeve 925. As seen in FIG. 77 for example, the inner sleeve 923 is cylindrical and hollow and defines a substantially L-shaped inner sleeve slot 944. The inner sleeve slot 944 extends between the outer and inner surfaces of the outer sleeve 925. The inner sleeve slot 944 defines a slot longitudinal portion 946 of a configuration similar to that of the outer sleeve slot 940, and a slot circumferential portion 948 extending therefrom at the proximal end thereof.

The inner and outer sleeves 923 and 925 are movable between a locked configuration (seen in FIG. 75) and an unlocked configuration (seen in FIGS. 78 and 79). In the locked configuration, the outer sleeve slot 940 and the slot longitudinal portion 946 are offset circumferentially from each other and the closed end of the slot circumferential portion 948 is in register with the proximal end of the outer sleeve slot 940. In the unlocked configuration, the outer sleeve slot 940 and the slot longitudinal portion 946 are in register with each other.

Thus, in the locked configuration, when the helical anchor 910 is received in the inner sleeve 923 and the anchor protrusion 920 is inserted through the inner and outer sleeve slots 944 and 940, the helical anchor 910 is locked in rotation and translation relative to the inner and outer sleeves 923 and 925. This allows driving the helical anchor 910 into biological tissues by rotating jointly the inner and outer drivers 922 and 924. When the inner and outer sleeves and rotated to the unlocked configuration, one can simply remove the helical anchor 910 from the inner sleeve 923 by pulling simultaneously on the inner and outer drivers 922 and 924, as seen in the sequence of FIGS. 78 and 79.

The various features of the embodiments described hereinabove can be mixed together in any suitable manner.

Although the present invention has been described hereinabove by way of preferred embodiments thereof, it can be modified, without departing from the spirit and nature of the subject invention as defined in the appended claims.

What is claimed is:

1. A device for insertion into a lumen of an elongated catheter having a proximal and distal end, the device comprising:
   an elongate tubular outer driver sized to fit into the catheter lumen;
   an elongate inner driver, the inner and outer drivers concentric relative to each other and defining a driver passageway therebetween;
   a plurality of anchors positioned within the driver passageway adjacent respective driving sections within the driver passageway, each anchor including a helical anchor body defining anchor body proximal and distal ends and an anchor body passageway extending therethrough between the anchor body proximal and distal ends;
   cooperating features on both of the inner and outer drivers within the driver passageway and on the proximal end of each of the anchors that prevent pure translation of the anchors within the driver passageway while allowing helical movement of the anchors within the driver passageway; and an actuator operatively coupled to the inner and outer drivers and operable for selectively rotating the inner and outer drivers relative to each other to sequentially deliver each anchor of the plurality of anchors helically from the driver passageway into biological tissue;
   wherein the cooperating features comprise:
   a slot extending along a length of each driving section of the driving sections, the slot configured to direct a respective anchor of the plurality of anchors helically along the respective driving section; and
   a torque section connected to a proximal end of the driving section, the torque section configured to transmit torque between the actuator and the driving section,
   wherein the cooperating features comprise an anchor protrusion of each anchor received within a respective slot to allow movement of the respective anchor protrusion along the respective slot.

2. The device as defined in claim 1, wherein each slot is distributed helically around the respective driving section.

3. The device as defined in claim 1, each driving section further comprising a plurality of first slits and a plurality of second slits, wherein at least one of the plurality of first and plurality of second slits extend between at least a portion of a surface of the respective driving section.

4. The device as defined in claim 3, wherein at least one of the plurality of first and plurality of second slits are circumferential.

5. The device as defined in claim 1, each driving section further comprising at least one backbone region extending along a length of the respective driving section.

6. The device as defined in claim 5, each driving section further comprising at least one intermediate section extending between adjacent backbone regions or between one of the at least one backbone region and the slot.

7. The device of claim 1, wherein the inner and outer drivers are axially rotatable relative to each other and longitudinally fixed relative to each other.

8. A device for delivering a plurality of anchors into tissue, comprising:
   an elongate tubular outer driver;
   an elongate inner driver, the inner and outer drivers concentric relative to each other and defining a driver passageway therebetween;
   the plurality of anchors positioned adjacent one another within the driver passageway, each anchor including a helical anchor body defining anchor body proximal and distal ends and an anchor body passageway extending therethrough between the anchor body proximal and distal ends;
   cooperating features on both of the inner and outer drivers within the driver passageway and on the proximal end of each of the anchors that prevent pure translation of the anchors within the driver passageway while allowing helical movement of the anchors within the driver passageway; and
   an actuator operatively coupled to the inner and outer drivers and operable for selectively rotating the inner and outer drivers relative to each other to sequentially deliver each anchor of the plurality of anchors helically from the driver passageway into tissue,
   wherein the cooperating features comprise at least one protrusion protruding in the driver passageway from one of the inner and outer drivers and a protrusion extending from the proximal end of each of the anchors slidably received in a slot within the driver passageway from the other of the one of the inner and outer drivers.

9. The device of claim 8, wherein the inner and outer drivers are axially rotatable relative to each other and longitudinally fixed relative to each other.

10. The device of claim 8, wherein the at least one protrusion comprises helical protrusions having a pitch similar to a pitch of each of the plurality of anchors.

11. The device of claim 10, wherein the slot extends helically along the outer driver and wherein the at least one protrusion protrudes from the inner driver into the driver passageway.

12. The device of claim 8, wherein the cooperating features comprise a slot in the outer driver extending along one or more driving sections and a protrusion extending from the proximal end of each of the anchors that is received in a respective slot to cause the respective protrusion to move along the respective slot to advance the respective anchor helically within the driver passageway.

13. The device of claim 12, wherein each slot extends helically along each of the one or more driving sections.

14. The device of claim 8, wherein the actuator is configured such that one or more additional anchors proximal to a distal-most first anchor of the plurality of anchors advances distally to a distally adjacent driving section when the one of the inner and outer drivers is rotated to advance the first anchor from the driver passageway.

15. A device for delivering a plurality of anchors into tissue, comprising:
    an elongate tubular outer driver;
    an elongate inner driver, the inner and outer drivers concentric relative to each other and defining a driver passageway therebetween;
    the plurality of anchors positioned adjacent one another within the driver passageway, each anchor including a helical anchor body defining anchor body proximal and distal ends and an anchor body passageway extending therethrough between the anchor body proximal and distal ends;
    cooperating features on both of the inner and outer drivers within the driver passageway and on the proximal end of each of the anchors that prevent pure translation of the anchors within the driver passageway while allowing helical movement of the anchors within the driver passageway; and
    an actuator operatively coupled to the inner and outer drivers and operable for selectively rotating the inner and outer drivers relative to each other to sequentially deliver each anchor of the plurality of anchors helically from the driver passageway into tissue,
    wherein the cooperating features comprise a non-circular mounting portion on the proximal end of each anchor and a corresponding non-circular inside configuration of the outer driver.

16. The device of claim 15, wherein the cooperating features further comprise protrusion on the inner driver configured to direct the anchors helically within the driver passageway when the inner and outer drivers are rotated relative to each other.

17. The device of claim 15, wherein the inner and outer drivers are axially rotatable relative to each other and longitudinally fixed relative to each other.

18. The device of claim 15, wherein the inner and outer drivers are flexible.

19. The device of claim 18, wherein the outer driver comprises one or more backbone regions comprising slits formed in driving sections of the outer driver.

20. The device of claim 8, wherein the inner and outer drivers are flexible.

21. The device of claim 20, wherein the outer driver comprises one or more backbone regions comprising slits formed in driving sections of the outer driver.

22. A device for delivering a plurality of anchors into tissue, comprising:
    an elongate tubular outer driver;
    an elongate inner driver, the inner and outer drivers concentric relative to each other and defining a driver passageway therebetween;
    the plurality of anchors positioned adjacent one another within the driver passageway, each anchor including a helical anchor body defining anchor body proximal and distal ends and an anchor body passageway extending therethrough between the anchor body proximal and distal ends;
    cooperating features on both of the inner and outer drivers within the driver passageway and on the proximal end of each of the anchors that prevent pure translation of the anchors within the driver passageway while allowing helical movement of the anchors within the driver passageway; and
    an actuator operatively coupled to the inner and outer drivers and operable for selectively rotating the inner and outer drivers relative to each other to sequentially deliver each anchor of the plurality of anchors helically from the driver passageway into tissue,
    wherein the inner and outer drivers are flexible, and
    wherein the actuator is operatively coupled to the inner and outer drivers and operable for selectively rotating one or both of the inner and outer drivers relative to each other to sequentially:
    a) rotate one of the inner and outer drivers to advance a first anchor of the plurality of anchors from the driver passageway;
    b) rotate both of the inner and outer drivers to drive the distal end of the first anchor into tissue;
    c) rotate one of the inner and outer drivers to release the proximal end of the first anchor; and
    d) repeat steps a) to c) one or more times to deliver one or more additional anchors of the plurality of anchors.

23. The device of claim 22, wherein the inner and outer drivers are axially rotatable relative to each other and longitudinally fixed relative to each other.

24. The device of claim 22, wherein the cooperating features comprise a slot in the outer driver extending along one or more driving sections and a protrusion extending from the proximal end of each of the anchors that is received in a respective slot to cause the respective protrusion to move along the respective slot to advance the respective anchor helically within the driver passageway.

25. A device for insertion into a lumen of an elongated catheter having a proximal and distal end, the device comprising:
    an elongate tubular outer driver sized to fit into the catheter lumen;
    an elongate inner driver, the inner and outer drivers concentric relative to each other and defining a driver passageway therebetween;
    a plurality of anchors positioned within the driver passageway adjacent respective driving sections within the driver passageway, each anchor including a helical anchor body defining anchor body proximal and distal ends and an anchor body passageway extending therethrough between the anchor body proximal and distal ends;
    cooperating features on both of the inner and outer drivers within the driver passageway and on the proximal end of each of the anchors that prevent pure translation of the anchors within the driver passageway while allowing helical movement of the anchors within the driver passageway; and an actuator operatively coupled to the inner and outer drivers and operable for selectively rotating the inner and outer drivers relative to each other to sequentially deliver each anchor of the plurality of anchors helically from the driver passageway into biological tissue;

wherein the cooperating features comprise:

a slot extending along a length of each driving section of the driving sections, the slot configured to direct a respective anchor of the plurality of anchors helically along the respective driving section; wherein each slot is distributed helically around the respective driving section; and a torque section connected to a proximal end of the driving section, the torque section configured to transmit torque between the actuator and the driving section.

26. The device as defined in claim 25, each driving section further comprising a plurality of first slits and a plurality of second slits, wherein at least one of the plurality of first and plurality of second slits extend between at least a portion of a surface of the respective driving section.

27. The device as defined in claim 26, wherein at least one of the plurality of first and plurality of second slits are circumferential.

28. The device as defined in claim 25, each driving section further comprising at least one backbone region extending along a length of the driving section.

29. The device as defined in claim 28, each driving section further comprising at least one intermediate section extending between adjacent backbone regions or between one of the at least one backbone region and the slot.

* * * * *